United States Patent
Hsu et al.

(10) Patent No.: US 10,421,824 B2
(45) Date of Patent: *Sep. 24, 2019

(54) PROTEINS SPECIFIC FOR BAFF AND B7RP1

(71) Applicant: Amgen Inc., Thousand Oaks, CA (US)

(72) Inventors: Hailing Hsu, Moorpark, CA (US); Ming Zhang, Thousand Oaks, CA (US); Gunasekaran Kannan, Daly City, CA (US); Frederick Jacobsen, Newbury Park, CA (US); Wayne Tsuji, Seattle, WA (US)

(73) Assignee: AMGEN INC., Thousand Oaks, CA (US)

( * ) Notice: Subject to any disclaimer, the term of this patent is extended or adjusted under 35 U.S.C. 154(b) by 227 days.

This patent is subject to a terminal disclaimer.

(21) Appl. No.: 15/258,750

(22) Filed: Sep. 7, 2016

(65) Prior Publication Data

US 2017/0066845 A1 Mar. 9, 2017

Related U.S. Application Data

(63) Continuation of application No. 14/203,123, filed on Mar. 10, 2014, now Pat. No. 9,458,246.

(60) Provisional application No. 61/780,260, filed on Mar. 13, 2013.

(51) Int. Cl.
| | |
|---|---|
| C07K 16/28 | (2006.01) |
| A61K 39/395 | (2006.01) |
| C07K 16/46 | (2006.01) |
| A61K 45/06 | (2006.01) |
| A61K 39/00 | (2006.01) |

(52) U.S. Cl.
CPC ........ *C07K 16/468* (2013.01); *A61K 39/3955* (2013.01); *A61K 45/06* (2013.01); *C07K 16/2827* (2013.01); *C07K 16/2875* (2013.01); *A61K 2039/505* (2013.01); *C07K 2317/31* (2013.01); *C07K 2317/524* (2013.01); *C07K 2317/526* (2013.01); *C07K 2317/56* (2013.01); *C07K 2317/565* (2013.01); *C07K 2317/73* (2013.01); *C07K 2317/94* (2013.01); *C07K 2318/10* (2013.01); *C07K 2319/70* (2013.01)

(58) Field of Classification Search
None
See application file for complete search history.

(56) References Cited

U.S. PATENT DOCUMENTS

| | | | |
|---|---|---|---|
| 3,773,919 A | 11/1973 | Boswell et al. | |
| 4,399,216 A | 8/1983 | Axel et al. | |
| 4,496,689 A | 1/1985 | Mitra | |
| 4,619,794 A | 10/1986 | Hauser | |
| 4,740,461 A | 4/1988 | Kaufman | |
| 4,816,397 A | 3/1989 | Boss et al. | |
| 4,816,567 A | 3/1989 | Cabilly et al. | |
| 4,892,538 A | 1/1990 | Aebischer et al. | |
| 4,912,040 A | 3/1990 | Kaufman et al. | |
| 4,946,778 A | 8/1990 | Ladner et al. | |
| 4,959,455 A | 9/1990 | Clark et al. | |
| 4,970,154 A | 11/1990 | Chang | |
| 5,011,472 A | 4/1991 | Aebischer et al. | |
| 5,106,627 A | 4/1992 | Aebischer et al. | |
| 5,151,510 A | 9/1992 | Stec et al. | |
| 5,223,409 A | 6/1993 | Ladner et al. | |
| 5,260,203 A | 11/1993 | Ladner et al. | |
| 5,338,665 A | 8/1994 | Schatz et al. | |
| 5,432,018 A | 7/1995 | Dower et al. | |
| 5,498,530 A | 3/1996 | Schatz et al. | |
| 5,514,582 A | 5/1996 | Capon et al. | |
| 5,530,101 A | 6/1996 | Queen et al. | |
| 5,545,806 A | 8/1996 | Lonberg et al. | |
| 5,545,807 A | 8/1996 | Surani et al. | |
| 5,569,825 A | 10/1996 | Lonberg et al. | |
| 5,580,756 A | 12/1996 | Linsley et al. | |
| 5,585,089 A | 12/1996 | Queen et al. | |
| 5,593,676 A | 1/1997 | Bhat et al. | |
| 5,593,875 A | 1/1997 | Wurm et al. | |
| 5,625,126 A | 4/1997 | Lonberg et al. | |
| 5,625,825 A | 4/1997 | Rostoker et al. | |
| 5,633,425 A | 5/1997 | Lonberg et al. | |
| 5,653,975 A | 8/1997 | Baetge et al. | |
| 5,661,016 A | 8/1997 | Lonberg et al. | |
| 5,676,954 A | 10/1997 | Brigham | |
| 5,679,559 A | 10/1997 | Kim et al. | |
| 5,693,761 A | 12/1997 | Queen et al. | |
| 5,693,762 A | 12/1997 | Queen et al. | |
| 5,733,731 A | 3/1998 | Schatz et al. | |
| 5,770,429 A | 6/1998 | Lonberg et al. | |
| 5,789,650 A | 8/1998 | Lonberg et al. | |
| 5,814,318 A | 9/1998 | Lonberg et al. | |
| 5,874,299 A | 2/1999 | Lonberg et al. | |
| 5,877,397 A | 3/1999 | Lonberg et al. | |
| 5,922,545 A | 7/1999 | Mattheakis et al. | |
| 5,969,102 A | 10/1999 | Bram et al. | |
| 6,180,370 B1 | 1/2001 | Queen et al. | |

(Continued)

FOREIGN PATENT DOCUMENTS

| | | |
|---|---|---|
| EP | 0 036 676 A1 | 9/1981 |
| EP | 0 058 481 A1 | 8/1982 |

(Continued)

OTHER PUBLICATIONS

Perl A. Curr Opin Rheumatol. Sep. 2009 ; 21(5): 443-447.*

(Continued)

*Primary Examiner* — Ilia I Ouspenski

(74) *Attorney, Agent, or Firm* — Marshall, Gerstein & Borun LLP

(57) ABSTRACT

Described herein are bispecific proteins specific for BAFF and B7RP1, nucleic acids encoding such proteins, methods of making such proteins, and uses for such proteins.

13 Claims, 7 Drawing Sheets

Specification includes a Sequence Listing.

(56) References Cited

U.S. PATENT DOCUMENTS

| | | |
|---|---|---|
| 6,323,323 B1 | 11/2001 | Sledziewski et al. |
| 6,331,415 B1 | 12/2001 | Cabilly et al. |
| 6,403,770 B1 | 6/2002 | Yu et al. |
| 6,521,749 B1 | 2/2003 | Ling et al. |
| 6,869,605 B2 | 3/2005 | Browning et al. |
| 6,984,720 B1 | 1/2006 | Korman et al. |
| 7,030,225 B1 | 4/2006 | Tamatani et al. |
| 7,045,615 B2 | 5/2006 | Tamatani et al. |
| 7,112,655 B1 | 9/2006 | Tamatani et al. |
| 7,118,872 B2 | 10/2006 | Beltzer et al. |
| 7,125,551 B2 | 10/2006 | Kroczek |
| 7,132,099 B2 | 11/2006 | Kroczek |
| 7,196,175 B2 | 3/2007 | Tamatani et al. |
| 7,217,792 B2 | 5/2007 | Tamatani et al. |
| 7,226,909 B2 | 6/2007 | Tamatani et al. |
| 7,247,612 B2 | 7/2007 | Tamatani et al. |
| 7,259,137 B2 | 8/2007 | Min et al. |
| 7,259,147 B2 | 8/2007 | Tamatani et al. |
| 7,259,247 B1 | 8/2007 | Kroczek |
| 7,271,245 B2 | 9/2007 | Felding-Habermann et al. |
| 7,279,560 B2 | 10/2007 | Tamatani et al. |
| 7,294,473 B2 | 11/2007 | Tamatani et al. |
| 7,306,800 B2 | 12/2007 | Kroczek |
| 7,317,089 B2 | 1/2008 | Kikly |
| 7,435,796 B1 | 10/2008 | Yoshinaga |
| 7,521,532 B2 | 4/2009 | Dunussi-Joannopoulos et al. |
| 7,601,813 B2 | 10/2009 | Ling et al. |
| 7,695,936 B2 | 4/2010 | Carter et al. |
| 7,708,993 B2 | 5/2010 | Yoshinaga et al. |
| 7,728,109 B2 | 6/2010 | Kikly |
| 7,737,111 B2 | 6/2010 | Min et al. |
| 7,868,140 B2 | 1/2011 | Siu et al. |
| 7,928,074 B2 | 4/2011 | Khare |
| 8,062,906 B2 | 11/2011 | Beltzer et al. |
| 8,143,380 B2 | 3/2012 | Walker et al. |
| 8,507,426 B2 | 8/2013 | Min et al. |
| 8,557,243 B2 | 10/2013 | Barbas, III |
| 8,624,010 B1 | 1/2014 | Yoshinaga |
| 8,981,071 B2 | 3/2015 | Siu et al. |
| 9,458,246 B2 * | 10/2016 | Hsu .................. A61K 45/06 |
| 2002/0115831 A1 | 8/2002 | Tamatani et al. |
| 2002/0151685 A1 | 10/2002 | Tamatani et al. |
| 2002/0156242 A1 | 10/2002 | Tamatani et al. |
| 2002/0177191 A1 | 11/2002 | Kroczek |
| 2002/0182667 A1 | 12/2002 | Kroczek |
| 2003/0059937 A1 | 3/2003 | Ruben et al. |
| 2003/0078385 A1 | 4/2003 | Arathoon et al. |
| 2003/0083472 A1 | 5/2003 | Tamatani et al. |
| 2004/0054158 A1 | 3/2004 | Ling et al. |
| 2004/0073012 A1 | 4/2004 | Tamatani et al. |
| 2004/0120945 A1 | 6/2004 | Tamatani et al. |
| 2004/0132658 A1 | 7/2004 | Tamatani et al. |
| 2004/0146506 A1 | 7/2004 | Tamatani et al. |
| 2004/0151669 A1 | 8/2004 | Tamatani et al. |
| 2004/0151718 A1 | 8/2004 | Tamatani et al. |
| 2004/0151720 A1 | 8/2004 | Tamatani et al. |
| 2004/0229788 A1 | 11/2004 | Tamatani et al. |
| 2005/0261489 A1 | 11/2005 | Kroczek |
| 2006/0084608 A1 | 4/2006 | Beltzer et al. |
| 2006/0099635 A1 | 5/2006 | Ling et al. |
| 2008/0152651 A1 | 6/2008 | Yoshinaga |
| 2008/0166352 A1 | 7/2008 | Siu et al. |
| 2008/0260737 A1 | 10/2008 | Ponce et al. |
| 2009/0110676 A1 | 4/2009 | Mackay et al. |
| 2009/0148442 A1 | 6/2009 | Ponce, Jr. et al. |
| 2009/0208504 A1 | 8/2009 | Yoshinaga |
| 2009/0281286 A1 | 11/2009 | Gregg et al. |
| 2011/0014189 A1 | 1/2011 | Soula et al. |
| 2011/0059068 A1 | 3/2011 | Yoshinaga et al. |
| 2011/0104757 A1 | 5/2011 | Siu et al. |
| 2011/0117093 A1 | 5/2011 | Ruben et al. |
| 2016/0024225 A1 | 1/2016 | Hsu et al. |
| 2017/0066845 A1 | 3/2017 | Hsu et al. |

FOREIGN PATENT DOCUMENTS

| | | |
|---|---|---|
| EP | 0 088 046 A2 | 9/1983 |
| EP | 0 133 988 A2 | 3/1985 |
| EP | 0 143 949 A1 | 6/1985 |
| EP | 0 154 316 A2 | 9/1985 |
| EP | 0 526 452 A1 | 2/1993 |
| EP | 0 401 384 B1 | 3/1996 |
| EP | 0 784 680 A1 | 7/1997 |
| EP | 0 869 180 A1 | 10/1998 |
| EP | 0 939 804 A1 | 9/1999 |
| EP | 0 984 023 A1 | 3/2000 |
| EP | 1 125 585 A1 | 8/2001 |
| EP | 1 374 902 A1 | 1/2004 |
| EP | 1 502 920 A3 | 2/2005 |
| EP | 1 218504 B1 | 7/2007 |
| EP | 1 900 816 A2 | 3/2008 |
| JP | 2004-509615 A | 4/2004 |
| JP | 2004-525621 A | 8/2004 |
| JP | 2006-521085 A | 9/2006 |
| JP | 2008-505928 A | 2/2008 |
| JP | 2008-514201 A | 5/2008 |
| JP | 2009-501549 A | 1/2009 |
| JP | 2009-504191 A | 2/2009 |
| JP | 2009-515903 A | 4/2009 |
| JP | 2010-534212 A | 11/2010 |
| WO | WO-1988/001649 A1 | 3/1988 |
| WO | WO-1990/014363 A1 | 11/1990 |
| WO | WO-1991/010425 A1 | 7/1991 |
| WO | WO-1992/003918 A1 | 3/1992 |
| WO | WO-1992/022646 A1 | 12/1992 |
| WO | WO-1993/012227 A1 | 6/1993 |
| WO | WO-1993/015722 A1 | 8/1993 |
| WO | WO-1994/020069 A1 | 9/1994 |
| WO | WO-1995/011308 A1 | 4/1995 |
| WO | WO-1996/040958 A1 | 12/1996 |
| WO | WO-1996/040987 A1 | 12/1996 |
| WO | WO-1998/015833 A1 | 4/1998 |
| WO | WO-1998/018921 A1 | 5/1998 |
| WO | WO-1998/024884 A1 | 6/1998 |
| WO | WO-1998/024893 A2 | 6/1998 |
| WO | WO-1998/027114 A2 | 6/1998 |
| WO | WO-1998/038216 A1 | 9/1998 |
| WO | WO-1998/055620 A1 | 12/1998 |
| WO | WO-1998/055621 A1 | 12/1998 |
| WO | WO-1999/011791 A2 | 3/1999 |
| WO | WO-1999/012964 A2 | 3/1999 |
| WO | WO-1999/015553 A2 | 4/1999 |
| WO | WO-1999/025044 A1 | 5/1999 |
| WO | WO-1999/035170 A2 | 7/1999 |
| WO | WO-1999/062951 A1 | 12/1999 |
| WO | WO-2000/024782 A2 | 5/2000 |
| WO | WO-2000/040716 A2 | 7/2000 |
| WO | WO-2000/046240 A2 | 8/2000 |
| WO | WO-2000/047740 A2 | 8/2000 |
| WO | WO-2000/056772 A1 | 9/2000 |
| WO | WO-2000/067034 A1 | 11/2000 |
| WO | WO-2000/068378 A1 | 11/2000 |
| WO | WO-2001/002440 A1 | 1/2001 |
| WO | WO-2001/009187 A2 | 2/2001 |
| WO | WO-2001/012658 A2 | 2/2001 |
| WO | WO-2001/021796 A2 | 3/2001 |
| WO | WO-2001/064704 A1 | 9/2001 |
| WO | WO-2001/085782 A2 | 11/2001 |
| WO | WO-2002/02641 A1 | 1/2002 |
| WO | WO-2002/004364 A2 | 1/2002 |
| WO | WO-2002/008279 A1 | 1/2002 |
| WO | WO-2002/016411 A2 | 2/2002 |
| WO | WO-2002/016412 A2 | 2/2002 |
| WO | WO-2002/044364 A2 | 6/2002 |
| WO | WO-2004/043989 A2 | 5/2004 |
| WO | WO-2004/106380 A2 | 12/2004 |
| WO | WO-2006/003999 A1 | 1/2006 |
| WO | WO-2006/010057 A2 | 1/2006 |
| WO | WO-2006/036834 A2 | 4/2006 |
| WO | WO-2007/011941 A2 | 1/2007 |
| WO | WO-2007/024715 A2 | 3/2007 |
| WO | WO-2009/015345 A1 | 1/2009 |
| WO | WO-2009/089004 A1 | 7/2009 |

(56) References Cited

FOREIGN PATENT DOCUMENTS

| | | |
|---|---|---|
| WO | WO-2009/088805 A3 | 12/2009 |
| WO | WO-2012/162561 A3 | 5/2013 |
| WO | WO-2013/158577 A1 | 10/2013 |
| WO | WO-2014/144600 A2 | 9/2014 |
| WO | WO-2016/039801 A1 | 3/2016 |

OTHER PUBLICATIONS

Bartoloni et al. Arthritis Care & Research vol. 63, No. 2, Feb. 2011, pp. 178-183.*
Coca et al. Curr Opin Rheumatol 2012, 24:451-456.*
Sellam et al. Ann Rheum Dis 2007; 66:790-797.*
Vossenkämper et al. Clinical and Experimental Immunology 2011; 167: 7-14.*
Toro-Domínguez et al. Arthritis Research & Therapy 2014; 16(6): 489; 8 pages.*
Abaza et al., Effects of amino add substitutions outside an antigenic site on protein binding to monoclonal antibodies of predetermined specificity obtained by peptide immunization: Demonstration with region 94-100 (antigenic site 3) of myoglobin, *J. Protein Chem.*, 11(5): 433-44 (1992).
Abrams et al., Blockade of T lymphocyte costimulation with cytotoxic T lymphocyte-associated antigen 4-immunoglobulin (CTLA4Ig) reverses the cellular pathology of psoriatic plaques, including the activation of keratinocytes, dendritic cells, and endothelial cells, J Exp Med., 192(5): 681-94 (2000).
Abrams et al., CTLA4Ig-mediated blockade of T-cell costimulation in patients with Psoriasis vulgaris, J. Clin. Invest., 103(9): 1243-52 (1999).
Accession No. AI614037, EMBL Database, *Mus musculus* cDNA clone 5' similar to TR:075144 KIAA0653 protein (Apr. 26, 1999).
Adamczyk et al., Application of surface plasmon resonance toward studies of low-molecular-weight antigen-antibody binding interactions, *Methods*, 20(3): 319-28 (2000).
Adamczyk et al., Surface plasmon resonance (SPR) as a tool for antibody conjugate analysis, *Bioconjugate Chem.*, 10: 1032-37 (1999).
Adames et al., The c-myc oncogene driven by immunoglobulin enhancers induces lymphoid malignancy in transgenic mice, Nature, 318: 533-8 (1985).
Alexander et al., Expression of the c-myc oncogene under control of an immunoglobulin enhancer in E mu-myc transgenic mice, *Mol. Cell. Biol.*, 7(4): 1436-44 (1987).
Altschul et al., Basic local alignment search tool, *J. Molec. Biol.*, 215: 403-10 (1990).
Anderson et al., Rheumatoid arthritis disease activity measures: American College of Rheumatology recommendations for use in clinical practice. *Arthritis Care Res.* 64 (5): 640-7 (2012).
Aruffo et al, Molecular cloning of a CD28 cDNA by a high-efficiency COS cell expression system, Proc. Natl. Acad. Sci. USA, 84: 8573-7 (1987).
Attwood et al., Genomics: The babel of bioinformatics, Science, 290: 471-3 (2000).
Ausubel et al., Current Protocols in Molecular Biology, Green Publishers, Inc. and Wiley and Sons, N.Y. (1994) [Table of Contents Only].
Beck et al., Strategies and challenges for the next generation of therapeutic antibodies. *Nat. Rev. Immunol.* 10: 345-52 (2010).
Benoist et al., In vivo sequence requirements of the SV40 early promoter region, *Nature*, 290(5804): 304-10 (1981).
Best et al., Development of a Crohn's disease activity index. National Cooperative Crohn's Disease Study, *Gastroenterol.* 70: 439-44 (1976).
Blaher et al., T cell response to grass pollen allergens: Correlation with skin test reactivity and serum IgE levels, *Immunol. Cell Biol.*, 73: 17-22 (1995).

Blazar et al., Infusion of anti-B7.1 (CD80) and anti-B7.2 (CD86) monoclonal antibodies inhibits murine graft-versus-host diseases lethality in part via direct effects on CD4+ and CD8+ T Cells, *J. Immunol.*, 157: 3250-9 (1996).
Boerner et al., Production of antigen-specific human monoclonal antibodies from in vitro-primed human splenocytes, *J. Immunol.*, 147(1): 86-95 (1991).
Bombardier et al., Derivation of the SLEDAI. A disease activity index for lupus patients. The Committee on Prognosis Studies in SLE, *Arthr. & Rheum.* 35(6): 630-40 (1992).
Bowie et al., Deciphering the message in protein sequences: Tolerance to amino acid substitutions, *Science*, 247: 1306-10 (1990).
Brinster et al., Regulation of metallothionein-thymidine kinase fusion plasmids injected into mouse eggs, Nature, 296(5852): 39-42 (1982).
Brodie et al., LICOS, aprimordial costimulatory ligand, *Curr. Biol.* 10(6): 333-6 (2000).
Bruggemann et al., Designer mice: The production of human antibody repertoires in transgenic animals, *Year Immun.*, 7: 33-40 (1993).
Brunat et al., A new member of the immunoglobulin superfamily-CTLA-4, *Nature*, 328: 267-70 (1987).
Burton et al., Human antibody effector function, *Adv. Immunol.*, 51:1-84 (1992).
Carillo et al., The multiple sequence alignment problem in biology, *SIAM J. Appl. Math.*, 48: 1073 (1988).
Casset et la., A peptide mimetic of an anti-CD4 monoclonal antibody by rational design. *Biochem. Biophys. Res. Commun.* 307(1): 198-205 (2002).
Chang et al., B Cell Activating Factor (BAFF) and T Cells Cooperate to Breach B Cell Tolerance in Lupus-Prone New Zealand (NZB) Mice, *PLoS One*, 5(7):e11691 (2010).
Cheema et al., Elevated Serum B Lymphocyte Stimulator Levels in Patients With Systemic Immune—Based Rheumatic Diseases, *Arthr. & Rheum.* 44(6):1313-19. (2001).
Cheema et al., Increased B Lymphocyte Stimulator (BlySTM) Protein in HIV-Patients: Correlation with Anti-Cardiolipin (aCL) and Anti-Phospholipid (aPL) Autoantibodies, abstract (2002).
Chen et al., Immunoglobulin gene rearrangement in B cell deficient mice generated by targeted deletion of the JH locus, *Int. Immunol.*, 5(6): 647-56 (1993).
Chen et al., Selection and analysis of an optimized anti-VEGF antibody: Crystal structure of an affinity-matered Fab in complex with antigen. *J. Mol. Biol.* 293: 865-81 (1999).
Chirinos-Rojas et al., A Phage-Displayed Mimotope Inhibits Tumour Necrosis Factor-Induced Cytotoxicity More Effectively Than the Free Mimotope, *Immunology*, 96:109-13 (1999).
Chu et al., SV40 DNA transfection of cells in suspension: analysis of efficiency of transcription and translation of T-antigen, *Gene*, 13(2):197-202 (1981).
Cole et al., The EBV-hybridoma technique and its application to human lung cancer, Monoclonal Antibodies and Cancer Therapy, Alan R. Liss, p. 77 (1985).
Colman et al., Effects of amino acid sequence changes on antibody-antigen interactions, *Res. Immunol.*, 145(1): 33-6 (1994).
Coyle et al., The CD28-related molecule ICOS is required for effective T cell-dependent immune responses, *Immunity*, 13(1): 95-105 (2000).
Coyle et al., The expanding B7 superfamily: Increasing complexity in costimulatory signals regulating T cell function, *Nat. Immunol.*, 2: 203-9 (2001).
Creighton (Ed.), Proteins, Structures and Molecular Principles, Freeman and Company, New York, TOC (1984).
Cwirla et al., Peptide Agoinist of the Thrombopoietin Receptor as Potent as the Natural Cytokine, *Science*, 276:1696-9 (1997).
Dai et al., The role of cytokines, CTLA-4 and costimulation in transplant tolerance and rejection, *Curr. Opin. Immunol.*, 11(5): 504-8 (1999).
Dariavach et al., Human Ig superfamily CTLA-4 gene: chromosomal localization and identity of protein sequence between murine and human CTLA-4 cytoplasmic domains, *Eur. J. Immunol.*, 18: 1901-5 (1988).

(56) References Cited

OTHER PUBLICATIONS

Database EMBL—*Homo sapiens* mRNA for KIAA0653 protein, partial cds.—EBI Accession No. AB014553 (Feb. 6, 1999).
Database EMBL—vg32f09.r1 Soares mouse mammary gland NbMMG Mus muscu/us cDNA clone IMAGE:863081.5, mRNA sequence—EMBL Accession No. AA510455 (Jul. 9, 1997).
Database EMBL—yg34c12.r1 Soares infant brain 1 NIB Homo sapiens cDNA clone IMAGE:34465.5, mRNA sequence—EBI Accession No. R23544 (Apr. 23, 1995).
Database UNIPROT, O'Regan et al., ICOS ligand—UNIPROT Accession No. 042404 (Jan. 1, 1998).
Database UNIPROT, Wang et al., ICOS ligand precursor (B7 homolog 2) (B7-H2) (B7-like protein G150) (B7-related protein 1) (P7RP-1) (CD275 antigen)—UNIPROT Accession No. 075144 (Jul. 15, 1999).
Davidson, The rationale for BAFF inhibition in systemic lupus erythematosus, The rationale for BAFF Inhibition in Systemic Lypus Erythematosus, *Curr. Rheum. Rept.*, 14 (4):295-302 (2012).
Davis et at., Basic Methods in Molecular Biology, Elsevier (1986) [Table of Contents].
Dayhoff et al., A model of evolutionary change in proteins, *Atlas Protein Seq. Struct*, 5: Supp. 3 (1978).
DeBoer et al., The tac promoter: A functional hybrid derived from the trp and lac promoters, *Proc. Natl Acad. Sci. USA*, 8: 21-5 (1983).
Del Prete et al., IL-4 is an essential factor for the IgE synthesis induced in vitro by human T cell clones and their supernatants, *J. Immunol.* 140(12): 4193-8 (1988).
DePascalis, Grafting of abbreviated complementarity-determining regions containing specificity-determining residues essential for ligand contact to engineer a less immunogenic humanized monoclonal antibody, *J. Immunol.*, 169: 3076-84 (2002).
Desmyter et al., Antigen specificity and high affinity binding provided by one single loop of a camel single-domain antibody. *J. Biol. Chem.* 276: 26285-90 (2001).
Devareaux et al., A comprehensive set of sequence analysis programs for VAX, *Nucl. Acids Res.* 12: 387 (1984).
Devlin et al., Random Peptide Libraries: A Source of Specific Protein Binding Molecules, *Science*, 249:404-6 (1990).
Dong et al., Regulation of immune and autoimmune responses by ICOS. *J. Autoimmun.* 21: 255-60 (2003).
Dwyer et al., The use of concanavalin A to study the immunoregulation of human T cells. *Clin. Exp. Immunol.*, 46:237-49 (1981).
Edelman et al., The covalent structure of an entire gammaG immunoglobulin molecule. *Proc. Natl. Acad. Sci.* 63: 78-85 (1969).
Edgar, T cell immunodeficiency, *J. Clin. Pathol.*, 61(9): 988-93 (2008).
Engels et al,. Gene synthesis, *Angew. Chem. Intl. Ed.*, 28: 716-34 (1989).
Eppstein et al., Biological activity of liposome-encapsulated murine interferon .gamma. is mediated by a cell membrane receptor, *Proc. Natl. Acad. Sci. USA*, 62: 3688-92 (1985).
European Patent Office, European Search Report and Written Opinion for EP07019762.9 dated Dec. 5, 2008.
European Patent Office, European Search Report and Written Opinion for EP10178373.6 dated Dec. 20, 2010.
European Patent Office, Supplementary Partial European Search Report for EP02769739.0 dated Aug. 2, 2005.
European Search Report, EP 14180109.2, dated May 13, 2015.
Fick et al., Immunotherapy approach to allergic disease, *Immunopharmacol.*, 48(3):7-10 (2000).
Fishwild et al., High-avidity human IgG kappa monoclonal antibodies from a novel strain of minilocus transgenic mice, *Nat. Biotechnol.*, 14(7): 845-51 (1996).
Francis, Protein modification and fusion proteins, *Focus Growth Factors*, 3: 4-10 (1992).
Freeman et al., B7, a new member of the Ig superfamily with unique expression on activated and neoplastic B cells, *J. Immunol.*, 143: 2714-22 (1989).
Freeman et al., Cloning of B7-2: A CTLA-4 counter-receptor that costimuates human T cell proliferation, *Science*, 262: 909-11 (1993).

Freeman et al., Murine B7-2, an alternative CTLA4 counter-receptor that costimulates T cell proliferation and interleukin 2 production, *J. Exp. Med.*, 178: 2185-92 (1993).
Freeman et al., Structure, expression, and T cell costimulatory activity of the murine homologue of the human B lymphocyte, *J. Exp. Med.*, 174: 625-31 (1991).
Frisque et al., Infectivity of the DNA from four isolates of JC virus, *Virology*, 32(2): 476-82 (1973).
Goeddel, Systems for heterologous gene expression, *Meth. Enzymol.*, 185: 3-7 (1990) [Table of Contents].
Graham et al., A new technique for the assay of infectivity of human adenovirus 5 DNA, *Virology*, 52(2): 456-67 (1973).
Gribskov et al., Sequence analysis primer, Stockton Press, N.Y. (1991) [Table of Contents].
Griffin et al., Computer analysis of sequence data, Part 1, Humana Press, N.J. (1994) [Table of Contents].
Gross et al., TACT and BCMA are Receptors for a TNF Homologue Implicated in B-Cell Autoimmune Disease, *Nature*, 404:995-9 (2000).
Gross et al., The murine homologue of the T lymphocyte antigen CD28, *J. Immunol.*, 144:3201-10 (1990).
Grosschedl et al., Introduction of a mu immunoglobulin gene into the mouse germ line: Specific expression in lymphoid cells and synthesis of functional antibody, *Cell*, 38(3):647-58 (1984).
Gruss et al., Tumor Necrosis Factor Ligand Superfamily: Involvement in the Pathology of Malignant Lymphomas, *Blood*, 85:3378-3404 (1995).
Hammer et al., Diversity of alpha-fetoprotein gene expression in mice is generated by a combination of separate enhancer elements, *Science*, 235(4784): 53-8 (1987).
Hanahan, Heritable formation of pancreatic beta-cell tumours in transgenic mice expressing recombinant insulin/simian virus 40 oncogenes, *Nature*, 315(6015): 115-22 (1985).
Harding et al., Class switching in human immunoglobulin transgenic mice, *Ann. N.Y. Acad. Sci.*, 764: 536-46 (1995).
Hatzoglou et al., TNF Receptor Family Member BCMA (B Cell Maturation) Associates with TNF Receptor-Associated Factor (TRAF) 1, TRAF2, and TRAF3 and Activates NF-KB, Elk-1, c-Jun N-Terminal Kinase, and p38 Mitogen-Activated Protein Kinase, *J. Immunol.* 165:1322-30 (2000).
Hay et al., the BILAG index: a reliable and valid instrument for measuring clinical disease activity in systemic lupus erythematosus. *Q. J. Med.* 86: 447-58 (1993).
Heany et al., Severe asthma treatment: need for characterizing patients, *Lancet*, 365: 974-6 (2005).
Henikoff et al., Amino acid substitution matrices from protein blocks, *Proc. Natl. Acad. Sci. USA*, 89: 10915-19 (1992).
Henry et al., Cloning, structural analysis and mapping of the B30 and B7 multigenic families to the major histocompatibility complex (MMC) and other chromosomal regions, *Immunogenetics*, 46: 383-95 (1997).
Holliger et al., 'Diabodies': Small Bivalent and Bispecific Antibody Fragments, *Proc. Natl. Acad. Sci.* 90:6444-6448 (1993).
Holm et al., Functional mapping and single chain construction of the anti-cytokeratin 8 monoclonal antibody TS1, *Mol. Immunol.*, 44(6): 1075-84 (2007).
Hoogenboom et al., By-passing immunisation. Human antibodies from synthetic repertoires of germline VH gene segments rearranged in vitro, *J. Mol. Biol.*, 227(2): 381-8 (1992).
Houghten et al., General method for the rapid solid-phase synthesis of large numbers of peptides: Specificity of antigen-antibody interaction at the level of individual amino acids, *Proc. Natl. Acad. Sci. USA*, 82: 5132 (1985).
Hu et al., B7RP-1 blockade ameliorates autoimmunity through regulation of follicular helper T cells, *J. Immunol.*, 182: 1421-8 (2009).
Hu et al., Noncanonical NF-B regulates inducible costimulator (ICOS) ligand expression and T follicular helper cell development, *Proc. Nat. Acad. Sci. USA*, 108(31):12827-32 (2011).
Huang, Structural chemistry and therapeutic intervention of protein-protein interactions in immune response, human immunodeficiency virus entry, and apoptosis, *Pharmacol. Therapeut.*, 86: 201-15 (2000).

(56) References Cited

OTHER PUBLICATIONS

Hutloff et al., ICOS is an inducible T-cell co-stimulator structurally and functionally related to CD28, *Nature*, 397: 263-6 (1999).

Ishikawa et al., Prediction of the coding sequences of unidentified human gene. X. The complete sequences of 100 new cDNA clones from brain which can code for large proteins in vitro, *DNA Res.*, 5: 169-76 (1998).

Iwahi et al., Amelioration of collagen-included arthritis by blockade of inducible costimulator-B7 homologous protein costimulation-B7 homologous protein costimulation, *J. Immunol.*, 4332-9 (2002).

Jakobovits et al., Analysis of homozygous mutant chimeric mice: Deletion of the immunoglobin heavy-chain joining region block B-cell development and antibody production, *Proc. Natl. Acad. Sci. USA*, 90: 2551-5 (1993).

Jakobovits et al., Germ-like transmission and expression of a human-derived yeast artificial chromosome, *Nature*, 362: 255-65 (1993).

Jones et al., Replacing the complementary-determining regions in a human antibody with those from a mouse, *Nature*, 321: 522-5 (1986).

Kahan, Immunosuppressive therapy, *Curr. Opin. Immunol.*, 4: 553-9 (1992).

Kelsey et al., Species-and tissue-specific expression of human alpha 1-antitrypsin in transgenic mice, *Genes Devel.*, 1(2): 161-71 (1987).

Khare et al., Severe B cell hyperplasia and autoimmune disease in TALL-1 transgenis mice, *Proc. Natl. Acad. Sci. USA.*, 97(7):3370-5 (2000).

Khayyamian et al., ICOS-ligand, expressed on human endothelial cells, costimulates h1 and Th2 cytokine secretion by memory CD4+ T cells. *Proc. Natl. Acad. Sci. USA*, 99(9): 6198-203 (2002).

Kimmel et al., Preparation of cDNA and the generation of cDNA libraries: Overview. *Meth. Enzymol.*, 152: 307-16 (1987).

Kitts et al., A method for producing recombinant baculovirus expression vectors at high frequency, *Biotechniques*, 14: 810-7 (1993).

Kohler et al., Continuous cultures of fused cells secreting antibody of predefined specificity, *Nature*, 256(5517): 495-7 (1975).

Kollias et al., Regulated expression of human a gamma-, beta-, and hybrid gamma beta-globin genes in transgenic mice: manipulation of the developmental expression patterns, *Cell*, 46(1): 89-94 (1986).

Kontermann, Bispecific Antibodies: Developments and Current Perspectives, Bispecific Antibodies, 1-28 (2011).

Kostelny et al., Formation of a bispecific antibody by the use of leucine zippers, *J. Immunol.*, 148(5): 1547-53 (1992).

Kotzin, Systemic lupus erythematosus, *Cell*, 85: 303-6 (1996).

Kremer et al., Treatment of rheumatoid arthritis by selective inhibition of T-cell activation with fusion protein CTLA4lg, *New Engl. J. Med.*, 349(20): 1907-15 (2003).

Krumlauf et al., Developmental regulation of alpha-fetoprotein genes in transgenic mice, *Mol. Cell. Biol.*, 5(7): 1639-48 (1985).

Langer et al., Biocompatibility of polymeric delivery systems for macromolecules, *J. Biomed. Mater. Res.* 15: 267-277 (1981).

Langer, Controlled release of macromolecules, *Chem Tech.*, 12: 98-105 (1982).

LaPlanche et al., Phosphorothioate-modified oligodeoxyribonucleotides. III. NMR and UV spectroscopic studies of the Rp-Rp, Sp-Sp, and Rp-Sp duplexes, [d(GGSAATTCC)]2, derived from diastereomeric 0-ethyl phosphorothioates, *Nucl. Acids Res.*, 14(22): 9081-93 (1986).

Leder et al., Consequences of widespread deregulation of the c-myc gene in transgenic mice: multiple neoplasms and normal development, *Cell*, 45(4): 485-95 (1986).

Lederman et al., A single amino acid substitution in a common African allele of the CD4 molecule ablates binding of the monoclonal antibody, OKT4, *Molec. Immunol.*, 28: 1171-81 (1991).

Lesk, Computational molecular biology, Oxford University Press, N.Y. (1996) [Table of Contents].

Li et al., Beta-endorphin omission analogs: Dissociation of immunoreactivity from other biological activities, *Proc. Natl. Acad. Sci. USA*, 77: 3211-4 (1980).

Ling et al., Cutting edge: Identification of GL50, a novel B7-line protein that functionally binds to ICOS receptor, *J. Immunol.*, 164(4): 1653-7 (2000).

Lonberg et al., Antigen-specific human antibodies from mice comprising four distinct genetic modifications, *Nature*, 368(6474): 856-9 (1994).

Lonberg et al., Human antibodies from transgenic mice, *Intern. Rev. Immunol.*, 13(1): 65-93 (1995).

Lonberg, Transgenic approaches to human monoclonal antibodies, *Handbook of Experimental Pharmacology*, 113: 49-101 (1994).

Lowman et al., Bacteriophage Display and Discovery of Peptide Leads for Drug Development, *Ann. Rev. Biophys. Biomol. Struct.* 26:401-24 (1997).

Lucklow, Baculovirus systems for the expression of human gene products, *Curr. Opin. Biotech.*, 4: 564-72 (1993).

Luckow et al., Efficient generation of infectious recombinant baculoviruses by site-specific transposon-mediated insertion of foreign genes into a baculovirus genome propagated in *Escherichia coli*, *J. Virol.*, 67: 4566-79 (1993).

Lutz et al., ICOS/B7RP-1 Interference in mouse kidney transplantation, *Transplantation*, 84(2): 223-30 (2007).

MacCallum et al., Antibody-antigen Interactions: Contact analysis and finding site topography, *J. Mol. Biol.*, 262(5): 732-45 (1996).

MacDonald, Expression of the pancreatic elastase I gene in transgenic mice, *Hepatology*, 7(1 Suppl): 42S-51S (1987).

Magnan et al., Relationship between natural T cells, atopy, IgE levels, and IL-4 production, *Allergy*, 55: 286-90 (2000).

Marks et al., By-passing immunization human antibodies from V-gene libraries displayed on phage, *J. Molec. Biol.*, 222: 581 (1991).

Marsters et al., Interaction of the TNF Homologues BlyS and APRIL with the TNF Receptor Homologues BCMA and TACI, *Curr. Biol.* 10:785-8 (2000).

Marston et al., Solubilization of protein aggregates, *Meth. Enzymol.* 182: 264-75 (1990).

Mason et al., The hypogonadal mouse: Reproductive functions restored by gene therapy, *Science*, 234: 1372-78 (1986).

McAdam et al., Mouse inducible costimulatory molecule (ICOS) expression is enhanced by CD28 costimulation and regulates differentiation of CD4+ T cells. *J. Immunol.* 165(9): 5035-40 (2000).

McDonald et al., Isolation of RNA using guanidinium salts, *Meth. Enzymol.*, 152: 219 (1987).

Medesan et al., Comparative studies of rat IgG to further delineate the Fc:FcRn interaction site, *Eur. J. Immunol.*, 28(7): 2092-100 (1998).

Mendez et al., Functional transplant of megabase human immunoglobulin loci recapitulates human antibody response in mice, *Nat. Genet.*, 15(2): 146-56 (1997).

Merrifield et al., Solid phase peptide synthesis. I. The synthesis of a tetrapeptide, *J. Amer. Chem. Soc.* 85: 2149 (1963).

Metzler, et al., Solution structure of human CTLA-4 and delineation of a CD80/CD86 binding site conserved in CE28, *Nat. Struct. Biol.*, 4: 527-531 (1997).

Milgrom et al., Treatment of allergic asthma with monoclonal anti-IgE antibody, *New Engl. J. Med.*, 341(26): 1966-73 (1999).

Mogram et al., Developmental regulation of a cloned adult betaglobin gene in transgenic mice, *Nature*, 315(6017): 338-40 (1985).

Morrison, et al, Chimeric human antibody molecules: Mouse antigen-binding domains with human constant region domains, *Proc. Natl. Acad. Sci. USA*, 81: 6851-5 (1985).

Mukhopadhyay et al., Identification and Characterization of a Novel Cytokine, THANK, a TNF Homologue That Activates Apoptosis, Nuclear Factor-KB, and c-June NH2Terminal Kinase, *J. Biol. Chem.*, 274(23):15978-81 (1999).

Muyldermans et al., Single domain camel antibodies: current status. *J. Biotechnol.* 74: 277-302 (2001).

Needlemen, et al, A General Method Applicable to the Search for Similarities in the Amino Acid Sequence of Two Proteins, *J. Mol. Biol.*, 48: 443-53 (1970).

Neuberger et al., Generating high-avidity human Mabs in mice. *Nat. Biotechnol.* 14: 826 (1996).

(56) References Cited

OTHER PUBLICATIONS

Ngo et al., The protein folding problem and tertiary structure prediction, Merz et al, (Ed.), Birkhauser, Boston, MA, 433 and 492-495 (1994).
Ogden, et al, Electrophoresis in agarose and acrylamide gels, *Meth. Enzymol.* 152: 61 (1987).
Oren et al. Structural Basis of BlyS Receptor Recognition, Nature Structural Biology 9(4): 288-92 (2002).
Ornitz et al., Elastase I promoter directs expression of human growth hormone and SV40 T antigen genes to pancreatic acinar cells in transgenic mice, *Cold Spring Harbor Symp. Quant Biol.* 50: 399-409 (1986).
Pinkert et al., An albumin enhancer located 10 kb upstream functions along with its promoter to direct efficient, liver-specific expression in transgenic mice, *Genes Devel.*, 1(3): 268-76 (1987).
Rahman et al., Systemic lupus erythematosus, *N. Engl. J. Med.*, 358:929-39 (2008).
Ravetch et al., IgG Fc receptors, *Annu. Rev. Immunol.*, 19: 275-90 (2001).
Readhead et al., Expression of a myelin basic protein gene in transgenic shiverer mice: Correction of the dysmyelinating phenotype, *Cell*, 48(4): 703-12 (1987).
Remington's Pharmaceutical Sciences, 18th Edition, Mack Publishing Company (1990) [Table of Contents].
Rentero et al., Screening of large molecule diversities by phage display, *Chimia*, 65: 843-5. (2011).
Richter et al., Tumor necrosis factor-alpha regulates the expression of inducible costimulator receptor ligand on CD34+ progenitor cells during differentiation into antigen presenting cells, *J. Biol. Chem.*, 276(49): 45686-93 (2001).
Riechmann, et al, Reshaping human antibodies for therapy, *Nature*, 332: 323-327 (1988).
Riley et al., the CD28 family: a T-cell rheostat for therapeutic control of T-cell activation, *Blood*, 105: 13-21 (2005).
Roberts et al., RNA-Peptide Fusions for the in vitro Selection of Peptides and Proteins, *Proc. Natl. Acad. Sci. USA*, 94: 12297-302 (1997).
Rudikoff et al., Single amino acid substitution altering antigen-binding specificity, *Proc. Natl. Acad. Sci. USA*, 79: 1979-83 (1982).
Sambrook et al., Molecular Cloning: A Laboratory Manual, Cold Springs Harbor Laboratory Press, Cold Spring Harbor, N.Y. (1989) [Table of Contents].
Samoylova et al. Phage probes for malignant glial cells, *Mol. Cancer Ther.*, 2:1129-1137 (2003).
Sani, Tissue-specific expression of rat myosin light-chain 2 gene in transgenic mice, *Nature*, 314: 283-86 (1985).
Schultz et al., B7-mediated costimulation and the immune response, *Blood Rev.*, 10(2): 111-27 (1996).
Scott et al., Searching for Peptide Ligands with an Epitope Library, *Science*, 249: 386-390 (1990).
Sekut et al., Characterization of a Human Monoclonal Antibody that Antagonizes B-Lymphocyte Stimulator Bioactives, abstract (2002).
Sequence alignment, 1 page, Ling et al. U.S. Pat. No. 6,521,749.
Shields et al., High resolution mapping of the binding site on human IgG1 for Fc gamma RI, Fc gamma RI I, Fc gamma RIII, and FcRn and design of IgG1 variants with improved binding to the Fc gamma R, *J. Biol. Chem.*, 276(9): 6591-604 (2001).
Shimamoto et al., Peptibodies: A flexible alternative format to antibodies. *MAbs*, 4(5): 586-91 (2012).
Shu et al., B cell maturation protein is a receptor for the tumor necrosis factor family member Tall-1, *Proc. Natl. Acad. Sci. USA*, 97(16):9156-61. (2000).
Shu et al., TALL-1 is a Novel Member of the TNF Family that is Down-Regulated by Mitogens, *J. Leukocyte Biol.* 65:680-3 (1999).
Sidman et al., Controlled release of macromolecules and pharmaceuticals from synthetic polypeptides based on glutamic acid, *Biopolymers*, 22: 547-56 (1983).
Sifuentes et al., New targets in Systemic Lupus (part 2/2), Reumatologia Clinica (English Edition), 8(5):263-9 (2012).
Skolnick et al., From genes to protein structure and function: novel applications of computational approaches in the genomic era, *Trends in Biotech*, 18(1): 34-9 (2000).
Smith et al., Biocomputing: Informatics and genome projects, Academic Press, N.Y. (1993) [Table of Contents].
Smith et al., The TNF Receptor Superfamily of Cellular and Viral Proteins: Activation, Costimulation, and Death, *Cell*, 76:959-62 (1994).
Songsivilai et al., Bispecific antibody: A tool for diagnosis and treatment of disease, *Clin. Exp Immunol.*, 79(3): 315-21 (1990).
Stec et al., Automated solid phase synthesis, separation and stereochemistry of phosphothioate analogues of oligodeoxyribonucleotides, *J. Am. Chem. Soc.*, 106: 6077 (1984).
Stein et al., Physicochemical properties of phosphorothioate oligodeoxynucleotides, *Nucl. Acids Res.*, 16(8): 3209-21 (1988).
Stoll et al., Further validation of the BILAG disease activity index in patients with systemic lupus erythematosus, *Ann. Rheum Dis.*, 55:756-60 (1996).
Streltsov et al., Structure of a shark IgNAR antibody variable domain and modeling of an early-developmental isotype. *Protein Sci.* 14: 2901-9 (2005).
Swift et al., Tissue-specific expression of the rat pancreatic elastase I gene in transgenic mice, *Cell*, 38(3): 639-46 (1984).
Tafuri et al., ICOS is essential for effective T-helper-cell response, *Nature*, 409:105-9 (2001).
Takasaki et al., Structure-based Design and Characterization of Exocyclic Peptidomimetics that Inhibit TNFa Binding to its Receptor, *Nat. Biotech.*, 15:1266-1270 (1997).
Tan et al., Local Production of B Lymphocyte Stimulator (BlySTM) Protein in Human Arthritic Joints, abstract. (2002).
Taylor et al., A transgenic mouse that expresses a diversity of human sequence heavy and light chain immunoglobulins, *Nucl. Acids Res.*, 20(23): 6287-95 (1992).
Taylor et al., Human immunoglobulin transgenes undergo rearrangement, somatic mutation and class switching in mice that lack endogenous IgM, *Int. Immunol.*, 6(4): 579-91 (1994).
Telleman et al., The role of the Brambell receptor (FcRB) in liver: protection of endocytosed immunoglobulin G (IgG) from catabolism in hepatocytes rather than transport of IgG to bile, *Immunology*, 100(2): 245-51 (2000).
Thompson et al., BAFF Binds to the Tumor Necrosis Factor Receptor-Like Molecule B Cell Maturation Antigen and is Important for Maintaining the Peripheral B Cell Population, *J. Exp. Med.*, 192:129-35 (2000).
Thomsen et al., Promoter-regulatory region of the major immediate early gene of human cytomegalovirus, *Proc. Natl. Acad. Sci. USA*, 81(3): 659-63 (1984).
Thornton et al., Protein structure: Prediction of progress at last, *Nature*, 354(6349): 105-6 (1991).
Totsuka et al., Amerliorating effect of anti-inducible costimulator monoclonal antibody in a murine model of chronic colitis, *Gastroenterology*, 410-21 (2003).
Tuaillon et al., Biased utilization of DHQ52 and JH4 gene segments in a human Ig transgenic minilocus independent of antigenic selection, *J. Immunol.*, 152(6): 2912-20 (1994).
U.S. Appl. No. 12/286,099, Final Office Action dated Oct. 13, 2011.
U.S. Appl. No. 12/286,099, Non-final Office Action dated Jan. 28, 2011.
U.S. Appl. No. 12/286,099, Restriction Requirement Office Action dated Jul. 6, 2010.
U.S. Appl. No. 11/359,254, now U.S. Pat. No. 7,708,993—Final Office Action dated Jul. 16, 2008.
U.S. Appl. No. 11/359,254, now U.S. Pat. No. 7,708,993—Nonfinal Office Action dated Feb. 23, 2007.
U.S. Appl. No. 11/359,254, now U.S. Pat. No. 7,708,993'Nonfinal Office Action dated May 22, 2009.
United States Patent and Trademark Office, International Search Report for PCT/US02/15273 dated Apr. 22, 2003.
Vajdos et al., Comprehensive functional maps of the Antigen-binding site of an anti-ErbB2 antibody obtained with shotgun scanning mutagenesis, *J. Mol. Biol.*, 320(2): 415-28 (2002).
Verhoeyen et al., Reshaping human antibodies: Grafting an antilysozyme activity, *Science*, 239: 1534-8 (1988).

(56) References Cited

OTHER PUBLICATIONS

Villa-Kamaroff et al., A bacterial clone synthesizing proinsulin, *Proc. Natl. Acad. Sci U.S.A.*, 75: 3727-31 (1978).

Voet et al., Biochemistry, John Wiley & Sons, 1: 126-8 and 230 (1990).

von Heinje, Sequence Analysis in Molecular Biology, Academic Press (1987) [Table of Contents].

Vratsanos et al., 'Systemic Lupus Erythematosus', Samter's Immunological Diseases, Ch. 39, 6 Ed. (2001).

Wagner et al.: Nucleotide sequence of the thymidine kinase gene of herpes simplex virus type 1, *Proc. Natl. Acad. Sci. U.S.A.*, 78: 1441-5 (1981).

Wahl et al., Interaction of B&RP1 with ICOS negatively regulates antigen presentation by B cells, *Inflammation*, 27(4): 191-200 (2003).

Wahl et al., Molecular hybridization of immobilized nucleic acids: theoretical concepts and practical considerations. *Methods Enzymol.*, 152: 399-407 (1987).

Wahl et al., Renal tubular epithelial expression of the costimulatory molecule B7RP-1 (Inducible Costimulator Ligand), *J. Am. Soc. Nephrol.*, 13: 1517-26 (2002).

Walter et al., New targets in systemic Lupus (Part 2/2). *Reumatologia Clinica*, 8(5): 263-9 (2012).

Wang et al., Costimulation of T cells by B7-H2, a B7-like molecule that binds ICOS, *Blood*, 96(8): 2808-13 (2000).

Ware, APRIL and BAFF Connect Autoimmunity and Cancer, *J. Exp. Med.*, 192(11): F35-F37 (2000).

Ware, Decoy Receptors Thwart B Cells, *Nature*, 404:949-950 (2000).

Watanabe et al., Down-regulation of ICOS Ligand by Interaction with ICOS functions as a regulatory Mechanism for Immune Responses, *J. Immunol.*, 180(8):5222-34 (2008).

Wells et al., Rapid Evolution of Peptide and Protein Binding Properties in Vitro, *Curr. Opin. Biotechnol*, 3:355-62 (1992).

Wu et al., Humanization of a murine monoclonal antibody by simultaneous optimization of framework and CDR residues, *J. Mol. Biol.*, 294: 151-62 (1999).

Xia et al., TACI is a TRAF-Interacting Receptor for TALL-1, a Tumor Necrosis Factor Family Member Involved in B Cell Regulation, *J. Exp. Med.*, 192:137-43 (2000).

Yamamoto et al., Identification of a functional promoter in the long terminal repeat of Rous sarcoma virus, *Cell*, 22(3): 787-97 (1980).

Yoshinaga et al., T-cell co-stimulation through B7RP-1 and ICOS, *Nature*. 402(6763): 827-32 (1999).

Yoshinga et al., Characterization of a new human B7-related protein: B7RP-1 is the ligand to the co-stimulatory protein ICOS, *Int. Immun.*, 12(10): 1439-47 (2000).

Yu et al., ARPIL and TALL-1 and Receptors BCMA and TACI: System for Regulating Humoral Immunity, *Nat. Immunol.* 1:252-256 (2000).

Zhang et al., Cutting Edge: A Role for B Lymphocyte Stimulator in Systemic Lupus Erythematosus. *J. Immunology*, 166:6-10 (2001).

Zhang et al., ICOS-dependent and -independent functions of memory CD4 T cells in allograft rejection, *Am. J. Transplant.*, 8: 497-506 (2008).

Zola, Using monoclonal antibodies: Soluble antigens. Monoclonal Antibodies: A Manual of Techniques, CRC Press, pp. 147-158 (1987).

Zon et al., Phosphorothioate oligonucleotides: Chemistry, purification, analysis, scale-up and future directions, *Anti-Cancer Drug Design*, 6(6): 539-68 (1991).

Zou et al., Gene targeting in the lgx locus: Efficient generation of I chain-expressing B cells, independent of gene rearrangements in lgx, *EMBO J.*, 12: 811-20 (1993).

Singh et al., "The T cell in Sjogren's syndrome: Force majeure, not spectateur," Journal of Autoimmunity 39:229-233 (2012).

* cited by examiner

| Construct name | P71617 | P71618 | P71619 | P71620 | P71621 | P71622 | P71523 |
|---|---|---|---|---|---|---|---|
| Construct feature | N-fusion-HC | N-fusion-LC | C-fusion-1K | C-fusion-G4S | 2x Fc Loop | 1x Fc Loop 1x C-fusion | 1x CH2 1x CH3 |
| Construct design |  |  |  |  |  |  |  |

SEQUENCE LISTING

```
<160> NUMBER OF SEQ ID NOS: 71

<210> SEQ ID NO 1
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Leu Pro Gly Cys Lys Trp Asp Leu Leu Ile Lys Gln Trp Val Cys Asp
1               5                   10                  15

Pro Leu

<210> SEQ ID NO 2
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Phe His Asp Cys Lys Trp Asp Leu Leu Thr Lys Gln Trp Val Cys His
1               5                   10                  15

Gly Leu

<210> SEQ ID NO 3
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Trp, Tyr or Phe
```

```
<220> FEATURE:
<221> NAME/KEY: MOD_RES
<222> LOCATION: (5)..(5)
<223> OTHER INFORMATION: Any amino acid
<220> FEATURE:
<221> NAME/KEY: MOD_RES
<222> LOCATION: (7)..(7)
<223> OTHER INFORMATION: Thr or Ile
<220> FEATURE:
<221> NAME/KEY: MOD_RES
<222> LOCATION: (8)..(8)
<223> OTHER INFORMATION: Lys, Arg or His
<220> FEATURE:
<221> NAME/KEY: MOD_RES
<222> LOCATION: (10)..(10)
<223> OTHER INFORMATION: Lys, Arg, His, Ala, Val, Leu, Ile, Pro, Phe,
      Trp or Met

<400> SEQUENCE: 3

Cys Lys Xaa Asp Xaa Leu Xaa Xaa Gln Xaa Val Cys
1               5                   10

<210> SEQ ID NO 4
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Gly Gly Gly Gly
1

<210> SEQ ID NO 5
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (12)..(12)
<223> OTHER INFORMATION: Ser or Val

<400> SEQUENCE: 5

Gly Ser Gly Ser Ala Thr Gly Gly Ser Gly Ser Xaa Ala Ser Ser Gly
1               5                   10                  15

Ser Gly Ser Ala Thr His Leu
            20

<210> SEQ ID NO 6
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Gly Ser Gly Ser Ala Thr Gly Gly Ser Gly Ser Val Ala Ser Ser Gly
1               5                   10                  15

Ser Gly Ser Ala Thr His Leu
            20
```

```
<210> SEQ ID NO 7
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Gly Ser Gly Ser Ala Thr Gly Gly Ser Gly Ser Ser Ala Ser Ser Gly
1               5                   10                  15

Ser Gly Ser Ala Thr His Leu
            20

<210> SEQ ID NO 8
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Arg Ala Ser Gln Gly Ile Ser Asn Trp Leu Ala
1               5                   10

<210> SEQ ID NO 9
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Ala Ala Ser Ser Leu Gln Ser
1               5

<210> SEQ ID NO 10
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Gln Gln Tyr Asp Ser Tyr Pro Arg Thr
1               5

<210> SEQ ID NO 11
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Ser Tyr Trp Met Ser
1               5

<210> SEQ ID NO 12
<211> LENGTH: 17
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 12

Tyr Ile Lys Gln Asp Gly Asn Glu Lys Tyr Tyr Val Asp Ser Val Lys
1               5                   10                  15

Gly

<210> SEQ ID NO 13
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Glu Gly Ile Leu Trp Phe Gly Asp Leu Pro Thr Phe
1               5                   10

<210> SEQ ID NO 14
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Trp
            20                  25                  30

Leu Ala Trp Tyr Gln Gln Lys Pro Glu Lys Ala Pro Lys Ser Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asp Ser Tyr Pro Arg
                85                  90                  95

Thr Phe Gly Gln Gly Thr Lys Val Glu Ile Lys Arg
            100                 105

<210> SEQ ID NO 15
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ala Tyr Ile Lys Gln Asp Gly Asn Glu Lys Tyr Tyr Val Asp Ser Val
    50                  55                  60
```

```
Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Glu Gly Ile Leu Trp Phe Gly Asp Leu Pro Thr Phe Trp Gly
            100                 105                 110

Gln Gly Thr Leu Val Thr Val Ser Ser
        115                 120
```

<210> SEQ ID NO 16
<211> LENGTH: 509
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

```
Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ala Tyr Ile Lys Gln Asp Gly Asn Glu Lys Tyr Tyr Val Asp Ser Val
    50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Glu Gly Ile Leu Trp Phe Gly Asp Leu Pro Thr Phe Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Cys Ser Arg Ser Thr Ser Glu Ser Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Asn Phe Gly Thr Gln Thr Tyr Thr Cys Asn Val Asp His
        195                 200                 205

Lys Pro Ser Asn Thr Lys Val Asp Lys Thr Val Glu Arg Lys Cys Cys
    210                 215                 220

Val Glu Cys Pro Pro Cys Pro Ala Pro Pro Val Ala Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Phe Arg Val Val Ser
```

```
            290                 295                 300
Val Leu Thr Val Val His Gln Asp Trp Leu Asn Gly Lys Glu Tyr Lys
305                 310                 315                 320

Cys Lys Val Ser Asn Lys Gly Leu Pro Ala Pro Ile Glu Lys Thr Ile
                325                 330                 335

Ser Lys Thr Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Met Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Gly Gly
        435                 440                 445

Gly Gly Leu Pro Gly Cys Lys Trp Asp Leu Leu Ile Lys Gln Trp Val
    450                 455                 460

Cys Asp Pro Leu Gly Ser Gly Ser Ala Thr Gly Gly Ser Gly Ser Gly
465                 470                 475                 480

Ala Ser Ser Gly Ser Gly Ser Ala Thr Gly Ser Leu Pro Gly Cys Lys
                485                 490                 495

Trp Asp Leu Leu Ile Lys Gln Trp Val Cys Asp Pro Leu
            500                 505

<210> SEQ ID NO 17
<211> LENGTH: 511
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ala Tyr Ile Lys Gln Asp Gly Asn Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Gly Ile Leu Trp Phe Gly Asp Leu Pro Thr Phe Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Cys Ser Arg Ser Thr Ser Glu Ser Thr Ala
    130                 135                 140
```

```
Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
            165                 170                 175

Val Leu Gln Ser Ser Gly Leu Tyr Ser Leu Ser Ser Val Val Thr Val
        180                 185                 190

Pro Ser Ser Asn Phe Gly Thr Gln Thr Tyr Thr Cys Asn Val Asp His
    195                 200                 205

Lys Pro Ser Asn Thr Lys Val Asp Lys Thr Val Glu Arg Lys Cys Cys
210                 215                 220

Val Glu Cys Pro Pro Cys Pro Ala Pro Pro Val Ala Gly Pro Ser Val
225                 230                 235                 240

Phe Leu Phe Pro Pro Lys Pro Lys Asp Thr Leu Met Ile Ser Arg Thr
            245                 250                 255

Pro Glu Val Thr Cys Val Val Asp Val Ser His Glu Asp Pro Glu
        260                 265                 270

Val Gln Phe Asn Trp Tyr Val Asp Gly Val Glu Val His Asn Ala Lys
    275                 280                 285

Thr Lys Pro Arg Glu Glu Gln Phe Asn Ser Thr Phe Arg Val Val Ser
290                 295                 300

Val Leu Thr Val Val His Gln Asp Trp Leu Asn Gly Lys Glu Tyr Lys
305                 310                 315                 320

Cys Lys Val Ser Asn Lys Gly Leu Pro Ala Pro Ile Glu Lys Thr Ile
            325                 330                 335

Ser Lys Thr Lys Gly Gln Pro Arg Glu Pro Gln Val Tyr Thr Leu Pro
        340                 345                 350

Pro Ser Arg Glu Glu Met Thr Lys Asn Gln Val Ser Leu Thr Cys Leu
    355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Met Leu Asp Ser
385                 390                 395                 400

Asp Gly Ser Phe Phe Leu Tyr Ser Lys Leu Thr Val Asp Lys Ser Arg
            405                 410                 415

Trp Gln Gln Gly Asn Val Phe Ser Cys Ser Val Met His Glu Ala Leu
        420                 425                 430

His Asn His Tyr Thr Gln Lys Ser Leu Ser Leu Ser Pro Gly Lys Gly
    435                 440                 445

Gly Gly Gly Gly Leu Pro Gly Cys Lys Trp Asp Leu Leu Ile Lys Gln
450                 455                 460

Trp Val Cys Asp Pro Leu Gly Ser Gly Ser Ala Thr Gly Gly Ser Gly
465                 470                 475                 480

Ser Val Ala Ser Ser Gly Ser Gly Ser Ala Thr His Leu Leu Pro Gly
            485                 490                 495

Cys Lys Trp Asp Leu Leu Ile Lys Gln Trp Val Cys Asp Pro Leu
        500                 505                 510
```

<210> SEQ ID NO 18
<211> LENGTH: 511
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

-continued

```
Glu Val Gln Leu Val Glu Ser Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ala Tyr Ile Lys Gln Asp Gly Asn Glu Lys Tyr Tyr Val Asp Ser Val
        50                  55                  60

Lys Gly Arg Phe Thr Ile Ser Arg Asp Asn Ala Lys Asn Ser Leu Tyr
65              70                  75                  80

Leu Gln Met Asn Ser Leu Arg Ala Glu Asp Thr Ala Val Tyr Tyr Cys
                85                  90                  95

Ala Arg Glu Gly Ile Leu Trp Phe Gly Asp Leu Pro Thr Phe Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Cys Ser Arg Ser Thr Ser Glu Ser Thr Ala
        130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
            165                 170                 175

Val Leu Gln Ser Ser Gly Leu Tyr Ser Leu Ser Ser Val Val Thr Val
        180                 185                 190

Pro Ser Ser Asn Phe Gly Thr Gln Thr Tyr Thr Cys Asn Val Asp His
            195                 200                 205

Lys Pro Ser Asn Thr Lys Val Asp Lys Thr Val Glu Arg Lys Cys Cys
        210                 215                 220

Val Glu Cys Pro Pro Cys Pro Ala Pro Pro Val Ala Gly Pro Ser Val
225                 230                 235                 240

Phe Leu Phe Pro Pro Lys Pro Lys Asp Thr Leu Met Ile Ser Arg Thr
            245                 250                 255

Pro Glu Val Thr Cys Val Val Val Asp Val Ser His Glu Asp Pro Glu
        260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Phe Arg Val Val Ser
        290                 295                 300

Val Leu Thr Val Val His Gln Asp Trp Leu Asn Gly Lys Glu Tyr Lys
305                 310                 315                 320

Cys Lys Val Ser Asn Lys Gly Leu Pro Ala Pro Ile Glu Lys Thr Ile
            325                 330                 335

Ser Lys Thr Lys Gly Gln Pro Arg Glu Pro Gln Val Tyr Thr Leu Pro
        340                 345                 350

Pro Ser Arg Glu Glu Met Thr Lys Asn Gln Val Ser Leu Thr Cys Leu
            355                 360                 365

Val Lys Gly Phe Tyr Pro Ser Asp Ile Ala Val Glu Trp Glu Ser Asn
        370                 375                 380

Gly Gln Pro Glu Asn Asn Tyr Lys Thr Thr Pro Pro Met Leu Asp Ser
385                 390                 395                 400

Asp Gly Ser Phe Phe Leu Tyr Ser Lys Leu Thr Val Asp Lys Ser Arg
            405                 410                 415
```

```
Trp Gln Gln Gly Asn Val Phe Ser Cys Ser Val Met His Glu Ala Leu
                420                 425                 430

His Asn His Tyr Thr Gln Lys Ser Leu Ser Leu Ser Pro Gly Lys Gly
            435                 440                 445

Gly Gly Gly Gly Leu Pro Gly Cys Lys Trp Asp Leu Leu Ile Lys Gln
        450                 455                 460

Trp Val Cys Asp Pro Leu Gly Ser Gly Ser Ala Thr Gly Gly Ser Gly
465                 470                 475                 480

Ser Ser Ala Ser Ser Gly Ser Gly Ser Ala Thr His Leu Leu Pro Gly
                485                 490                 495

Cys Lys Trp Asp Leu Leu Ile Lys Gln Trp Val Cys Asp Pro Leu
                500                 505                 510
```

<210> SEQ ID NO 19
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Trp
            20                  25                  30

Leu Ala Trp Tyr Gln Gln Lys Pro Glu Lys Ala Pro Lys Ser Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asp Ser Tyr Pro Arg
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 20
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

```
<220> FEATURE:
<221> NAME/KEY: MOD_RES
<222> LOCATION: (2)..(9)
<223> OTHER INFORMATION: Any amino acid

<400> SEQUENCE: 20

Cys Xaa Xaa Xaa Xaa Xaa Xaa Xaa Xaa
1               5

<210> SEQ ID NO 21
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Leu Glu Trp Ile Gly
1               5

<210> SEQ ID NO 22
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Any amino acid

<400> SEQUENCE: 22

Trp Gly Xaa Gly
1

<210> SEQ ID NO 23
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Any amino acid

<400> SEQUENCE: 23

Phe Gly Xaa Gly
1

<210> SEQ ID NO 24
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Gly Ser Gly Ser Ala Thr Gly Gly Ser Gly Ser Gly Ala Ser Ser Gly
1               5                   10                  15

Ser Gly Ser Ala Thr Gly Ser
            20

<210> SEQ ID NO 25
```

<211> LENGTH: 447
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 25

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ala Tyr Ile Lys Gln Asp Gly Asn Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Gly Ile Leu Trp Phe Gly Asp Leu Pro Thr Phe Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Cys Ser Arg Ser Thr Ser Glu Ser Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Asn Phe Gly Thr Gln Thr Tyr Thr Cys Asn Val Asp His
        195                 200                 205

Lys Pro Ser Asn Thr Lys Val Asp Lys Thr Val Glu Arg Lys Cys Cys
    210                 215                 220

Val Glu Cys Pro Pro Cys Pro Ala Pro Pro Val Ala Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Phe Arg Val Val Ser
    290                 295                 300

Val Leu Thr Val Val His Gln Asp Trp Leu Asn Gly Lys Glu Tyr Lys
305                 310                 315                 320

Cys Lys Val Ser Asn Lys Gly Leu Pro Ala Pro Ile Glu Lys Thr Ile
                325                 330                 335

Ser Lys Thr Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn

```
                370                 375                 380
Gly Gln Pro Glu Asn Asn Tyr Lys Thr Thr Pro Pro Met Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
                420                 425                 430

His Asn His Tyr Thr Gln Lys Ser Leu Ser Leu Ser Pro Gly Lys
        435                 440                 445

<210> SEQ ID NO 26
<211> LENGTH: 508
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

Leu Pro Gly Cys Lys Trp Asp Leu Leu Ile Lys Gln Trp Val Cys Asp
1               5                   10                  15

Pro Leu Gly Ser Gly Ser Ala Thr Gly Gly Ser Gly Ser Gly Ala Ser
                20                  25                  30

Ser Gly Ser Gly Ser Ala Thr Gly Ser Leu Pro Gly Cys Lys Trp Asp
        35                  40                  45

Leu Leu Ile Lys Gln Trp Val Cys Asp Pro Leu Gly Gly Glu Val Gln
50                  55                  60

Leu Val Glu Ser Gly Gly Gly Leu Val Gln Pro Gly Gly Ser Leu Arg
65                  70                  75                  80

Leu Ser Cys Ala Ala Ser Gly Phe Thr Phe Ser Ser Tyr Trp Met Ser
                85                  90                  95

Trp Val Arg Gln Ala Pro Gly Lys Gly Leu Glu Trp Val Ala Tyr Ile
                100                 105                 110

Lys Gln Asp Gly Asn Glu Lys Tyr Tyr Val Asp Ser Val Lys Gly Arg
        115                 120                 125

Phe Thr Ile Ser Arg Asp Asn Ala Lys Asn Ser Leu Tyr Leu Gln Met
    130                 135                 140

Asn Ser Leu Arg Ala Glu Asp Thr Ala Val Tyr Tyr Cys Ala Arg Glu
145                 150                 155                 160

Gly Ile Leu Trp Phe Gly Asp Leu Pro Thr Phe Trp Gly Gln Gly Thr
                165                 170                 175

Leu Val Thr Val Ser Ser Ala Ser Thr Lys Gly Pro Ser Val Phe Pro
                180                 185                 190

Leu Ala Pro Cys Ser Arg Ser Thr Ser Glu Ser Thr Ala Ala Leu Gly
        195                 200                 205

Cys Leu Val Lys Asp Tyr Phe Pro Glu Pro Val Thr Val Ser Trp Asn
    210                 215                 220

Ser Gly Ala Leu Thr Ser Gly Val His Thr Phe Pro Ala Val Leu Gln
225                 230                 235                 240

Ser Ser Gly Leu Tyr Ser Leu Ser Ser Val Val Thr Val Pro Ser Ser
                245                 250                 255

Asn Phe Gly Thr Gln Thr Tyr Thr Cys Asn Val Asp His Lys Pro Ser
                260                 265                 270

Asn Thr Lys Val Asp Lys Thr Val Glu Arg Lys Cys Cys Val Glu Cys
        275                 280                 285
```

```
Pro Pro Cys Pro Ala Pro Val Ala Gly Pro Ser Val Phe Leu Phe
    290             295             300

Pro Pro Lys Pro Lys Asp Thr Leu Met Ile Ser Arg Thr Pro Glu Val
305             310                 315                 320

Thr Cys Val Val Val Asp Val Ser His Glu Asp Pro Glu Val Gln Phe
                325                 330                 335

Asn Trp Tyr Val Asp Gly Val Glu Val His Asn Ala Lys Thr Lys Pro
            340                 345                 350

Arg Glu Glu Gln Phe Asn Ser Thr Phe Arg Val Val Ser Val Leu Thr
                355                 360                 365

Val Val His Gln Asp Trp Leu Asn Gly Lys Glu Tyr Lys Cys Lys Val
370                 375                 380

Ser Asn Lys Gly Leu Pro Ala Pro Ile Glu Lys Thr Ile Ser Lys Thr
385                 390                 395                 400

Lys Gly Gln Pro Arg Glu Pro Gln Val Tyr Thr Leu Pro Pro Ser Arg
                405                 410                 415

Glu Glu Met Thr Lys Asn Gln Val Ser Leu Thr Cys Leu Val Lys Gly
                420                 425                 430

Phe Tyr Pro Ser Asp Ile Ala Val Glu Trp Glu Ser Asn Gly Gln Pro
            435                 440                 445

Glu Asn Asn Tyr Lys Thr Thr Pro Pro Met Leu Asp Ser Asp Gly Ser
450                 455                 460

Phe Phe Leu Tyr Ser Lys Leu Thr Val Asp Lys Ser Arg Trp Gln Gln
465                 470                 475                 480

Gly Asn Val Phe Ser Cys Ser Val Met His Glu Ala Leu His Asn His
                485                 490                 495

Tyr Thr Gln Lys Ser Leu Ser Leu Ser Pro Gly Lys
                500                 505

<210> SEQ ID NO 27
<211> LENGTH: 275
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Leu Pro Gly Cys Lys Trp Asp Leu Leu Ile Lys Gln Trp Val Cys Asp
1               5                   10                  15

Pro Leu Gly Ser Gly Ser Ala Thr Gly Gly Ser Gly Ser Gly Ala Ser
                20                  25                  30

Ser Gly Ser Gly Ser Ala Thr Gly Ser Leu Pro Gly Cys Lys Trp Asp
            35                  40                  45

Leu Leu Ile Lys Gln Trp Val Cys Asp Pro Leu Gly Gly Asp Ile Gln
        50                  55                  60

Met Thr Gln Ser Pro Ser Ser Leu Ser Ala Ser Val Gly Asp Arg Val
65                  70                  75                  80

Thr Ile Thr Cys Arg Ala Ser Gln Gly Ile Ser Asn Trp Leu Ala Trp
                85                  90                  95

Tyr Gln Gln Lys Pro Glu Lys Ala Pro Lys Ser Leu Ile Tyr Ala Ala
                100                 105                 110

Ser Ser Leu Gln Ser Gly Val Pro Ser Arg Phe Ser Gly Ser Gly Ser
            115                 120                 125

Gly Thr Asp Phe Thr Leu Thr Ile Ser Ser Leu Gln Pro Glu Asp Phe
        130                 135                 140
```

Ala Thr Tyr Tyr Cys Gln Gln Tyr Asp Ser Tyr Pro Arg Thr Phe Gly
145                 150                 155                 160

Gln Gly Thr Lys Val Glu Ile Lys Arg Thr Val Ala Ala Pro Ser Val
            165                 170                 175

Phe Ile Phe Pro Pro Ser Asp Glu Gln Leu Lys Ser Gly Thr Ala Ser
        180                 185                 190

Val Val Cys Leu Leu Asn Asn Phe Tyr Pro Arg Glu Ala Lys Val Gln
    195                 200                 205

Trp Lys Val Asp Asn Ala Leu Gln Ser Gly Asn Ser Gln Glu Ser Val
210                 215                 220

Thr Glu Gln Asp Ser Lys Asp Ser Thr Tyr Ser Leu Ser Ser Thr Leu
225                 230                 235                 240

Thr Leu Ser Lys Ala Asp Tyr Glu Lys His Lys Val Tyr Ala Cys Glu
            245                 250                 255

Val Thr His Gln Gly Leu Ser Ser Pro Val Thr Lys Ser Phe Asn Arg
        260                 265                 270

Gly Glu Cys
        275

<210> SEQ ID NO 28
<211> LENGTH: 511
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ala Tyr Ile Lys Gln Asp Gly Asn Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Gly Ile Leu Trp Phe Gly Asp Leu Pro Thr Phe Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Cys Ser Arg Ser Thr Ser Glu Ser Thr Ala
130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
            165                 170                 175

Val Leu Gln Ser Ser Gly Leu Tyr Ser Leu Ser Ser Val Val Thr Val
        180                 185                 190

Pro Ser Ser Asn Phe Gly Thr Gln Thr Tyr Thr Cys Asn Val Asp His
    195                 200                 205

Lys Pro Ser Asn Thr Lys Val Asp Lys Thr Val Glu Arg Lys Cys Cys

```
                    210                 215                 220
Val Glu Cys Pro Pro Cys Pro Ala Pro Val Ala Gly Pro Ser Val
225                 230                 235                 240

Phe Leu Phe Pro Pro Lys Pro Lys Asp Thr Leu Met Ile Ser Arg Thr
            245                 250                 255

Pro Glu Val Thr Cys Val Val Val Asp Val Ser His Glu Asp Pro Glu
                260                 265                 270

Val Gln Phe Asn Trp Tyr Val Asp Gly Val Glu Val His Asn Ala Lys
            275                 280                 285

Thr Lys Pro Arg Glu Glu Gln Phe Asn Ser Thr Phe Arg Val Val Ser
290                 295                 300

Val Leu Thr Val Val His Gln Asp Trp Leu Asn Gly Lys Glu Tyr Lys
305                 310                 315                 320

Cys Lys Val Ser Asn Lys Gly Leu Pro Ala Pro Ile Glu Lys Thr Ile
                325                 330                 335

Ser Lys Thr Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Met Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Gly Gly
        435                 440                 445

Gly Gly Leu Pro Gly Cys Lys Trp Asp Leu Leu Ile Lys Gln Trp Val
450                 455                 460

Cys Asp Pro Leu Gly Gly Gly Ser Gly Gly Gly Ser Gly Gly
465                 470                 475                 480

Gly Gly Ser Gly Gly Gly Ser Gly Gly Gly Ser Leu Pro Gly
            485                 490                 495

Cys Lys Trp Asp Leu Leu Ile Lys Gln Trp Val Cys Asp Pro Leu
                500                 505                 510
```

<210> SEQ ID NO 29
<211> LENGTH: 510
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 29

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ala Tyr Ile Lys Gln Asp Gly Asn Glu Lys Tyr Tyr Val Asp Ser Val
    50                  55                  60
```

```
Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Glu Gly Ile Leu Trp Phe Gly Asp Leu Pro Thr Phe Trp Gly
            100                 105                 110

Gln Gly Thr Leu Val Thr Val Ser Ala Ser Thr Lys Gly Pro Ser
        115                 120                 125

Val Phe Pro Leu Ala Pro Cys Ser Arg Ser Thr Ser Glu Ser Thr Ala
        130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
                180                 185                 190

Pro Ser Ser Asn Phe Gly Thr Gln Thr Tyr Thr Cys Asn Val Asp His
                195                 200                 205

Lys Pro Ser Asn Thr Lys Val Asp Lys Thr Val Glu Arg Lys Cys Cys
210                 215                 220

Val Glu Cys Pro Pro Cys Pro Ala Pro Pro Val Ala Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Phe Arg Val Val Ser
290                 295                 300

Val Leu Thr Val Val His Gln Asp Trp Leu Asn Gly Lys Glu Tyr Lys
305                 310                 315                 320

Cys Lys Val Ser Asn Lys Gly Leu Pro Ala Pro Ile Glu Lys Thr Ile
                325                 330                 335

Ser Lys Thr Lys Gly Gln Pro Arg Glu Pro Gln Val Tyr Thr Leu Pro
                340                 345                 350

Pro Ser Arg Glu Glu Met Gly Gly Leu Pro Gly Cys Lys Trp Asp Leu
            355                 360                 365

Leu Ile Lys Gln Trp Val Cys Asp Pro Leu Gly Ser Gly Ser Ala Thr
        370                 375                 380

Gly Gly Ser Gly Ser Gly Ala Ser Ser Gly Ser Gly Ser Ala Thr Gly
385                 390                 395                 400

Ser Leu Pro Gly Cys Lys Trp Asp Leu Leu Ile Lys Gln Trp Val Cys
                405                 410                 415

Asp Pro Leu Gly Gly Thr Lys Asn Gln Val Ser Leu Thr Cys Leu Val
                420                 425                 430

Lys Gly Phe Tyr Pro Ser Asp Ile Ala Val Glu Trp Glu Ser Asn Gly
            435                 440                 445

Gln Pro Glu Asn Asn Tyr Lys Thr Thr Pro Pro Met Leu Asp Ser Asp
        450                 455                 460

Gly Ser Phe Phe Leu Tyr Ser Lys Leu Thr Val Asp Lys Ser Arg Trp
465                 470                 475                 480

Gln Gln Gly Asn Val Phe Ser Cys Ser Val Met His Glu Ala Leu His
```

```
                      485                 490                 495
Asn His Tyr Thr Gln Lys Ser Leu Ser Leu Ser Pro Gly Lys
            500                 505                 510

<210> SEQ ID NO 30
<211> LENGTH: 490
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ala Tyr Ile Lys Gln Asp Gly Asn Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Gly Ile Leu Trp Phe Gly Asp Leu Pro Thr Phe Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Cys Ser Arg Ser Thr Ser Glu Ser Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Asn Phe Gly Thr Gln Thr Tyr Thr Cys Asn Val Asp His
        195                 200                 205

Lys Pro Ser Asn Thr Lys Val Asp Lys Thr Val Glu Arg Lys Cys Cys
    210                 215                 220

Val Glu Cys Pro Pro Cys Pro Ala Pro Pro Val Ala Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Phe Arg Val Val Ser
    290                 295                 300

Val Leu Thr Val Val His Gln Asp Trp Leu Asn Gly Lys Glu Tyr Lys
305                 310                 315                 320

Cys Lys Val Ser Asn Lys Gly Leu Pro Ala Pro Ile Glu Lys Thr Ile
                325                 330                 335
```

```
Ser Lys Thr Lys Gly Gln Pro Arg Glu Pro Gln Val Tyr Thr Leu Pro
            340                 345                 350

Pro Ser Arg Glu Glu Met Gly Gly Leu Pro Gly Cys Lys Trp Asp Leu
            355                 360                 365

Leu Ile Lys Gln Trp Val Cys Asp Pro Leu Gly Gly Thr Lys Asn Gln
        370                 375                 380

Val Ser Leu Thr Cys Leu Val Lys Gly Phe Tyr Pro Ser Asp Ile Ala
385                 390                 395                 400

Val Glu Trp Glu Ser Asn Gly Gln Pro Glu Asn Asn Tyr Lys Thr Thr
                405                 410                 415

Pro Pro Met Leu Asp Ser Asp Gly Ser Phe Phe Leu Tyr Ser Lys Leu
            420                 425                 430

Thr Val Asp Lys Ser Arg Trp Gln Gln Gly Asn Val Phe Ser Cys Ser
            435                 440                 445

Val Met His Glu Ala Leu His Asn His Tyr Thr Gln Lys Ser Leu Ser
            450                 455                 460

Leu Ser Pro Gly Gly Gly Gly Leu Pro Gly Cys Lys Trp Asp Leu
465                 470                 475                 480

Leu Ile Lys Gln Trp Val Cys Asp Pro Leu
        485                 490
```

<210> SEQ ID NO 31
<211> LENGTH: 491
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 31

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ala Tyr Ile Lys Gln Asp Gly Asn Glu Lys Tyr Tyr Val Asp Ser Val
50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
            85                  90                  95

Ala Arg Glu Gly Ile Leu Trp Phe Gly Asp Leu Pro Thr Phe Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Cys Ser Arg Ser Thr Ser Glu Ser Thr Ala
        130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Asn Phe Gly Thr Gln Thr Tyr Thr Cys Asn Val Asp His
            195                 200                 205
```

```
Lys Pro Ser Asn Thr Lys Val Asp Lys Thr Val Glu Arg Lys Cys Cys
            210                 215                 220
Val Glu Cys Pro Pro Cys Pro Ala Pro Pro Val Ala Gly Pro Ser Val
225                 230                 235                 240
Phe Leu Phe Pro Pro Lys Pro Lys Asp Thr Leu Met Ile Ser Arg Thr
                245                 250                 255
Pro Glu Val Thr Cys Val Val Val Asp Val Ser His Gly Gly Leu Pro
            260                 265                 270
Gly Cys Lys Trp Asp Leu Leu Ile Lys Gln Trp Val Cys Asp Pro Leu
        275                 280                 285
Gly Gly Glu Asp Pro Glu Val Gln Phe Asn Trp Tyr Val Asp Gly Val
    290                 295                 300
Glu Val His Asn Ala Lys Thr Lys Pro Arg Glu Glu Gln Phe Asn Ser
305                 310                 315                 320
Thr Phe Arg Val Val Ser Val Leu Thr Val Val His Gln Asp Trp Leu
                325                 330                 335
Asn Gly Lys Glu Tyr Lys Cys Lys Val Ser Asn Lys Gly Leu Pro Ala
            340                 345                 350
Pro Ile Glu Lys Thr Ile Ser Lys Thr Lys Gly Gln Pro Arg Glu Pro
        355                 360                 365
Gln Val Tyr Thr Leu Pro Pro Ser Arg Glu Glu Met Gly Gly Leu Pro
    370                 375                 380
Gly Cys Lys Trp Asp Leu Leu Ile Lys Gln Trp Val Cys Asp Pro Leu
385                 390                 395                 400
Gly Gly Thr Lys Asn Gln Val Ser Leu Thr Cys Leu Val Lys Gly Phe
                405                 410                 415
Tyr Pro Ser Asp Ile Ala Val Glu Trp Glu Ser Asn Gly Gln Pro Glu
            420                 425                 430
Asn Asn Tyr Lys Thr Thr Pro Pro Met Leu Asp Ser Asp Gly Ser Phe
        435                 440                 445
Phe Leu Tyr Ser Lys Leu Thr Val Asp Lys Ser Arg Trp Gln Gln Gly
    450                 455                 460
Asn Val Phe Ser Cys Ser Val Met His Glu Ala Leu His Asn His Tyr
465                 470                 475                 480
Thr Gln Lys Ser Leu Ser Leu Ser Pro Gly Lys
                485                 490

<210> SEQ ID NO 32
<211> LENGTH: 293
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

Met Leu Pro Gly Cys Lys Trp Asp Leu Leu Ile Lys Gln Trp Val Cys
1               5                   10                  15
Asp Pro Leu Gly Ser Gly Ser Ala Thr Gly Gly Ser Gly Ser Thr Ala
            20                  25                  30
Ser Ser Gly Ser Gly Ser Ala Thr His Met Leu Pro Gly Cys Lys Trp
        35                  40                  45
Asp Leu Leu Ile Lys Gln Trp Val Cys Asp Pro Leu Gly Gly Gly Gly
    50                  55                  60
Gly Val Asp Lys Thr His Thr Cys Pro Pro Cys Pro Ala Pro Glu Leu
```

```
              65                   70                  75                  80
Leu Gly Gly Pro Ser Val Phe Leu Phe Pro Pro Lys Pro Lys Asp Thr
             85                  90                  95

Leu Met Ile Ser Arg Thr Pro Glu Val Thr Cys Val Val Val Asp Val
            100                 105                 110

Ser His Glu Asp Pro Glu Val Lys Phe Asn Trp Tyr Val Asp Gly Val
            115                 120                 125

Glu Val His Asn Ala Lys Thr Lys Pro Arg Glu Glu Gln Tyr Asn Ser
        130                 135                 140

Thr Tyr Arg Val Val Ser Val Leu Thr Val Leu His Gln Asp Trp Leu
145                 150                 155                 160

Asn Gly Lys Glu Tyr Lys Cys Lys Val Ser Asn Lys Ala Leu Pro Ala
                165                 170                 175

Pro Ile Glu Lys Thr Ile Ser Lys Ala Lys Gly Gln Pro Arg Glu Pro
            180                 185                 190

Gln Val Tyr Thr Leu Pro Pro Ser Arg Asp Glu Leu Thr Lys Asn Gln
        195                 200                 205

Val Ser Leu Thr Cys Leu Val Lys Gly Phe Tyr Pro Ser Asp Ile Ala
210                 215                 220

Val Glu Trp Glu Ser Asn Gly Gln Pro Glu Asn Asn Tyr Lys Thr Thr
225                 230                 235                 240

Pro Pro Val Leu Asp Ser Asp Gly Ser Phe Phe Leu Tyr Ser Lys Leu
                245                 250                 255

Thr Val Asp Lys Ser Arg Trp Gln Gln Gly Asn Val Phe Ser Cys Ser
            260                 265                 270

Val Met His Glu Ala Leu His Asn His Tyr Thr Gln Lys Ser Leu Ser
        275                 280                 285

Leu Ser Pro Gly Lys
        290

<210> SEQ ID NO 33
<211> LENGTH: 232
<212> TYPE: PRT
<213> ORGANISM: Homo sapiens

<400> SEQUENCE: 33

Glu Pro Lys Ser Cys Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
    130                 135                 140
```

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
            165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
            195                 200                 205

Ser Cys Ser Val Met His Glu Ala Leu His Asn His Tyr Thr Gln Lys
            210                 215                 220

Ser Leu Ser Leu Ser Pro Gly Lys
225                 230

<210> SEQ ID NO 34
<211> LENGTH: 228
<212> TYPE: PRT
<213> ORGANISM: Homo sapiens

<400> SEQUENCE: 34

Glu Arg Lys Cys Cys Val Glu Cys Pro Pro Cys Pro Ala Pro Pro Val
1               5                   10                  15

Ala Gly Pro Ser Val Phe Leu Phe Pro Pro Lys Pro Lys Asp Thr Leu
            20                  25                  30

Met Ile Ser Arg Thr Pro Glu Val Thr Cys Val Val Val Asp Val Ser
            35                  40                  45

His Glu Asp Pro Glu Val Gln Phe Asn Trp Tyr Val Asp Gly Met Glu
        50                  55                  60

Val His Asn Ala Lys Thr Lys Pro Arg Glu Glu Gln Phe Asn Ser Thr
65                  70                  75                  80

Phe Arg Val Val Ser Val Leu Thr Val Val His Gln Asp Trp Leu Asn
                85                  90                  95

Gly Lys Glu Tyr Lys Cys Lys Val Ser Asn Lys Gly Leu Pro Ala Pro
            100                 105                 110

Ile Glu Lys Thr Ile Ser Lys Thr Lys Gly Gln Pro Arg Glu Pro Gln
            115                 120                 125

Val Tyr Thr Leu Pro Pro Ser Arg Glu Glu Met Thr Lys Asn Gln Val
130                 135                 140

Ser Leu Thr Cys Leu Val Lys Gly Phe Tyr Pro Ser Asp Ile Ala Val
145                 150                 155                 160

Glu Trp Glu Ser Asn Gly Gln Pro Glu Asn Asn Tyr Lys Thr Thr Pro
            165                 170                 175

Pro Met Leu Asp Ser Asp Gly Ser Phe Phe Leu Tyr Ser Lys Leu Thr
            180                 185                 190

Val Asp Lys Ser Arg Trp Gln Gln Gly Asn Val Phe Ser Cys Ser Val
            195                 200                 205

Met His Glu Ala Leu His Asn His Tyr Thr Gln Lys Ser Leu Ser Leu
            210                 215                 220

Ser Pro Gly Lys
225

<210> SEQ ID NO 35
<211> LENGTH: 279
<212> TYPE: PRT
<213> ORGANISM: Homo sapiens

<400> SEQUENCE: 35

```
Glu Leu Lys Thr Pro Leu Gly Asp Thr Thr His Thr Cys Pro Arg Cys
1               5                   10                  15

Pro Glu Pro Lys Ser Cys Asp Thr Pro Pro Cys Pro Arg Cys Pro
            20                  25                  30

Glu Pro Lys Ser Cys Asp Thr Pro Pro Cys Pro Arg Cys Pro Glu
            35                  40                  45

Pro Lys Ser Cys Asp Thr Pro Pro Cys Pro Arg Cys Pro Ala Pro
        50                  55                  60

Glu Leu Leu Gly Gly Pro Ser Val Phe Leu Phe Pro Pro Lys Pro Lys
65                  70                  75                  80

Asp Thr Leu Met Ile Ser Arg Thr Pro Glu Val Thr Cys Val Val Val
                85                  90                  95

Asp Val Ser His Glu Asp Pro Glu Val Gln Phe Lys Trp Tyr Val Asp
            100                 105                 110

Gly Val Glu Val His Asn Ala Lys Thr Lys Pro Arg Glu Glu Gln Tyr
        115                 120                 125

Asn Ser Thr Phe Arg Val Val Ser Val Leu Thr Val Leu His Gln Asp
        130                 135                 140

Trp Leu Asn Gly Lys Glu Tyr Lys Cys Lys Val Ser Asn Lys Ala Leu
145                 150                 155                 160

Pro Ala Pro Ile Glu Lys Thr Ile Ser Lys Thr Lys Gly Gln Pro Arg
                165                 170                 175

Glu Pro Gln Val Tyr Thr Leu Pro Pro Ser Arg Glu Glu Met Thr Lys
            180                 185                 190

Asn Gln Val Ser Leu Thr Cys Leu Val Lys Gly Phe Tyr Pro Ser Asp
        195                 200                 205

Ile Ala Val Glu Trp Glu Ser Ser Gly Gln Pro Glu Asn Asn Tyr Asn
210                 215                 220

Thr Thr Pro Pro Met Leu Asp Ser Asp Gly Ser Phe Phe Leu Tyr Ser
225                 230                 235                 240

Lys Leu Thr Val Asp Lys Ser Arg Trp Gln Gln Gly Asn Ile Phe Ser
                245                 250                 255

Cys Ser Val Met His Glu Ala Leu His Asn Arg Phe Thr Gln Lys Ser
            260                 265                 270

Leu Ser Leu Ser Pro Gly Lys
        275

<210> SEQ ID NO 36
<211> LENGTH: 229
<212> TYPE: PRT
<213> ORGANISM: Homo sapiens

<400> SEQUENCE: 36

Glu Ser Lys Tyr Gly Pro Pro Cys Pro Ser Cys Pro Ala Pro Glu Phe
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95
```

```
Asn Gly Lys Glu Tyr Lys Cys Lys Val Ser Asn Lys Gly Leu Pro Ser
                100                 105                 110

Ser Ile Glu Lys Thr Ile Ser Lys Ala Lys Gly Gln Pro Arg Glu Pro
            115                 120                 125

Gln Val Tyr Thr Leu Pro Pro Ser Gln Glu Met Thr Lys Asn Gln
        130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly Lys
225

<210> SEQ ID NO 37
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Gly Gly Gly Ser
1

<210> SEQ ID NO 38
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Gly Gly Gly Pro
1

<210> SEQ ID NO 39
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Gly Gly Gly Gln
1

<210> SEQ ID NO 40
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 40

Gly Gly Gly Gly Gly
1               5

<210> SEQ ID NO 41
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 41
ctgccgggtt gtaaatggga cctgctgatc aaacagtggg tttgtgaccc gctg            54

<210> SEQ ID NO 42
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 42
ggtggtggtg gt                                                          12

<210> SEQ ID NO 43
<211> LENGTH: 69
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (36)..(36)
<223> OTHER INFORMATION: a, c, t, g, unknown or other
<220> FEATURE:
<221> NAME/KEY: misc_feature
<222> LOCATION: (36)..(36)
<223> OTHER INFORMATION: n is a, c, g, or t

<400> SEQUENCE: 43
ggatccggtt ctgctactgg tggttccggc tccdbngcaa gctctggttc aggcagtgcg      60
actcatctg                                                              69

<210> SEQ ID NO 44
<211> LENGTH: 69
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 44
ggatccggtt ctgctactgg tggttccggc tccgtcgcaa gctctggttc aggcagtgcg      60
actcatctg                                                              69

<210> SEQ ID NO 45
<211> LENGTH: 69
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 45
```

```
ggatccggtt ctgctactgg tggttccggc tcctcggcaa gctctggttc aggcagtgcg    60
actcatctg                                                            69
```

<210> SEQ ID NO 46
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 46

```
cgggcgagtc agggtattag caactggtta gcc                                 33
```

<210> SEQ ID NO 47
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 47

```
cgggcgagtc agggtattag caactggtta gcc                                 33
```

<210> SEQ ID NO 48
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 48

```
caacagtatg atagttaccc tcggacg                                        27
```

<210> SEQ ID NO 49
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 49

```
agttattgga tgagt                                                     15
```

<210> SEQ ID NO 50
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 50

```
tacataaagc aagatggaaa tgagaaatac tatgtggact ctgtgaaggg c             51
```

<210> SEQ ID NO 51
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 51

```
gaagggatac tttggttcgg ggacttaccg acgttc                                36
```

<210> SEQ ID NO 52
<211> LENGTH: 324
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 52

```
gacatccaga tgacccagtc tccatcctca ctgtctgcat ctgtaggaga cagagtcacc         60
atcacttgtc gggcgagtca gggtattagc aactggttag cctggtatca gcagaaacca       120
gagaaagccc ctaagtccct gatctatgct gcatccagtt tgcaaagtgg ggtcccatca       180
aggttcagcg gcagtggatc tgggacagat ttcactctca ccatcagcag cctgcagcct       240
gaagattttg caacttatta ctgccaacag tatgatagtt accctcggac gttcggccaa       300
gggaccaagg tggaaatcaa acga                                              324
```

<210> SEQ ID NO 53
<211> LENGTH: 363
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 53

```
gaggtgcagc tggtggagtc tgggggaggc ttggtccagc ctgggggtc cctgagactc          60
tcctgtgcag cttctggatt tacctttagt agttattgga tgagttgggt ccgccaggct       120
ccagggaaag gctggagtg gtggcctac ataaagcaag atggaaatga gaaatactat         180
gtggactctg tgaagggccg attcaccatc tccagagaca acgccaagaa ctcattgtat       240
ctgcaaatga acagcctgag agccgaggac acggctgtgt attactgtgc gagggaaggg      300
atactttggt tcggggactt accgacgttc tggggccagg gaaccctggt caccgtctct      360
agt                                                                      363
```

<210> SEQ ID NO 54
<211> LENGTH: 1527
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 54

```
gaggtgcagc tggtggagtc tgggggaggc ttggtccagc ctgggggtc cctgagactc          60
tcctgtgcag cttctggatt tacctttagt agttattgga tgagttgggt ccgccaggct       120
ccagggaaag gctggagtg gtggcctac ataaagcaag atggaaatga gaaatactat         180
gtggactctg tgaagggccg attcaccatc tccagagaca acgccaagaa ctcattgtat       240
ctgcaaatga acagcctgag agccgaggac acggctgtgt attactgtgc gagggaaggg      300
atactttggt tcggggactt accgacgttc tggggccagg gaaccctggt caccgtctct      360
agtgcctcca ccaagggccc atcggtcttc cccctggcgc cctgctccag gagcacctcc      420
gagagcacag cggccctggg ctgcctggtc aaggactact tccccgaacc ggtgacggtg      480
```

```
tcgtggaact caggcgctct gaccagcggc gtgcacacct tcccagctgt cctacagtcc    540
tcaggactct actccctcag cagcgtggta acggtgccct cctcaaattt cgggacgcag    600
acatatacat gcaatgtgga tcataagcct tccaacacga aggtggacaa gactgtggag    660
cggaagtgtt gcgtcgagtg cccaccgtgt cccgctcctc cggtcgctgg cccatcagta    720
tttctcttcc ctcccaagcc aaaagataca ctcatgatct caagaacccc agaagtgact    780
tgtgtggtcg tggacgtgtc gcatgaggat ccggaggtgc agtttaactg gtatgtggat    840
ggcgtagaag tccacaacgc caagaccaag cctagagagg aacaattcaa ctcgacgttc    900
agggtggtca gcgtgttgac agtagtccac caggactggc ttaatgggaa ggaatacaaa    960
tgtaaggtct caaacaaagg gctcccggca cccattgaga agacaatttc caaaccaag   1020 ggacagccca gggaacccca agtgtatacg ctgcccccaa gccggaggag aatgacgaaa   1080
aatcaggtca gcctcacgtg tctcgtaaag ggattttacc cgtcggacat cgcggtggag   1140
tgggagtcaa atggacagcc cgaaaacaac tataagacca caccaccgat gctcgactcc   1200
gacggaagct tctttttgta ctcgaaactg acggtggaca atcgcgctg gcaacagggg   1260 aatgtcttta gctgctcggt catgcacgag gccctccaca atcattacac tcagaaaagc   1320
ttgtcgctct cgccgggtgg gggtggagga ctgcccggtt gcaaatggga tctgttgatc   1380
aaacagtggg tatgcgaccc tttgggaagc ggctcggcga cgggtgggtc ggggtcgggt   1440
gcgtccagcg gatcgggctc ggccactggg tcactccctg gatgcaagtg ggatcttctt   1500
atcaagcaat gggtgtgcga tccctc                                       1527

<210> SEQ ID NO 55
<211> LENGTH: 1533
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 55
gaggtgcagc tggtggagtc tgggggaggc ttggtccagc ctgggggtc cctgagactc     60 tcctgtgcag cttctggatt tacctttagt agttattgga tgagttgggt ccgccaggct    120
ccagggaaag gctgagtg gtggcctac ataaagcaag atggaaatga gaatactat       180 gtggactctg tgaagggccg attcaccatc tccagagaca cgccaagaa ctcattgtat    240 ctgcaaatga acagcctgag agccgaggac acggctgtgt attactgtgc gagggaaggg    300
atactttggt tcggggactt accgacgttc tggggccagg gaaccctggt caccgtctct    360
agtgcctcca ccaagggccc atcggtcttc cccctggcgc cctgctccag gagcacctcc    420
gagagcacag cggccctggg ctgcctggtc aaggactact ccccgaacc ggtgacggtg    480 tcgtggaact caggcgctct gaccagcggc gtgcacacct tcccagctgt cctacagtcc    540
tcaggactct actccctcag cagcgtggta acggtgccct cctcaaattt cgggacgcag    600
acatatacat gcaatgtgga tcataagcct tccaacacga aggtggacaa gactgtggag    660
cggaagtgtt gcgtcgagtg cccaccgtgt cccgctcctc cggtcgctgg cccatcagta    720
tttctcttcc ctcccaagcc aaaagataca ctcatgatct caagaacccc agaagtgact    780
tgtgtggtcg tggacgtgtc gcatgaggat ccggaggtgc agtttaactg gtatgtggat    840
ggcgtagaag tccacaacgc caagaccaag cctagagagg aacaattcaa ctcgacgttc    900
agggtggtca gcgtgttgac agtagtccac caggactggc ttaatgggaa ggaatacaaa    960
```

|  |  |
|---|---|
| tgtaaggtct caaacaaagg gctcccggca cccattgaga agacaatttc caaaaccaag | 1020 |
| ggacagccca gggaacccca agtgtatacg ctgcccccaa gccgggagga aatgacgaaa | 1080 |
| aatcaggtca gcctcacgtg tctcgtaaag ggattttacc cgtcggacat cgcggtggag | 1140 |
| tgggagtcaa atggacagcc cgaaaacaac tataagacca caccaccgat gctcgactcc | 1200 |
| gacggaagct tcttttgta ctcgaaactg acggtggaca aatcgcgctg gcaacagggg | 1260 |
| aatgtcttta gctgctcggt catgcacgag gccctccaca atcattacac tcagaaaagc | 1320 |
| ttgtcgctct cgccgggtaa aggtggtggt ggtggtctgc cggttgtaa atgggacctg | 1380 |
| ctgatcaaac agtgggtttg tgacccgctg ggatccggtt ctgctactgg tggttccggc | 1440 |
| tccgtcgcaa gctctggttc aggcagtgcg actcatctgc tgccgggttg taaatgggac | 1500 |
| ctgctgatca aacagtgggt tgtgacccg ctg | 1533 |

<210> SEQ ID NO 56
<211> LENGTH: 1533
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 56

|  |  |
|---|---|
| gaggtgcagc tggtggagtc tgggggaggc ttggtccagc ctgggggtc cctgagactc | 60 |
| tcctgtgcag cttctggatt taccttagt agttattgga tgagttgggt ccgccaggct | 120 |
| ccagggaaag gctggagtg gtggcctac ataaagcaag atggaaatga gaaatactat | 180 |
| gtggactctg tgaagggccg attcaccatc tccagagaca acgccaagaa ctcattgtat | 240 |
| ctgcaaatga acagcctgag agccgaggac acggctgtgt attactgtgc gagggaaggg | 300 |
| atactttggt tcgggactt accgacgttc tggggccagg gaaccctggt caccgtctct | 360 |
| agtgcctcca ccaagggccc atcggtcttc ccctggcgc cctgctccag gagcacctcc | 420 |
| gagagcacag cggccctggg ctgcctggtc aaggactact tccccgaacc ggtgacggtg | 480 |
| tcgtggaact caggcgctct gaccagcggc gtgcacacct tcccagctgt cctacagtcc | 540 |
| tcaggactct actccctcag cagcgtggta acggtgccct cctcaaattt cgggacgcag | 600 |
| acatatacat gcaatgtgga tcataagcct tccaacacga aggtggacaa gactgtggag | 660 |
| cggaagtgtt gcgtcgagtg cccaccgtgt cccgctcctc cggtcgctgg cccatcagta | 720 |
| tttctcttcc ctcccaagcc aaaagataca ctcatgatct caagaacccc agaagtgact | 780 |
| tgtgtggtcg tggacgtgtc gcatgaggat ccggaggtgc agtttaactg gtatgtggat | 840 |
| ggcgtagaag tccacaacgc caagaccaag cctagagagg aacaattcaa ctcgacgttc | 900 |
| agggtggtca gcgtgttgac agtagtccac caggactggc ttaatgggaa ggaatacaaa | 960 |
| tgtaaggtct caaacaaagg gctcccggca cccattgaga agacaatttc caaaaccaag | 1020 |
| ggacagccca gggaacccca agtgtatacg ctgcccccaa gccgggagga aatgacgaaa | 1080 |
| aatcaggtca gcctcacgtg tctcgtaaag ggattttacc cgtcggacat cgcggtggag | 1140 |
| tgggagtcaa atggacagcc cgaaaacaac tataagacca caccaccgat gctcgactcc | 1200 |
| gacggaagct tcttttgta ctcgaaactg acggtggaca aatcgcgctg gcaacagggg | 1260 |
| aatgtcttta gctgctcggt catgcacgag gccctccaca atcattacac tcagaaaagc | 1320 |
| ttgtcgctct cgccgggtaa aggtggtggt ggtggtctgc cggttgtaa atgggacctg | 1380 |
| ctgatcaaac agtgggtttg tgacccgctg ggatccggtt ctgctactgg tggttccggc | 1440 |

```
tcctcggcaa gctctggttc aggcagtgcg actcatctgc tgccgggttg taaatgggac    1500
ctgctgatca aacagtgggt ttgtgacccg ctg                                 1533
```

<210> SEQ ID NO 57
<211> LENGTH: 642
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 57

```
gacatccaga tgacccagtc tccatcctca ctgtctgcat ctgtaggaga cagagtcacc     60
atcacttgtc gggcgagtca gggtattagc aactggttag cctggtatca gcagaaacca    120
gagaaagccc ctaagtccct gatctatgct gcatccagtt tgcaaagtgg ggtcccatca    180
aggttcagcg gcagtggatc tgggacagat ttcactctca ccatcagcag cctgcagcct    240
gaagattttg caacttatta ctgccaacag tatgatagtt accctcggac gttcggccaa    300
gggaccaagg tggaaatcaa acgaactgtg gctgcaccat ctgtcttcat cttcccgcca    360
tctgatgagc agttgaaatc tggaactgcc tctgttgtgt gcctgctgaa taacttctat    420
cccagagagg ccaaagtaca gtggaaggtg gataacgccc tccaatcggg taactcccag    480
gagagtgtca cagagcagga cagcaaggac agcacctaca gcctcagcag caccctgacg    540
ctgagcaaag cagactacga gaaacacaaa gtctacgcct gcgaagtcac ccatcagggc    600
ctgagctcgc ccgtcacaaa gagcttcaac aggggagagt gt                       642
```

<210> SEQ ID NO 58
<211> LENGTH: 69
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 58

```
ggaagcggct cggcgacggg tgggtcgggg tcgggtgcgt ccagcggatc gggctcggcc     60
actgggtca                                                             69
```

<210> SEQ ID NO 59
<211> LENGTH: 1341
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (1332)..(1332)
<223> OTHER INFORMATION: a, c, t, g, unknown or other
<220> FEATURE:
<221> NAME/KEY: misc_feature
<222> LOCATION: (1332)..(1332)
<223> OTHER INFORMATION: n is a, c, g, or t

<400> SEQUENCE: 59

```
gaggtgcagc tggtggagtc tgggggaggc ttggtccagc ctggggggtc cctgagactc     60
tcctgtgcag cttctggatt tacctttagt agttattgga tgagttgggt ccgccaggct    120
ccagggaaag gctggagtg gtggcctac ataaagcaag atggaaatga gaaatactat      180
gtggactctg tgaagggccg attcaccatc tccagagaca acgccaagaa ctcattgtat    240
```

```
ctgcaaatga acagcctgag agccgaggac acggctgtgt attactgtgc gagggaaggg      300
atactttggt tcggggactt accgacgttc tggggccagg gaaccctggt caccgtctct      360
agtgcctcca ccaagggccc atcggtcttc cccctggcgc cctgctccag gagcacctcc      420
gagagcacag cggccctggg ctgcctggtc aaggactact ccccgaacc ggtgacggtg       480 tcgtggaact caggcgctct gaccagcggc gtgcacacct cccagctgt cctacagtcc       540 tcaggactct actccctcag cagcgtggta acggtgccct cctcaaattt cgggacgcag      600
acatatacat gcaatgtgga tcataagcct tccaacacga aggtggacaa gactgtggag      660
cggaagtgtt gcgtcgagtg cccaccgtgt cccgctcctc cggtcgctgg cccatcagta      720
tttctcttcc ctcccaagcc aaaagataca ctcatgatct caagaacccc agaagtgact      780
tgtgtggtcg tggacgtgtc gcatgaggat ccggaggtgc agtttaactg gtatgtggat      840
ggcgtagaag tccacaacgc caagaccaag cctagagagg aacaattcaa ctcgacgttc      900
agggtggtca gcgtgttgac agtagtccac caggactggc ttaatgggaa ggaatacaaa      960
tgtaaggtct caaacaaagg gctcccggca cccattgaga agacaatttc caaaaccaag     1020
ggacagccca gggaacccca agtgtatacg ctgcccccaa gccgggagga aatgacgaaa     1080
aatcaggtca gcctcacgtg tctcgtaaag ggatttttacc cgtcggacat cgcggtggag     1140
tgggagtcaa atggacagcc cgaaaacaac tataagacca caccaccgat gctcgactcc     1200
gacggaagct tcttttttgta ctcgaaactg acggtgaca atcgcgctg gcaacagggg      1260 aatgtcttta gctgctcggt catgcacgag gccctccaca atcattacac tcagaaaagc     1320
ttgtcgctct cnccgggtaa a                                                1341

<210> SEQ ID NO 60
<211> LENGTH: 1524
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 60 cttccccggat gcaagtggga tctgttgatc aagcaatggg tctgcgaccc tctcgggtca      60
gggtccgcga ccggtggatc ggggtcggga gcgtcatcgg gcagcggaag cgctacggga     120
tcacttcccg ggtgcaaatg ggacctcctg atcaaacaat gggtatgtga tccgctcggt     180
ggcgaggtgc agctggtgga gtctgggggga ggcttggtcc agcctggggg gtccctgaga     240
ctctcctgtg cagcttctgg atttacctt agtagttatt ggatgagttg gtccgccag       300 gctccaggga agggctggag gtgggtggcc tacataaagc aagatggaaa tgagaaatac     360
tatgtggact ctgtgaaggg ccgattcacc atctccagag acaacgccaa gaactcattg     420
tatctgcaaa tgaacagcct gagagccgag gacacggctg tgtattactg tgcgagggaa     480
gggatacttt ggttcgggga cttaccgacg ttctggggcc agggaaccct ggtcaccgtc     540
tctagtgcct ccaccaaggg cccatcggtc ttccccctgg cgcctgctc caggagcacc     600 tccgagagca gcggccct gggctgcctg gtcaaggact acttccccga accggtgacg     660
gtgtcgtgga actcaggcgc tctgaccagc ggcgtgcaca ccttcccagc tgtcctacag     720
tcctcaggac tctactccct cagcagcgtg gtgaccgtgc cctccagcaa cttcggcacc     780
cagacctaca cctgcaacgt agatcacaag cccagcaaca ccaaggtgga caagacagtt     840
gagcgcaaat gttgtgtcga gtgcccaccg tgcccagcac cacctgtggc aggaccgtca     900
```

| | |
|---|---|
| gtcttcctct tcccccaaa acccaaggac accctcatga tctcccggac ccctgaggtc | 960 |
| acgtgcgtgg tggtggacgt gagccacgaa gaccccgagg tccagttcaa ctggtacgtg | 1020 |
| gacggcgtgg aggtgcataa tgccaagaca aagccacggg aggagcagtt caacagcacg | 1080 |
| ttccgtgtgg tcagcgtcct caccgttgtg caccaggact ggctgaacgg caaggagtac | 1140 |
| aagtgcaagg tctccaacaa aggcctccca gcccccatcg agaaaaccat ctccaaaacc | 1200 |
| aaagggcagc cccgagaacc acaggtgtac accctgcccc catcccggga ggagatgacc | 1260 |
| aagaaccagg tcagcctgac ctgcctggtc aaaggcttct accccagcga catcgccgtg | 1320 |
| gagtgggaga gcaatgggca gccggagaac aactacaaga ccacacctcc catgctggac | 1380 |
| tccgacggct ccttcttcct ctacagcaag ctcaccgtgg acaagagcag gtggcagcag | 1440 |
| gggaacgtct tctcatgctc cgtgatgcat gaggctctgc acaaccacta cacgcagaag | 1500 |
| agcctctccc tgtctccggg taaa | 1524 |

<210> SEQ ID NO 61
<211> LENGTH: 825
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 61

| | |
|---|---|
| ctccctgggt gcaaatggga cctgttgatt aagcagtggg tctgcgaccc tctcggatcg | 60 |
| ggaagcgcaa ctgggggttc aggctcaggg gctagctccg gatcgggtc ggccacaggg | 120 |
| tcgctccccg gatgtaagtg ggaccttttg attaaacagt gggtgtgcga tccacttgga | 180 |
| ggtgatatcc agatgacaca gtcaccctcg tcgttgagcg ccagcgtggg agatagagtg | 240 |
| acgatcacct gtcgagccag ccagggcatc tccaactggc ttgcgtggta ccaacaaaag | 300 |
| cccgagaagg caccgaaatc gctgatctac gcggcgtcgt cactgcagtc gggtgtaccg | 360 |
| tcgcggttta gcgggtccgg gtccggaacg gacttcacgc tcacgatttc ctcattgcag | 420 |
| ccggaagatt ttgcgactta ttactgtcag caatatgact catatccccg cacattcggt | 480 |
| cagggaacca aggtcgagat caaacgtacg gtggctgcac catctgtctt catcttcccg | 540 |
| ccatctgatg agcagttgaa atctggaact gcctctgttg tgtgcctgct gaataacttc | 600 |
| tatcccagag aggccaaagt acagtggaag gtggataacg ccctccaatc gggtaactcc | 660 |
| caggagagtg tcacagagca ggacagcaag gacagcacct acagcctcag cagcaccctg | 720 |
| acgctgagca agcagacta cgagaaacac aaagtctacg cctgcgaagt cacccatcag | 780 |
| ggcctgagct cgcccgtcac aaagagcttc aacaggggag agtgt | 825 |

<210> SEQ ID NO 62
<211> LENGTH: 1533
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 62

| | |
|---|---|
| gaggtgcagc tggtggagtc tgggggaggc ttggtccagc ctggggggtc cctgagactc | 60 |
| tcctgtgcag cttctggatt tacctttagt agttattgga tgagttgggt ccgccaggct | 120 |
| ccagggaaag gctgagtg gtggcctac ataaagcaag atggaaatga aaatactat | 180 |
| gtggactctg tgaagggccg attcaccatc tccagagaca acgccaagaa ctcattgtat | 240 |

```
ctgcaaatga acagcctgag agccgaggac acggctgtgt attactgtgc gagggaaggg      300
atactttggt tcggggactt accgacgttc tggggccagg gaaccctggt caccgtctct      360
agtgcctcca ccaagggccc atcggtcttc cccctggcgc cctgctccag gagcacctcc      420
gagagcacag cggccctggg ctgcctggtc aaggactact ccccgaacc  ggtgacggtg      480 tcgtggaact caggcgctct gaccagcggc gtgcacacct tcccagctgt cctacagtcc      540
tcaggactct actccctcag cagcgtggta cggtgccct  cctcaaattt cgggacgcag      600
acatatacat gcaatgtgga tcataagcct tccaacacga aggtggacaa gactgtggag      660
cggaagtgtt gcgtcgagtg cccaccgtgt cccgctcctc cggtcgctgg cccatcagta      720
tttctcttcc ctcccaagcc aaaagataca ctcatgatct caagaacccc agaagtgact      780
tgtgtggtcg tggacgtgtc gcatgaggat ccggaggtgc agtttaactg gtatgtggat      840
ggcgtagaag tccacaacgc caagaccaag cctagagagg aacaattcaa ctcgacgttc      900
agggtggtca gcgtgttgac agtagtccac caggactggc ttaatgggaa ggaatacaaa      960
tgtaaggtct caaacaaagg gctcccggca cccattgaga agacaatttc caaaaccaag     1020
ggacagccca gggaacccca gtgtatacg  ctgccccccaa gccgggagga atgacgaaa     1080 aatcaggtca gcctcacgtg tctcgtaaag ggattttacc cgtcggacat cgcggtggag     1140
tgggagtcaa atggacagcc cgaaaacaac tacaaaacga ccccacctat gctcgattcg     1200
gacggcagct tcttttttgta ttcaaagttg acagtggaca aatcgcgatg gcagcagggc     1260
aacgtcttct catgttcagt aatgcatgag gcccttcaca accactacac gcagaagtcc     1320
ctctcattgt cgccgggtgg gggtggagga ctgcccgggt gcaagtggga cctcttgatc     1380
aaacagtggg tatgcgaccc tttgggaggg ggtgggtcag gaggggagg  ttccggtgga     1440 ggtggttccg ggggaggcgg atcaggaggt ggaggatcgt tgcccggctg taagtgggat     1500
ctgctgatca agcagtgggt ctgtgatcct ttg                                  1533
```

<210> SEQ ID NO 63
<211> LENGTH: 1530
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 63

```
gaggtgcagc tggtggagtc tgggggaggc ttggtccagc ctgggggtc  cctgagactc       60 tcctgtgcag cttctggatt tacctttagt agttattgga tgagttgggt ccgccaggct      120
ccagggaaag gctggagtg  ggtggcctac ataaagcaag atggaaatga gaaatactat      180
gtggactctg tgaagggccg attcaccatc tccagagaca acgccaagaa ctcattgtat      240
ctgcaaatga acagcctgag agccgaggac acggctgtgt attactgtgc gagggaaggg      300
atactttggt tcggggactt accgacgttc tggggccagg gaaccctggt caccgtctct      360
agtgcctcca ccaagggccc atcggtcttc cccctggcgc cctgctccag gagcacctcc      420
gagagcacag cggccctggg ctgcctggtc aaggactact ccccgaacc  ggtgacggtg      480 tcgtggaact caggcgctct gaccagcggc gtgcacacct tcccagctgt cctacagtcc      540
tcaggactct actccctcag cagcgtggtg accgtgccct ccagcaactt cggcacccag      600
acctacacct gcaacgtaga tcacaagccc agcaacacca aggtggacaa gacagttgag      660
cgcaaatgtt gtgtcgagtg cccaccgtgc ccagcaccac ctgtggcagg accgtcagtc      720
```

```
ttcctcttcc ccccaaaacc caaggacacc ctcatgatct cccggacccc tgaggtcacg    780
tgcgtggtgg tggacgtgag ccacgaagac cccgaggtcc agttcaactg gtacgtggac    840
ggcgtggagg tgcataatgc caagacaaag ccacgggagg agcagttcaa cagcacgttc    900
cgtgtggtca gcgtcctcac cgttgtgcac caggactggc tgaacggcaa ggagtacaag    960
tgcaaggtct ccaacaaagg cctcccagcc cccatcgaga aaccatctc caaaaccaaa    1020 gggcagcccc gagaaccaca ggtgtacacc ctgccaccttc gcggagga atgggagga    1080 ctccccgggt gcaagtggga tcttcttatc aaacagtggg tatgcgaccc gctggggtca    1140
gggtcagcga caggtggatc gggtagcggc gcatcgagcg gatcagggtc cgcgacgggc    1200
tcacttcccg gatgcaaatg ggacctcttg attaagcagt gggtgtgtga cccgttgggt    1260
ggaacgaaga atcaggtctc gttgacgtgt ctggtgaagg ggttttatcc ctcggatatc    1320
gctgtcgagt gggagtcgaa tggacagccc gaaaacaact acaagaccac cccgcctatg    1380
ctggactccg atggttcctt cttttttgtac tcgaaactga ctgtggataa gagcaggtgg    1440
cagcaaggga atgtattctc gtgttccgtc atgcacgaag ccctccataa ccactataca    1500
caaaaatcgc tttcacttag cccgggaaaa                                     1530

<210> SEQ ID NO 64
<211> LENGTH: 1470
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 64
gaggtgcagc tggtggagtc tgggggaggc ttggtccagc ctgggggggtc cctgagactc     60 tcctgtgcag cttctggatt tacctttagt agttattgga tgagttgggt ccgccaggct    120
ccagggaaag gctggagtg gtggcctac ataaagcaag atggaaatga gaaatactat    180
gtggactctg tgaagggccg attcaccatc tccagagaca acgccaagaa ctcattgtat    240
ctgcaaatga acagcctgag agccgaggac acggctgtgt attactgtgc gagggaaggg    300
atactttggt tcggggactt accgacgttc tggggccagg gaaccctggt caccgtctct    360
agtgcctcca ccaagggccc atcggtcttc cccctggcgc cctgctccag gagcacctcc    420
gagagcacag cggccctggg ctgcctggtc aaggactact ccccgaaccc ggtgacggtg    480
tcgtggaact caggcgctct gaccagcggc gtgcacaccct tcccagctgt cctacagtcc    540
tcaggactct actccctcag cagcgtggtg accgtgccct ccagcaactt cggcacccag    600
acctacacct gcaacgtaga tcacaagccc agcaacacca aggtggacaa gacagttgag    660
cgcaaatgtt gtgtcgagtg cccaccgtgc ccagcaccac ctgtggcagg accgtcagtc    720
ttcctcttcc ccccaaaacc caaggacacc ctcatgatct cccggacccc tgaggtcacg    780
tgcgtggtgg tggacgtgag ccacgaagac cccgaggtcc agttcaactg gtacgtggac    840
ggcgtggagg tgcataatgc caagacaaag ccacgggagg agcagttcaa cagcacgttc    900
cgtgtggtca gcgtcctcac cgttgtgcac caggactggc tgaacggcaa ggagtacaag    960
tgcaaggtct ccaacaaagg cctcccagcc cccatcgaga aaccatctc caaaaccaaa    1020 gggcagcccc gagaaccaca ggtgtacacc ctgccgccct cgagaagaa gatgggcggg    1080 ttgccggggt gtaagtggga cttgctgatt aaacaatggg tgtgcgaccc tctgggcggt    1140
accaagaatc aggtctcact gacatgtctc gtaaaaggtt tttacccgtc agatatcgcg    1200
```

```
gtcgagtggg aatccaacgg acaacccgag aataactaca agacgactcc cccaatgctc    1260
gattcggatg gatccttctt cctttatagc aaacttacag tagacaaatc acggtggcag    1320
caggggaacg tgtttagctg ttcggtgatg cacgaagcct tgcataatca ctatacgcag    1380
aagtcgcttt ccctgtcgcc gggagggga ggtgggctcc ctggatgcaa gtgggatctt    1440
ttgatcaagc agtgggtctg cgaccccctc                                     1470
```

<210> SEQ ID NO 65
<211> LENGTH: 1473
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 65

```
gaggtgcagc tggtggagtc tgggggaggc ttggtccagc ctggggggtc cctgagactc     60
tcctgtgcag cttctggatt tacctttagt agttattgga tgagttgggt ccgccaggct    120
ccagggaaag gctggagtg gtggcctac ataaagcaag atggaaatga gaaatactat     180
gtggactctg tgaagggccg attccaccatc tccagagaca acgccaagaa ctcattgtat    240
ctgcaaatga acagcctgag agccgaggac acggctgtgt attactgtgc gagggaaggg    300
atactttggt tcggggactt accgacgttc tggggccagg gaaccctggt caccgtctct    360
agtgcctcca ccaagggccc atcggtcttc cccctggcgc cctgctccag gagcacctcc    420
gagagcacac ggccctggg ctgcctggtc aaggactact cccccgaacc ggtgacggtg    480
tcgtggaact caggcgctct gaccagcggc gtgcacacct tcccagctgt cctacagtcc    540
tcaggactct actccctcag cagcgtggtg accgtgccct ccagcaactt cggcacccag    600
acctacacct gcaacgtaga tcacaagccc agcaacacca aggtggacaa gacagttgag    660
cgcaaatgtt gtgtcgagtg cccaccgtgc ccagcaccac ctgtggcagg accgtcagtc    720
ttcctcttcc ccccaaaacc caaggacacc ctcatgatct cccggacccc tgaggtcacg    780
tgcgtggtgg tggatgtaag ccatggggga ctgcctggat gcaagtggga tcttctcatt    840
aagcaatggg tctgtgaccc tttgggcgga gaggacccgg aagtccagtt caactggtac    900
gtggacggcg tggaggtgca taatgccaag acaaagccac gggaggagca gttcaacagc    960
acgttccgtg tggtcagcgt cctcaccgtt gtgcaccagg actggctgaa cggcaaggag   1020
tacaagtgca aggtctccaa caaaggcctc ccagcccca tcgagaaaac catctccaaa   1080
accaaagggc agccccgaga accacaggtg tacaccctgc cgccctcgag agaagagatg   1140
ggcgggttgc cggggtgtaa gtgggacttg ctgattaaac aatgggtgtg cgaccctctg   1200
ggcggtacca agaatcaggt ctcactgaca tgtctcgtaa aaggttttta cccgtcagat   1260
atcgcggtcg agtgggaatc caacggacaa cccgagaata actacaagac gactccccca   1320
atgctcgatt cggatggatc cttcttcctt tatagcaaac ttacagtaga caaatcacgg   1380
tggcagcagg ggaacgtgtt tagctgttcg gtgatgcacg aagccttgca taatcactat   1440
acgcagaagt cgctttccct gtctccgggt aaa                                1473
```

<210> SEQ ID NO 66
<211> LENGTH: 879
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 66

```
atgcttccag gttgtaaatg ggatcttctt attaaacaat gggtttgtga tccacttggt      60
tctggttctg ctactggtgg ttccggctcc accgcaagct ctggttcagg ttctgctact     120
catatgctgc cggggttgtaa atgggacctg ctgatcaaac agtgggtttg tgacccgctg    180
ggtggaggcg gtggggtcga caaaactcac acatgtccac cttgtccagc tccgaactc     240
ctgggggac cgtcagtctt cctcttcccc ccaaaaccca aggacaccct catgatctcc      300
cggacccctg aggtcacatg cgtggtggtg gacgtgagcc acgaagaccc tgaggtcaag     360
ttcaactggt acgtggacgg cgtggaggtg cataatgcca agacaaagcc gcgggaggag     420
cagtacaaca gcacgtaccg tgtggtcagc gtcctcaccg tcctgcacca ggactggctg     480
aatggcaagg agtacaagtg caaggtctcc aacaaagccc tcccagcccc catcgagaaa    540
accatctcca agccaaagg gcagccccga gaaccacagg tgtacaccct gcccccatcc     600
cgggatgagc tgaccaagaa ccaggtcagc ctgacctgcc tggtcaaagg cttctatccc     660
agcgacatcg ccgtggagtg ggagagcaat gggcagccgg agaacaacta caagaccacg    720
cctcccgtgc tggactccga cggctccttc ttcctctaca gcaagctcac cgtggacaag     780
agcaggtggc agcaggggaa cgtcttctca tgctccgtga tgcatgaggc tctgcacaac    840
cactacacgc agaagagcct ctccctgtct ccgggtaaa                            879
```

<210> SEQ ID NO 67
<211> LENGTH: 696
<212> TYPE: DNA
<213> ORGANISM: Homo sapiens

<400> SEQUENCE: 67

```
gagcccaaat cttgtgacaa aactcacaca tgcccaccgt gcccagcacc tgaactcctg      60
gggggaccgt cagtcttcct cttccccca aaacccaagg acaccctcat gatctcccgg     120
accccctgagg tcacatgcgt ggtggtggac gtgagccacg aagaccctga ggtcaagttc     180
aactggtacg tggacggcgt ggaggtgcat aatgccaaga caaagccgcg ggaggagcag    240
tacaacagca cgtaccgtgt ggtcagcgtc ctcaccgtcc tgcaccagga ctggctgaat    300
ggcaaggagt acaagtgcaa ggtctccaac aaagccctcc cagcccccat cgagaaaacc    360
atctccaaag ccaaagggca gccccgagaa ccacaggtgt acaccctgcc ccatcccgg     420
gatgagctga ccaagaacca ggtcagcctg acctgcctgg tcaaaggctt ctatcccagc    480
gacatcgccg tggagtggga gagcaatggg cagccggaga caactacaa gaccacgcct     540
cccgtgctgg actccgacgg ctccttcttc tctatagca agctcaccgt ggacaagagc    600
aggtggcagc aggggaacgt cttctcatgc tccgtgatgc atgaggctct gcacaaccac    660
tacacgcaga agagcctctc cctgtctccg ggtaaa                               696
```

<210> SEQ ID NO 68
<211> LENGTH: 684
<212> TYPE: DNA
<213> ORGANISM: Homo sapiens

<400> SEQUENCE: 68

```
gagcgcaaat gttgtgtcga gtgcccaccg tgcccagcac cacctgtggc aggaccgtca     60
gtcttcctct tccccccaaa acccaaggac accctcatga tctcccggac ccctgaggtc    120
acgtgcgtgg tggtggacgt gagccacgaa gaccccgagg tccagttcaa ctggtacgtg    180
```

```
gacggcgtgg aggtgcataa tgccaagaca agccacggg aggagcagtt caacagcacg    240
ttccgtgtgg tcagcgtcct caccgttgtg caccaggact ggctgaacgg caaggagtac    300
aagtgcaagg tctccaacaa aggcctccca gcccccatcg agaaaaccat ctccaaaacc    360
aaagggcagc cccgagaacc acaggtgtac accctgcccc catcccggga ggagatgacc    420
aagaaccagg tcagcctgac ctgcctggtc aaaggcttct accccagcga catcgccgtg    480
gagtgggaga gcaatgggca gccggagaac aactacaaga ccacacctcc catgctggac    540
tccgacggct ccttcttcct ctacagcaag ctcaccgtgg acaagagcag gtggcagcag    600
gggaacgtct tctcatgctc cgtgatgcat gaggctctgc acaaccacta cacgcagaag    660
agcctctccc tgtctccggg taaa                                           684
```

<210> SEQ ID NO 69
<211> LENGTH: 837
<212> TYPE: DNA
<213> ORGANISM: Homo sapiens

<400> SEQUENCE: 69

```
gagctcaaaa ccccacttgg tgacacaact cacacatgcc cacggtgccc agagcccaaa     60
tcttgtgaca cacctccccc gtgcccacgg tgcccagagc ccaaatcttg tgacacacct    120
cccccgtgcc cacggtgccc agagcccaaa tcttgtgaca cacctccccc atgcccacgg    180
tgcccagcac ctgaactcct ggaggaccg tcagtcttcc tcttcccccc aaaacccaag     240 gatacccctta tgatttcccg gaccctgag gtcacgtgcg tggtggtgga cgtgagccac    300 gaagacccg aggtccagtt caagtggtac gtggacggcg tggaggtgca taatgccaag    360
acaaagccgc gggaggagca gttcaacagc acgttccgtg tggtcagcgt cctcaccgtc    420
ctgcaccagg actggctgaa cggcaaggag tacaagtgca aggtctccaa caaagccctc    480
ccagccccca tcgagaaaac catctccaaa accaaaggac agccccgaga accacaggtg    540
tacaccctgc ccccatcccg ggaggagatg accaagaacc aggtcagcct gacctgcctg    600
gtcaaaggct tctaccccag cgacatcgcc gtggagtggg agagcagcgg gcagccggag    660
aacaactaca acaccacgcc tcccatgctg gactccgacg gctccttctt cctctacagc    720
aagctcaccg tggacaagag caggtggcag caggggaaca tcttctcatg ctccgtgatg    780
catgaggctc tgcacaaccg cttcacgcag aagagcctct ccctgtctcc gggtaaa       837
```

<210> SEQ ID NO 70
<211> LENGTH: 687
<212> TYPE: DNA
<213> ORGANISM: Homo sapiens

<400> SEQUENCE: 70

```
gagtccaaat atggtccccc atgcccatca tgcccagcac ctgagttcct ggggggacca     60
tcagtcttcc tgttcccccc aaaacccaag gacactctca tgatctcccg gacccctgag    120
gtcacgtgcg tggtggtgga cgtgagccag gaagaccccg aggtccagtt caactggtac    180
gtggatggcg tggaggtgca taatgccaag acaaagccgc gggaggagca gttcaacagc    240
acgtaccgtg tggtcagcgt cctcaccgtc ctgcaccagg actggctgaa cggcaaggag    300
tacaagtgca aggtctccaa caaaggcctc ccgtcctcca tcgagaaaac catctccaaa    360
gccaaagggc agccccgaga gccacaggtg tacaccctgc ccccatccca ggaggagatg    420
accaagaacc aggtcagcct gacctgcctg gtcaaaggct tctaccccag cgacatcgcc    480
```

```
gtggagtggg agagcaatgg gcagccggag aacaactaca agaccacgcc tcccgtgctg    540
gactccgacg gctccttctt cctctacagc aggctaaccg tgracaagag caggtggcag    600
gaggggaatg tcttctcatg ctccgtgakg catgaggctc tgcacaacca ctacacacag    660
aagagcctct ccctgtctct gggtaaa                                        687
```

<210> SEQ ID NO 71
<211> LENGTH: 25
<212> TYPE: PRT
<213> ORGANISM: Artificial Sequence
<220> FEATURE:
<223> OTHER INFORMATION: Description of Artificial Sequence: Synthetic peptide

<400> SEQUENCE: 71

```
Gly Gly Gly Gly Ser Gly Gly Gly Gly Ser Gly Gly Gly Gly Ser Gly
1               5                   10                  15

Gly Gly Gly Ser Gly Gly Gly Gly Ser
            20                  25
```

PROTEINS SPECIFIC FOR BAFF AND B7RP1

PRIORITY

This application claims the benefit of U.S. Provisional Patent Application 61/780,260, filed Mar. 13, 2013, the contents of which are incorporated herein by reference in their entirety.

SEQUENCE LISTING

The instant application contains a Sequence Listing which has been submitted electronically in ASCII format and is hereby incorporated by reference in its entirety. Said ASCII copy, created on Feb. 19, 2014, is named A-1808-US-NP_SL.txt and is 95,780 bytes in size.

FIELD

The bispecific molecules described herein are within the field of protein therapeutics.

BACKGROUND

Most therapeutic proteins bind to a single target protein with high specificity, thereby interfering with the activity of this single target protein. That protein may be a part of one or more biological pathways that mediate a human disease being treated, and the therapeutic protein may therefore inhibit disease progression. However, efficacy of therapeutic proteins is rarely complete for all patients. Incomplete efficacy of therapeutic proteins could be due in some cases to the complexity of a disease. For example, some diseases may be mediated by multiple biological pathways, or different biological pathways may play a predominant role in mediating disease activity in different patients having the same clinically-defined condition. Hence, in some diseases it may be advantageous to simultaneously inhibit at least two biological pathways.

SUMMARY

Herein is provided a bispecific protein that can bind to and inhibit the biological activity of both B7RP1 and BAFF. BAFF plays a role in B cell survival, and B7RP1 plays a role in T cell costimulation. Thus, a protein that inhibits the activity of both proteins interferes with the activity of both B and T cells.

Described herein is bispecific protein, wherein the protein can inhibit BAFF-mediated proliferation of human B cells and wherein the protein can inhibit B7RP1-mediated proliferation of human T cells. The bispecific protein can comprise an IgG antibody comprising two immunoglobulin heavy chains having different amino acid sequences and two immunoglobulin light chains having different amino acid sequences. The IgG antibody can inhibit BAFF-mediated proliferation of human B cells and B7RP1-mediated proliferation of human T cells The IgG antibody can be an IgG1, IgG2, IgG3, or IgG4 antibody and can be a human or humanized IgG antibody. The bispecific protein can comprise a light chain complementarity determining region 1 (CDR1) comprising the amino acid sequence of SEQ ID NO:8, a light chain complementarity determining region 2 (CDR2) comprising the amino acid sequence of SEQ ID NO:9, a light chain complementarity determining region 3 (CDR3) comprising the amino acid sequence of SEQ ID NO:10, a heavy chain CDR1 comprising the amino acid sequence of SEQ ID NO:11, a heavy chain CDR2 comprising the amino acid sequence of SEQ ID NO:12, and a heavy chain CDR3 comprising the amino acid sequence of SEQ ID NO:13. Further, the bispecific protein can comprise a heavy chain variable region comprising SEQ ID NO:15 or a variant thereof and a light chain variable region comprising SEQ ID NO:14 or a variant thereof. Such variant sequences can comprise not more than 10 deletions, insertions of substitutions of a single amino acid per 100 amino acids relative to a reference sequence.

In an alternate embodiment, a bispecific protein that can inhibit BAFF-mediated proliferation of human B cells and that can inhibit B7RP1-mediated proliferation of human T cells can comprise: (a) a polypeptide comprising an amino acid sequence having the following formula: A-L1-P-L2-P, wherein A is an immunoglobulin heavy chain of an IgG antibody, L1 is a first linker of that is absent or is 3 to 40 amino acids long, P is a BAFF-binding peptide that is 10 to 40 amino acids long, and L2 is a peptide linker that is absent or is 5 to 50 amino acids long; and (b) an immunoglobulin light chain. The immunoglobulin heavy chain of (a) and the immunoglobulin light chain of (b) can form an IgG antibody that can bind B7RP1 and/or can inhibit B7RP1-mediated proliferation of human T cells. The immunoglobulin heavy chain may be missing a lysine at its C-terminal end just upstream of L1. The IgG antibody can be a human or humanized IgG1, IgG2, IgG3, or IgG4 antibody. The BAFF-binding peptide P can have the amino acid sequence of SEQ ID NO:1, SEQ ID NO:2, or SEQ ID NO:3. L1 can have the amino acid sequence of SEQ ID NO:4, 43, 45, or 46. L2 can have the amino acid sequence of SEQ ID NO:5, 6, or 7. The bispecific protein can comprise a light chain CDR1 comprising the amino acid sequence of SEQ ID NO:8 (RASQ-GISNWLA), a light chain CDR2 comprising the amino acid sequence of SEQ ID NO:9 (AASSLQS), a light chain CDR3 comprising the amino acid sequence of SEQ ID NO:10 (QQYDSYPRT), a heavy chain CDR1 comprising the amino acid sequence of SEQ ID NO:11 (SYWMS), a heavy chain CDR2 comprising the amino acid sequence of SEQ ID NO:12 (YIKQDGNEKYYVDSVKG), and a heavy chain CDR3 comprising the amino acid sequence of SEQ ID NO:13 (EGILWFGDLPTF). The bispecific protein can comprise an immunoglobulin light chain variable region comprising the amino acid sequence of SEQ ID NO:14 and/or an immunoglobulin heavy chain variable region comprising the amino acid sequence of SEQ ID NO:15. The bispecific protein can comprise the amino acid sequence of SEQ ID NO:19 or a variant thereof and the amino acid sequence of SEQ ID NO:17 or 18 or variants thereof. Such variant sequences can comprise not more than 10 deletions, insertions of substitutions of a single amino acid per 100 amino acids relative to the reference sequence.

In a further aspect, herein is described a bispecific protein comprising: (a) a polypeptide comprising the amino acid sequence of SEQ ID NO:17 or SEQ ID NO:18 or variants thereof; and (b) another polypeptide comprising the amino acid sequence of SEQ ID NO:19 or a variant thereof. Such variant sequences can comprise not more than 10 deletions, insertions of substitutions of a single amino acid per 100 amino acids relative to the reference sequence. The bispecific protein can inhibit BAFF-mediated proliferation of human B cells and B7RP1-mediated proliferation of human T cells. The bispecific protein can be a tetramer comprising two molecules of the polypeptide of (a) and two molecules of the polypeptide of (b).

In another embodiment, herein is provided a protein comprising a linker comprising the amino acid sequence of SEQ DI NO:6 or SEQ ID NO:7.

Further, herein is described a pharmaceutical composition comprising any of the bispecific proteins herein described or the protein comprising the amino acid sequence of SEQ ID NO:6 or 7 and a physiologically acceptable excipient.

Also described herein is a nucleic acid encoding any polypeptide included in one of bispecific proteins herein described. Exemplary nucleic acids encoding a polypeptide included in a bispecific protein include, for example, SEQ ID NOs: 60, 61, 62, and 63, among others. Vectors comprising such nucleic acids and host cells containing such vectors and/or nucleic acids are described. Further described herein is method for making a bispecific protein comprising culturing the host cell containing a nucleic acid encoding any of the bispecific proteins described herein under conditions such that the nucleic acid is expressed and recovering the protein from the cell mass or the culture medium. The host cell can be a mammalian cell, for example, a CHO cell, or a bacterial cell such as *Eschericha coli*.

In another aspect, described herein is a method for treating systemic lupus erythematosus comprising administering to a patient a therapeutically effective amount of any of the bispecific proteins described herein or a pharmaceutical composition comprising such a bispecific protein. Another therapeutic can be administered to the patient before, after, or concurrently with the bispecific protein. The other therapeutic can be a corticosteroid, an antimalarial, retinoic acid, an NSAID, cyclophosphamide, dehydroepiandrosterone, mycophenolate mofetil, azathioprine, chlorambucil, methotrexate, tacrolimus, dapsone, thalidomide, leflunomide, or cyclosporine.

In a further aspect, herein is described a method of treatment comprising administering to a patient a therapeutically effective amount of any of the bispecific proteins described herein or a pharmaceutical composition comprising a bispecific protein described herein, wherein the patient has a disease selected from the group consisting of: ANCA-positive vasculitis, rheumatoid arthritis (RA), Crohn's disease, ulcerative colitis, celiac disease, pemphigus, pemphigoid, subacute cutaneous lupus erythematosus (SCLE), multiple sclerosis, chronic inflammatory demyelinating polyneuropathy (CIDP), myasthenia gravis, Goodpasture's syndrome, glomerulonephritis, autoimmune hemolytic anemia (AIHA), idiopathic thrombocytopenic purpura (ITP), chronic active hepatitis, primary billiary cirrhosis, Sjogren's syndrome, systemic sclerosis, Hashimoto's thyroiditis, Graves' disease, Addison's disease, and multiple endocrine neoplasia (MEN).

In another aspect, herein is described a pharmaceutical composition comprising any of the bispecific protein herein described. The pharmaceutical composition can be for the treatment of systemic lupus erythematosus or lupus nephritis.

In another aspect, the use of any of the bispecific proteins provided herein as a medicament is described.

BRIEF DESCRIPTION OF THE SEQUENCE LISTINGS

Figure 1:
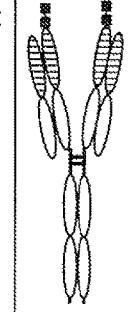
FIG. 1: Diagrams of bispecific proteins that bind to BAFF and B7RP1. Across the top row are listed the identifier for each construct. Across the second row is a brief descriptive phrase relating to the structure of each construct. Across the bottom row is a diagram of the structure of each construct. The blue ovals represent constant regions of an immunoglobulin heavy or light chain. The green ovals represent immunoglobulin heavy or light chain variable (VH or VL) regions. The small red squares and the orange loops represent BAFF-binding peptides.
Figure 1:
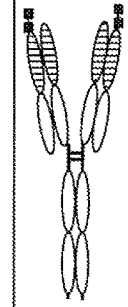
Figure 1:
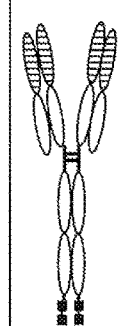
Figure 1:
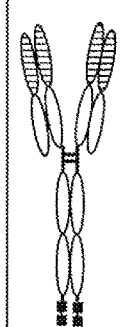
Figure 1:
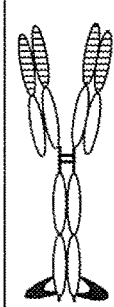
Figure 1:
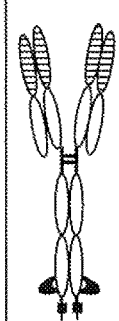
Figure 1:
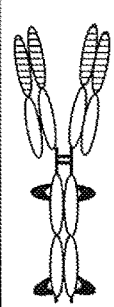

| SEQUENCE LISTING NUMBER | DESCRIPTION |
| --- | --- |
| SEQ ID NO: 1 | Amino acid sequence of a BAFF-binding peptide |
| SEQ ID NO: 2 | Amino acid sequence of a BAFF-binding peptide |
| SEQ ID NO: 3 | Amino acid sequence of a BAFF-binding peptide |
| SEQ ID NO: 4 | Amino acid sequence of a linker |
| SEQ ID NO: 5 | Amino acid sequence of a linker |
| SEQ ID NO: 6 | Amino acid sequence of a linker |
| SEQ ID NO: 7 | Amino acid sequence of a linker |
| SEQ ID NO: 8 | Amino acid sequence of a light chain CDR1 |
| SEQ ID NO: 9 | Amino acid sequence of a light chain CDR2 |
| SEQ ID NO: 10 | Amino acid sequence of a light chain CDR3 |
| SEQ ID NO: 11 | Amino acid sequence of a heavy chain CDR1 |
| SEQ ID NO: 12 | Amino acid sequence of a heavy chain CDR2 |
| SEQ ID NO: 13 | Amino acid sequence of a heavy chain CDR3 |
| SEQ ID NO: 14 | Amino acid sequence of a light chain variable region |
| SEQ ID NO: 15 | Amino acid sequence of a heavy chain variable region |
| SEQ ID NO: 16 | Amino acid sequence of a heavy chain of a BAFF/B7RP1 bispecific molecule |
| SEQ ID NO: 17 | Amino acid sequence of a heavy chain of a BAFF/B7RP1 bispecific molecule |
| SEQ ID NO: 18 | Amino acid sequence of a heavy chain of a BAFF/B7RP1 bispecific molecule |
| SEQ ID NO: 19 | Amino acid sequence of the immunoglobulin light chain of an IgG anti-huB7RP1 antibody |
| SEQ ID NO: 20 | Amino acid sequence preceding a heavy chain CDR1 |
| SEQ ID NO: 21 | Amino acid sequence preceding a heavy chain CDR2 |
| SEQ ID NO: 22 | Amino acid sequence following heavy chain CDR3 |
| SEQ ID NO: 23 | Amino acid sequence following light chain CDR3 |
| SEQ ID NO: 24 | Linker |
| SEQ ID NO: 25 | Amino acid sequence of the immunoglobulin heavy chain of an anti-B7RP1 IgG antibody |
| SEQ ID NO: 26 | Amino acid sequence of heavy chain of construct P71617 |
| SEQ ID NO: 27 | Amino acid sequence of light chain of construct P71618 |
| SEQ ID NO: 28 | Amino acid sequence of heavy chain of construct P71620 |
| SEQ ID NO: 29 | Amino acid sequence of the heavy chain of the P71621 construct |
| SEQ ID NO: 30 | Amino acid sequence of the heavy chain of construct P71622 |
| SEQ ID NO: 31 | Amino acid sequence of the heavy chain of construct P71623 |
| SEQ ID NO: 32 | Amino acid sequence of αBAFF peptibody |
| SEQ ID NO: 33 | Amino acid sequence of human IgG1 Fc region |
| SEQ ID NO: 34 | Amino acid sequence of human IgG2 Fc region |
| SEQ ID NO: 35 | Amino acid sequence of human IgG3 Fc region |
| SEQ ID NO: 36 | Amino acid sequence of human IgG4 Fc region |
| SEQ ID NO: 37 | Amino acid sequence of a linker |
| SEQ ID NO: 38 | Amino acid sequence of a linker |
| SEQ ID NO: 39 | Amino acid sequence of a linker |
| SEQ ID NO: 40 | Amino acid sequence of a linker |
| SEQ ID NO: 41 | Nucleic acid sequence encoding the amino acid sequence of SEQ ID NO: 1 |
| SEQ ID NO: 42 | Nucleic acid sequence encoding the amino acid sequence of SEQ ID NO: 4 |
| SEQ ID NO: 43 | Nucleic acid sequence encoding the amino acid sequence of SEQ ID NO: 5 |
| SEQ ID NO: 44 | Nucleic acid sequence encoding the amino acid sequence of SEQ ID NO: 6 |
| SEQ ID NO: 45 | Nucleic acid sequence encoding the amino acid sequence of SEQ ID NO: 7 |
| SEQ ID NO: 46 | Nucleic acid sequence encoding the amino acid sequence of SEQ ID NO: 8 |
| SEQ ID NO: 47 | Nucleic acid sequence encoding the amino acid sequence of SEQ ID NO: 9 |
| SEQ ID NO: 48 | Nucleic acid sequence encoding the amino acid sequence of SEQ ID NO: 10 |
| SEQ ID NO: 49 | Nucleic acid sequence encoding the amino acid sequence of SEQ ID NO: 11 |

| SEQUENCE LISTING NUMBER | DESCRIPTION |
|---|---|
| SEQ ID NO: 50 | Nucleic acid sequence encoding the amino acid sequence of SEQ ID NO: 12 |
| SEQ ID NO: 51 | Nucleic acid sequence encoding the amino acid sequence of SEQ ID NO: 13 |
| SEQ ID NO: 52 | Nucleic acid sequence encoding the amino acid sequence of SEQ ID NO: 14 |
| SEQ ID NO: 53 | Nucleic acid sequence encoding the amino acid sequence of SEQ ID NO: 15 |
| SEQ ID NO: 54 | Nucleic acid sequence encoding the amino acid sequence of SEQ ID NO: 16 |
| SEQ ID NO: 55 | Nucleic acid sequence encoding the amino acid sequence of SEQ ID NO: 17 |
| SEQ ID NO: 56 | Nucleic acid sequence encoding the amino acid sequence of SEQ ID NO: 18 |
| SEQ ID NO: 57 | Nucleic acid sequence encoding the amino acid sequence of SEQ ID NO: 19 |
| SEQ ID NO: 58 | Nucleic acid sequence encoding the amino acid sequence of SEQ ID NO: 24 |
| SEQ ID NO: 59 | Nucleic acid sequence encoding the amino acid sequence of SEQ ID NO: 25 |
| SEQ ID NO: 60 | Nucleic acid sequence encoding the amino acid sequence of SEQ ID NO: 26 |
| SEQ ID NO: 61 | Nucleic acid sequence encoding the amino acid sequence of SEQ ID NO: 27 |
| SEQ ID NO: 62 | Nucleic acid sequence encoding the amino acid sequence of SEQ ID NO: 28 |
| SEQ ID NO: 63 | Nucleic acid sequence encoding the amino acid sequence of SEQ ID NO: 29 |
| SEQ ID NO: 64 | Nucleic acid sequence encoding the amino acid sequence of SEQ ID NO: 30 |
| SEQ ID NO: 65 | Nucleic acid sequence encoding the amino acid sequence of SEQ ID NO: 31 |
| SEQ ID NO: 66 | Nucleic acid sequence encoding the amino acid sequence of SEQ ID NO: 32 |
| SEQ ID NO: 67 | Nucleic acid sequence encoding the amino acid sequence of SEQ ID NO: 33 |
| SEQ ID NO: 68 | Nucleic acid sequence encoding the amino acid sequence of SEQ ID NO: 34 |
| SEQ ID NO: 69 | Nucleic acid sequence encoding the amino acid sequence of SEQ ID NO: 35 |
| SEQ ID NO: 70 | Nucleic acid sequence encoding the amino acid sequence of SEQ ID NO: 36 |
| SEQ ID NO: 71 | Amino acid sequence of a linker |

DETAILED DESCRIPTION

Provided herein are bispecific proteins that bind to and inhibit both B cell activating factor (BAFF; also known as BLYS, TALL1, THANK, or TNFSF13B) and B7-related protein 1 (B7RP1; also known as ICOS Ligand, ICOSL, LICOS, B7 Homolog 2, B7H2, and GL50), nucleic acids encoding these bispecific proteins, and methods of making and using these proteins. The bispecific proteins can inhibit both BAFF-mediated B proliferation and B7RP1-mediated T cell proliferation. In another aspect, the bispecific proteins can inhibit B7RP1 binding to T cells. Such a bispecific protein can be an IgG antibody comprising two different immunoglobulin heavy chains and two different immunoglobulin light chains, where one heavy chain/light chain pair binds to BAFF and the other binds to B7RP1. Alternatively, the B7RP1-binding portion of the bispecific protein can comprise an IgG antibody including two identical heavy chains and two identical light chains, and the BAFF-binding portion of the bispecific protein can comprise one or more BAFF-binding peptides, which can be fused to the anti-B7RP1 antibody, optionally via the N-terminus of the immunoglobulin heavy or light chain, the carboxyterminus of the immunoglobulin heavy chain, and/or within the CH2 and/or CH3 region of the immunoglobulin heavy chain.

Definitions

An "antibody," as meant herein, is a protein comprising a heavy and/or light chain immunoglobulin variable region.

A "bispecific" protein, as meant herein is a protein that can bind specifically to two different molecules, which, in some embodiments, are proteins. For example, in some embodiments, a bispecific protein can bind to both BAFF and B7RP1.

A patient is receiving "concurrent" treatment with two or more therapeutics when the patient receives the two or more therapeutics during the same general timeframe, optionally at the very same time. For example, if a patient were dosed with one therapeutic daily on an ongoing basis and were also dosed with another therapeutic once a month on an ongoing basis, the patient would be receiving these two drugs concurrently. Similarly, a patient dosed with two different therapeutics, each administered every two weeks, but not on the same day, would be receiving concurrent treatment with the two therapeutics. Further, a patient receiving one therapeutic on an ongoing basis once per week and another therapeutic once per day for only three days would be receiving treatment for a short period of time with these two therapeutics.

As meant herein, an "Fc region" is a dimer consisting of two polypeptide chains joined by one or more disulfide bonds, each chain comprising part or all of a hinge domain plus a CH2 and a CH3 domain. Each of the polypeptide chains is referred to as an "Fc polypeptide chain." More specifically, the Fc regions contemplated for use with the present invention are IgG Fc regions, which can be mammalian, for example human, IgG1, IgG2, IgG3, or IgG4 Fc regions. Among human IgG1 Fc regions, at least two allelic types are known. The amino acid sequences an Fc polypeptide chain can vary from those of a mammalian Fc polypeptide by no more than 20, 15, 12, 10, 8, 5, or 3 substitutions, insertions, or deletions of a single amino acid relative to a mammalian Fc polypeptide amino acid sequence. Alternatively or in addition, the amino acid sequence of an Fc polypeptide chain can vary from the sequence of a known or naturally occurring Fc polypeptide chain by no more thant 10 insertions, deletions, or substitutions of a single amino acid per every 100 amino acids of sequence. In some embodiments, such variations can be "heterodimerizing alterations" that facilitate the formation of heterodimers over homodimers. In referring to particular positions within an Fc polypeptide chain, the EU numbering system (Edelman et al. (1969), Proc. Natl. Acad. Sci. 63: 78-85) is used, as illustrated in the alignment of human IgG Fc polypeptide chains in Table 1 below.

TABLE 1

Alignment of amino acid sequences of human IgG Fc regions

```
IgG1        ------------------------------------------------
IgG2        ------------------------------------------------
IgG3              ELKTPLGDTTHTCPRCPEPKSCDTPPPCPRCPEPKSCDTPPPCPRCP
IgG4        ------------------------------------------------

225       235       245       255       265       275
              *         *         *         *         *         *
IgG1 EPKSCDKTHTCPPCPAPELLGGPSVFLFPPKPKDTLMISRTPEVTCVVVDVSHEDPEVKF
IgG2 ERKCCVE---CPPCPAPPVA-GPSVFLFPPKPKDTLMISRTPEVTCVVVDVSHEDPEVQF
IgG3 EPKSCDTPPPCPRCPAPELLGGPSVFLFPPKPKDTLMISRTPEVTCVVVDVSHEDPEVQF
IgG4 ESKYG---PPCPSCPAPEFLGGPSVFLFPPKPKDTLMISRTPEVTCVVVDVSQEDPEVQF 285       295       305       315       325       335
              *         *         *         *         *         *
IgG1 NWYVDGVEVHNAKTKPREEQYNSTYRVVSVLTVLHQDWLNGKEYKCKVSNKALPAPIEKT
IgG2 NWYVDGMEVHNAKTKPREEQFNSTFRVVSVLTVVHQDWLNGKEYKCKVSNKGLPAPIEKT
IgG3 KWYVDGVEVHNAKTKPREEQYNSTFRVVSVLTVLHQDWLNGKEYKCKVSNKALPAPIEKT
IgG4 NWYVDGVEVHNAKTKPREEQFNSTYRVVSVLTVLHQDWLNGKEYKCKVSNKGLPSSIEKT 345       355       365       375       385       395
              *         *         *         *         *         *
IgG1 ISKAKGQPREPQVYTLPPSRDELTKNQVSLTCLVKGFYPSDIAVEWESNGQPENNYKTTP
IgG2 ISKTKGQPREPQVYTLPPSREEMTKNQVSLTCLVKGFYPSDIAVEWESNGQPENNYKTTP
IgG3 ISKTKGQPREPQVYTLPPSREEMTKNQVSLTCLVKGFYPSDIAVEWESSGQPENNYNTTP
IgG4 ISKAKGQPREPQVYTLPPSQEEMTKNQVSLTCLVKGFYPSDIAVEWESNGQPENNYKTTP 405       415       425       435       445
              *         *         *         *         *
IgG1 PVLDSDGSFFLYSKLTVDKSRWQQGNVFSCSVMHEALHNHYTQKSLSLSPGK (SEQ ID NO: 33)
IgG2 PMLDSDGSFFLYSKLTVDKSRWQQGNVFSCSVMHEALHNHYTQKSLSLSPGK (SEQ ID NO: 34)
IgG3 PMLDSDGSFFLYSKLTVDKSRWQQGNIFSCSVMHEALHNRFTQKSLSLSPGK (SEQ ID NO: 35)
IgG4 PVLDSDGSFFLYSRLTVDKSRWQEGNVFSCSVMHEALHNHYTQKSLSLSLGK (SEQ ID NO: 36)
```

"Heterodimerizing alterations" generally refer to alterations in the CH3 regions two different IgG heavy chains that facilitate the formation of heterodimeric heavy chain dimers, that is, dimerized heavy chains that do not have identical amino acid sequences. Heterodimerizing alterations can be asymmetric, that is, one heavy chain having a certain alteration can pair with another heavy chain having a different alteration. These alterations facilitate heterodimerization and disfavor homodimerization. One example of such paired heterodimerizing alterations are the so-called "knobs and holes" substitutions. See, e.g., U.S. Pat. No. 7,695,936 and US Patent Application Publication 2003/0078385, the portions of which describe such mutations are incorporated herein by reference. As meant herein, heavy chain-heavy chain pair that contains one pair of knobs and holes substitutions, contains one substitution in one heavy chain and another substitution in the other heavy chain. For example, the following knobs and holes substitutions have been found to increase heterodimer formation as compared with that found with unmodified heavy chains: 1) Y407T in one chain and T366Y in the other; 2) Y407A in one chain and T366W in the other; 3) F405A in one chain and T394W in the other; 4) F405W in one chain and T394S in the other; 5) Y407T in one chain and T366Y in the other; 6) T366Y and F405A in one chain and T394W and Y407T in the other; 7) T366W and F405W in one chain and T394S and Y407A in the other; 8) F405W and Y407A in one chain and T366W and T394S in the other; and 9) T366W in one polypeptide of the Fc and T366S, L368A, and Y407V in the other. As meant herein, mutations in an Fc polypeptide are denoted in the following way. The amino acid (using the one letter code) normally present at a given position in the CH3 region using the EU numbering system (which is presented in Edelman et al. (1969), Proc. Natl. Acad. Sci. 63: 78-85) is followed by the EU position, which is followed by the alternate amino acid that is present at that position. For example, Y407T means that the tyrosine normally present at EU position 407 is replaced by a threonine. For the sake of clarity, the EU system of numbering is illustrated in Table 1 below. Alternatively or in addition to such alterations, substitutions creating new disulfide bridges can facilitate heterodimer formation. See, e.g., US Patent Application Publication 2003/0078385, the portions of which describe such mutations are incorporated herein by reference. Such alterations in an IgG1 Fc region include, for example, the following substitutions: Y349C in one Fc-polypeptide chain and S354C in the other; Y349C in one Fc-polypeptide chain and E356C in the other; Y349C in one Fc-polypeptide chain and E357C in the other; L351C in one Fc-polypeptide chain and S354C in the other; T394C in one Fc-polypeptide chain and E397C in the other; or D399C in one Fc-polypeptide chain and K392C in the other. Similarly, substitutions changing the charge of a one or more residue, for example, in the CH3-CH3 interface, can enhance heterodimer formation as explained in WO 2009/089004, the portions of which describe such substitutions are incorporated herein by reference. Such substitutions are referred to herein as "charge pair substitutions," and an Fc region containing one pair of charge pair substitutions contains one substitution in one heavy chain and a different substitution in the other. General examples of charge pair substitutions include the following: 1) K409D or K409E in one chain plus D399K or D399R in the other; 2) K392D or K392E in one chain plus D399K or D399R in the other; 3) K439D or K439E in one chain plus D356K or D356R in the other; and 4) K370D or K370E in one chain plus E357K or E357R in the other. In addition, the substitutions R355D, R355E, K360D, or K360R in both chains can stabilize heterodimers when used with other heterodimerizing alterations. Specific charge pair substitutions can be used either alone or with other charge pair substitutions. Specific examples of single pairs of charge pair substitutions and combinations thereof include the following: 1) K409E in one chain plus D399K in the other; 2) K409E in one chain plus D399R in the other; 3) K409D in one chain plus D399K in the other; 4) K409D in one chain plus D399R in the other; 5) K392E in one chain plus D399R in the other; 6) K392E in one chain plus D399K in the other; 7) K392D in one chain plus D399R in the other; 8) K392D in one chain plus D399K in the other; 9) K409D and K360D in one chain plus D399K and E356K in the other; 10) K409D and K370D in one chain plus D399K and E357K in the other; 11) K409D and K392D in one chain plus D399K, E356K, and E357K in the other; 12) K409D and K392D on one chain and D399K on the other; 13) K409D and K392D on one chain plus D399K and E356K on the other; 14) K409D and K392D on one chain plus D399K and D357K on the other; 15) K409D and K370D on one chain plus D399K and D357K on the other; 16) D399K on one chain plus K409D and K360D on the other; and 17) K409D and K439D on one chain plus D399K and E356K on the other. Any of these heterodimerizing alterations can be part of an immunoglobulin IgG heavy chain as described herein.

A "human" antibody or protein, as meant herein, is an antibody or protein encoded by a nucleic acid sequence of human origin. A human antibody or protein can be made in cultured non-human cells or in vivo in a transgenic organism into which a nucleic acid molecule encoding the human antibody or protein has been introduced. Alternatively, a human antibody or protein can be made in cultured human cells or in a human in vivo.

An "IgG antibody," as meant herein, is an antibody that consists essentially of the immunoglobulin domains present in most naturally-occurring IgG antibodies, i.e., a immunoglobulin heavy chain comprising a heavy chain variable (VH) region, a first heavy chain constant (CH1) region, a hinge region, a second heavy chain constant (CH2) region, and a third heavy chain constant (CH3) region and a light chain comprising a light chain variable (VL) region and a light chain constant (CL) region. Numerous sequences of such immunoglobulin domains are reported throughout the scientific literature, e.g., in SEQUENCES OF IMMUNOLOGICAL INTEREST, Public Health Service, N.I.H., Bethesda, Md., 1991. Naturally-occurring antibodies including only two immunoglobulin heavy chains and no immunoglobulin light chains, such as some found in camels and sharks (see, e.g., Muyldermans et al., 2001, J. Biotechnol. 74:277-302; Desmyter et al., 2001, J. Biol. Chem. 276:26285-90; Streltsov et al. (2005), Protein Science 14: 2901-2909), are not "IgG antibodies" as meant herein. An IgG antibody can be human or can be from another species. In addition, an IgG antibody can contain no more than 40, 35, 30, 25, 20, 15, 10, or 5 substitutions, insertions, and/or deletions of a single amino acid relative to the amino acid sequence of the heavy or light chains of a naturally occurring IgG antibody.

An "immunoglobulin heavy chain" refers to a heavy chain of an IgG, IgA, IgM, IgE, or IgD antibody or variants thereof containing not more than 40, 30, 25, 20, 15, 10, or 5 insertions, deletions, or substitutions of a single amino acid relative to an immunoglobulin heavy chain encoded by nucleic acid sequences originating in nature. An "immunoglobulin IgG heavy chain" is limited to heavy chains from IgG antibodies or variants thereof containing not more than 40, 30, 25, 20, 15, 10, or 5 insertions, deletions, or substitutions of a single amino acid relative to the amino acid sequence of an IgG heavy chain encoded by nucleic acid sequences originating in nature. An immunoglobulin heavy chain consists essentially of a number of distinct regions or domains including a VH region, a CH1 region, a hinge region, a CH2 region, and a CH3 region. In some other isotypes, i.e., IgM and IgA, additional regions are included downstream from the CH3 region. Immunoglobulin heavy chains and the regions included therein are generally described in, e.g., Carayannopoulos and Capra, Immunoglobulins: Structure and Function, pp. 283-314 in FUNDAMENTAL IMMUNOLOGY, $3^{rd}$ Ed, Paul, ed., Raven Press, New York, 1993, which is incorporated herein by reference. In addition, numerous sequences of subregions of immunoglobulin heavy chains are known in the art. See, e.g., Kabat et al., SEQUENCES OF PROTEINS OF IMMUNOLOGICAL INTEREST, Public Health Service N.I.H., Bethesda, Md., 1991. In some cases, a polypeptide chain that includes an immunoglobulin heavy chain plus some non-immunoglobulin sequences will be referred to herein as a "heavy chain."

An "immunoglobulin light chain," as meant herein, is a kappa or a lambda chain from a human antibody or an antibody from another species. Also included among immunoglobulin light chains, as meant herein, are proteins with no more than 20, 15, 10, or 5 insertions, deletions, and/or substitutions of a single amino acid relative to an immunoglobulin light chain encoded by nucleic acid sequences of natural origin. Immunoglobulin light chains are generally described in, e.g., Carayannopoulos and Capra, Immunoglobulins: Structure and Function, pp. 283-314 in FUNDAMENTAL IMMUNOLOGY, $3^{rd}$ Ed, Paul, ed., Raven Press, New York, 1993, which is incorporated herein by reference. A immunoglobulin light chain contains a VL region and a CL region. Numerous sequences of these regions are known in the art. See, e.g., Kabat et al., SEQUENCES OF PROTEINS OF IMMUNOLOGICAL INTEREST, Public Health Service N.I.H., Bethesda, Md., 1991. In some cases, a polypeptide chain that includes an immunoglobulin light chain plus some non-immunoglobulin sequences will be referred to herein as a "light chain."

An "immunoglobulin variable region," as meant herein, is a VH or VL region, which can be of human origin or from another species. Immunoglobulin variable regions are generally described in, e.g., Carayannopoulos and Capra, Immunoglobulins: Structure and Function, pp. 283-314 in FUNDAMENTAL IMMUNOLOGY, $3^{rd}$ Ed, Paul, ed., Raven Press, New York, 1993, which is incorporated herein by reference.

Also included among immunoglobulin variable regions, as meant herein, are proteins with no more than 20, 15, 10, or 5 insertions, deletions, and/or substitutions of a single amino acid relative to an immunoglobulin variable region encoded by nucleic acid sequences of natural origin. An immunoglobulin variable region contains three hypervariable regions, known as complementarity determining region 1 (CDR1), complementarity determining region 2 (CDR2), and complementarity determining region 3 (CDR3). These regions form the antigen binding site of an antibody. The CDRs are embedded within the less variable framework regions (FR1-FR4). The order of these subregions within a variable region is as follows: FR1-CDR1-FR2-CDR2-FR3-CDR3-FR4. Numerous sequences of immunoglobulin variable regions are known in the art. See, e.g., Kabat et al., SEQUENCES OF PROTEINS OF IMMUNOLOGICAL INTEREST, Public Health Service N.I.H., Bethesda, Md., 1991.

CDRs can be located in a VH region sequence in the following way. CDR1 starts at approximately residue 31 of the mature VH region and is usually about 5-7 amino acids long, and it is almost always preceded by a Cys-Xxx-Xxx-Xxx-Xxx-Xxx-Xxx-Xxx-Xxx (SEQ ID NO: 20) (where "Xxx" is any amino acid). The residue following the heavy chain CDR1 is almost always a tryptophan, often a Trp-Val, a Trp-Ile, or a Trp-Ala. Fourteen amino acids are almost always between the last residue in CDR1 and the first in CDR2, and CDR2 typically contains 16 to 19 amino acids. CDR2 may be immediately preceded by Leu-Glu-Trp-Ile-Gly (SEQ ID NO: 21) and may be immediately followed by Lys/Arg-Leu/Ile/VaVPhe/Thr/Ala-Thr/Ser/Ile/Ala. Other amino acids may precede or follow CDR2. Thirty two amino acids are almost always between the last residue in CDR2 and the first in CDR3, and CDR3 can be from about 3 to 25 residues long. A Cys-Xxx-Xxx almost always immediately precedes CDR3, and a Trp-Gly-Xxx-Gly (SEQ ID NO: 22) almost always follows CDR3.

Light chain CDRs can be located in a VL region in the following way. CDR1 starts at approximately residue 24 of the mature antibody and is usually about 10 to 17 residues long. It is almost always preceded by a Cys. There are almost always 15 amino acids between the last residue of CDR1 and the first residue of CDR2, and CDR2 is almost always 7 residues long. CDR2 is typically preceded by Ile-Tyr, Val-Tyr, Ile-Lys, or Ile-Phe. There are almost always 32 residues between CDR2 and CDR3, and CDR3 is usually about 7 to 10 amino acids long. CDR3 is almost always preceded by Cys and usually followed by Phe-Gly-Xxx-Gly (SEQ ID NO: 23).

A "linker," as meant herein, is a peptide that links two polypeptides. A linker can be from 1-80 amino acids in length. In some embodiments, a linker can be 2-40, 3-30, or 3-20 amino acids long. In some embodiments, a linker can be a peptide no more than 14, 13, 12, 11, 10, 9, 8, 7, 6, or 5 amino acids long. In other embodiments, a linker can be 5-25, 5-15, 10-20, or 20-30 amino acids long. In other embodiments, a linker can be about, 2, 3, 4, 5, 6, 7, 8, 9, 10, 11, 12, 13, 14, 15, 16, 17, 18, 19, 20, 21, 22, 23, 24, 25, 26, 27, 28, 29, or 30 amino acids long. In many cases, linkers lack free cysteine residues (i.e. not involved in disulfide bonds) and also do not contain N glycosylation sites (that is, Asn-Xxx-Ser/Thr, where X can be any amino acid except proline)

A "peptibody," as meant herein, is one or more biologically active peptides fused to an Fc region. Shimamoto et al. (2012), mAbs 4(5): 586-591, the portions of which explain the structure of a peptibody and how to make it are incorporated herein by reference.

A "peptide," as meant herein, is a polypeptide that consists of a short amino acid sequence, which may or may not be glycosylated and/or contain modified amino acids. A peptide can be from 2 to 75 amino acids long. In some embodiments, a peptide is 3-60, 3-50, 3-40, 3-30, or 3-20 amino acids long. In other embodiments, a peptide can be 5-25, 5-15, 10-20, or 20-30 amino acids long. In other embodiments, a peptide can be about, 2, 3, 4, 5, 6, 7, 8, 9, 10, 11, 12, 13, 14, 15, 16, 17, 18, 19, 20, 21, 22, 23, 24, 25, 26, 27, 28, 29, or 30 amino acids long.

A "therapeutically effective amount" of a drug used to treat a disease is an amount that can reduce the severity of a disease, reduce the severity of one or more symptoms associated with the disease or its treatment, or delay the onset of more serious symptoms or a more serious disease that can occur with some frequency following the treated condition.

"Treatment" of any disease mentioned herein encompasses an alleviation of at least one symptom of the disease, a reduction in the severity of the disease, or the delay or prevention of disease progression to more serious symptoms that may, in some cases, accompany the disease or lead to at least one other disease. Treatment need not mean that the disease is totally cured. A useful therapeutic agent needs only to reduce the severity of a disease, reduce the severity of one or more symptoms associated with the disease or its treatment, or delay the onset of more serious symptoms or a more serious disease that can occur with some frequency following the treated condition. For example, if the disease were an inflammatory bowel disease, a therapeutic agent used as a treatment may reduce the number of distinct sites of inflammation in the gut or the total extent of the gut affected. It may reduce pain and/or swelling, reduce symptoms such as diarrhea, constipation, or vomiting, and/or prevent perforation of the gut. A patient's condition can be assessed by standard techniques such as an x-ray performed following a barium enema or enteroclysis, endoscopy, colonoscopy, and/or a biopsy. Suitable procedures vary according to the patient's condition and symptoms. Similarly, if the disease treated were systemic lupus erythematosus (SLE), disease activity could be evaluated using the SLEDAI index for scoring, as explained below.

Bispecific Proteins that Bind to BAFF and B7RP1

Disclosed herein are bispecific proteins that bind to B7RP1 and BAFF and/or that can inhibit B7RP1-mediated T cell proliferation and BAFF-mediated B cell proliferation in vitro. The BAFF and B7RP1 proteins to which a bispecific protein as described herein binds can be human proteins and/or can be proteins from another species such as cynomolgus monkey, rhesus monkey, chimpanzee, mouse, and/or rabbit, among others. In some embodiments, a bispecific protein as described herein can, for example, bind to both human (*Homo sapiens*) and cynomolgus monkey (*Macaca fascicularis*) B7RP1 and BAFF proteins.

In some embodiments, these bispecific proteins can be bispecific IgG antibodies in which the B7RP1-binding portion and the BAFF-binding portion each consists essentially of an immunoglobulin IgG heavy chain and an immunoglobulin light chain. Thus, such a bispecific antibody contains two different immunoglobulin heavy chains and two different immunoglobulin light chains. Together, these two pairs of immunoglobulin heavy and light chains form a complete bispecific IgG antibody. Bispecific IgG antibodies are known in the art, and a number of other formats for bispecific antibodies are also known. See, e.g., Kontermann, Bispecific Antibodies: Developments and Current Perspectives, pp. 1-28 in BISPECIFIC ANTIBODIES, Kontermann, ed., Springer-Verlag, Berlin, Heidelburg, 2011, the portions of which describe these antibodies are incorporated herein by reference. Antibodies that can bind to BAFF and B7RP1, regardless of format, are contemplated herein. Bispecific IgG antibodies can be human, humanized, or chimeric and can be of the IgG1, IgG2, IgG3, or IgG4 isotype. In some embodiments, bispecific IgG antibodies can be conjugated to other moieties. Amino acid sequences of anti-BAFF and anti-B7RP1 antibodies are known in the art. See e.g., U.S. Pat. No. 7,737,111 and U.S. Patent Application Publication US 2011/0117093. The portions of these documents that describe such antibodies are incorporated herein by reference. In some embodiments, such bispecific antibodies can comprise "heterodimerizing alterations," as defined above, including charge pair substitutions, that facilitate formation of a heterotetrameric bispecific IgG antibody.

In other embodiments, the bispecific proteins described herein can be fusion proteins comprising an antibody that binds to B7RP1, which comprises an immunoglobulin IgG heavy chain and an immunoglobulin light chain, and a peptide that binds to BAFF. The BAFF-binding peptide can be present in one or multiple copies, such as two, three, four, five, six, seven, eight, or up to 16 copies. The BAFF-binding peptide may bind to BAFF proteins from species such as mouse, cynomolgus monkey, and/or humans, among many other possible species. The antibody can be an anti-B7RP1 IgG antibody, optionally a human or humanized antibody that binds to human and/or cynomolgus monkey B7RP1. In some embodiments, a linker can be attached to the C terminus of the heavy chain of the anti-B7RP1 IgG antibody, followed by a first BAFF-binding peptide, another linker, and a second BAFF-binding peptide. A third, fourth, fifth, sixth, seventh, eighth, or up to sixteenth BAFF-binding peptide can follow these two, optionally interspersed with linkers. Alternatively or in addition, one, two, three, four, five, six, seven, or eight BAFF-binding peptides can be inserted elsewhere in the anti-B7RP1 antibody, for example at the N terminus of the immunoglobulin heavy chain or immunoglobulin light chain or in a loop region in the CH2 or CH3 region. The IgG antibody can be a mammalian antibody, such as a human or murine antibody. The anti-B7RP1 antibody can be a human or humanized IgG1, IgG2, IgG3, or IgG4 antibody. In such bispecific fusion proteins comprising an anti-B7RP1 IgG antibody, the bispecific protein can comprise a heavy chain comprising the amino acid sequence of SEQ ID NO:17 or SEQ ID NO:18 and an immunoglobulin light chain comprising the amino acid sequence of SEQ ID NO:19. Variants comprising a heavy chain having an amino acid sequence containing no more than 30, 25, 20, 15, 10, 5, or 3 insertions, deletions, or substitutions of a single amino acid relative to SEQ ID NO: 17 or 18 are contemplated. Similarly, variants comprising an immunoglobulin light chain having an amino acid sequence containing no more 20, 15, 10, 8, 7, 5, or 3 insertions, deletions, or substitutions or a single amino acid relative SEQ ID NO:19 are contemplated. Such bispecific proteins can be tetramers comprising two polypeptides comprising the amino acid sequence of SEQ ID NO:17 or 18 or a variant thereof and two light chains comprising the amino acid sequence of SEQ ID NO:19 or a variant thereof.

A BAFF-binding peptide portion of a bispecific fusion protein as described above can comprise the amino acid sequence of SEQ ID NO:1, SEQ ID NO:2, or SEQ ID NO:3. Such BAFF-binding peptides are described in U.S. Pat. No. 7,737,111, the relevant portions of which are incorporated herein by reference. In some embodiments, there may be one, two, three, four, five, six, seven, eight, nine, ten, eleven, twelve, thirteen, fourteen, fifteen, or sixteen copies of such a BAFF-binding peptide present in the bispecific protein. A BAFF-binding peptide can be attached to the carboxy end of the anti-B7RP1 antibody, for example, via a linker. For example, the carboxy end of an anti-B7RP1 IgG antibody can be followed by a linker having, for example, the amino acid sequence of Gly-Gly-Gly-Gly (SEQ ID NO:4). Examples of other suitable linkers include Gly-Gly, Gly-Gly-Gly, Gly-Gly-Gly-Ser (SEQ ID NO:37), Gly-Gly-Gly-Pro (SEQ ID NO:38), Gly-Gly-Gly-Gln (SEQ ID NO:39), and Gly-Gly-Gly-Gly-Gly (SEQ ID NO:40), among many others. This linker can be followed by a BAFF-binding peptide. The BAFF-binding peptide can be followed by another linker comprising, for example, the amino acid sequence of SEQ ID NO:5, SEQ ID NO:6, SEQ ID NO:7, or SEQ ID NO:24. Other linker could also be used. This linker can be followed by another BAFF-binding peptide comprising, for example, the amino acid sequence of SEQ ID NO:1.

In the bispecific fusion proteins described immediately above or in the bispecific heterotetrameric IgG antibodies described above, a VL region can contain a CDR1, a CDR2, and a CDR3 comprising the amino acid sequences of SEQ ID NO:8, SEQ ID NO:9, and SEQ ID NO:10, respectively. A VH region CDR1, CDR2, and CDR3 can comprise the amino acid sequences of SEQ ID NO:11, SEQ ID NO:12, and SEQ ID NO:13, respectively. In some embodiments, a VL region of the IgG antibody can comprise the amino acid sequence of SEQ ID NO:14 or a variant thereof, and the VH region can comprise the amino acid sequence of SEQ ID NO:15 or a variant thereof. Such variant sequences can comprise not more than 10 deletions, insertions of substitutions of a single amino acid per 100 amino acids relative to a reference sequence.

Proteins Comprising a Linker

Provided herein are linkers having the amino acid sequences of SEQ ID NO:5, 6, or 7 that confer favorable physical properties on a protein that contains them. As shown in Example 1 below, the use of two particular linkers, i.e., those having the amino acid sequences of SEQ ID NO:6 and SEQ ID NO:7, had positive effects on properties such as expression, stability, and viscosity of a bispecific molecule. Thus, a variety of proteins containing these linkers may have such favorable properties as compared to similar proteins containing other linkers.

Therapeutic Uses of Bispecific Proteins

The bispecific proteins binding to BAFF and B7RP1 described herein can be used as therapeutics for a variety of indications, particularly conditions driven by autoantibodies and/or conditions mediated by both T cells and B cells. Such conditions include, for example, SLE, lupus, nephritis, ANCA-positive vasculitis, rheumatoid arthritis (RA), dermatomyositis, polymyositis, gastrointestinal diseases such as Crohn's disease, ulcerative colitis, and celiac disease, skin conditions such as pemphigus, pemphigoid, and subacute cutaneous lupus erythematosus (SCLE), diseases of the nervous system such as multiple sclerosis and chronic inflammatory demyelinating polyneuropathy (CIDP), neuromuscular diseases such as myasthenia gravis, diseases involving the kidneys such as Goodpasture's syndrome and glomerulonephritis, hematologic conditions such as autoimmune hemolytic anemia (AIHA), idiopathic thrombocytopenic purpura (ITP), and autoimmune neutropenia, liver conditions such as chronic active hepatitis and primary biliary cirrhosis, Sjogren's syndrome, systemic sclerosis, and endocrine conditions including Hashimoto's thyroiditis, Graves' disease, Addison's disease, and multiple endocrine autoimmune failure (commonly including diabetes, hypothyroidism, Addison's disease, and gonadal failure). A therapeutically effective amount of a bispecific protein as described herein can be administered to a patient suffering from any of these conditions to treat the condition.

In one embodiment, a bispecific protein that can inhibit BAFF-mediated B cell proliferation and B7RP1-mediated T cell proliferation can be used to treat a patient suffering from SLE. SLE is an autoimmune disease of unknown etiology marked by autoreactivity to nuclear self antigens. Its clinical manifestations are so diverse that it is questionable whether it is truly a single disease or a group of related conditions. Kotzin (1996) Systemic lupus erythematosus. *Cell* 85: 303-306; Rahman and Isenberg (2008), Systemic lupus erythematosus. *N. Engl. J. Med.* 358: 929-939. Symptoms can include the following: constitutional symptoms such as malaise, fatigue, fevers, anorexia, and weight loss; diverse skin symptoms including acute, transient facial rashes in adults, bullous disease, and chronic and disfiguring rashes of the head and neck; arthritis; muscle pain and/or weakness; cardiovascular symptoms such as mitral valve thickening, vegetations, regurgitation, stenosis, pericarditis, and ischemic heart disease, some of which can culminate in stroke, embolic disease, heart failure, infectious endocarditis, or valve failure; nephritis, which is a major cause of morbidity in SLE; neurological symptoms including cognitive dysfunction, depression, psychosis, coma, seizure disorders, migraine, and other headache syndromes, aseptic meningitis, chorea, stroke, and cranial neuropathies; hemotologic symptoms including leucopenia, thrombocytopenia, serositis, anemia, coagulation abnormalities, splenomegaly, and lymphadenopathy; and various gastrointestinal abnormalities. Id; Vratsanos et al., "Systemic Lupus Erythematosus," Chapter 39 in Samter's Immunological Diseases, 6$^{th}$ Edition, Austen et al., eds., Lippincott Williams & Wilkins, Phiiladelphia, Pa., 2001. Severity of symptoms varies widely, as does the course of the disease. SLE can be deadly.

An SLE patient can be treated with a bispecific protein that inhibits BAFF and B7RP1 before, after, or concurrently with treatment using an existing therapy for SLE. Such existing therapies for SLE include corticosteroids such as prednisone, prednisolone, and methylprednisolone, antimalarials such as hydroxychloroquine, quinacrine, and chloroquine, retinoic acid, aspirin and other nonsteroidal anti-inflammatory drugs (NSAIDs), cyclophosphamide, dehydroepiandrosterone, mycophenolate mofetil, azathioprine, chlorambucil, methotrexate, tacrolimus, dapsone, thalidomide, leflunomide, cyclosporine, belimumab, anti-CD20 antibodies such as rituximab, and fusion proteins such as abatacept.

The disease activity of SLE patients can be rated using an instrument such as the Systemic Lupus Erythrmatosus Disease Activity Index (SLEDAI), which provides a score for disease activity that takes into consideration the following symptoms, which are weighted according to severity: seizure, psychosis, organic brain syndrome, visual disturbance, cranial nerve disorder, lupus headache, vasculitis, arthritis, myositis, urinary casts, hematuria, proteinuria, pyuria, new rash, alopecia, mucosal ulcers, pleurisy, pericarditis, low complement, increased DNA binding, fever, thrombocytopenia, and leucopenia. Bombardier et al. (1992), Arthr. & Rheum. 35(6): 630-640, the relevant portions of which are incorporated herein by reference. The treatments described herein can be useful in lessening or eliminating symptoms of SLE as measured by SLEDAI. Methods of treatment described herein can improve a patient's SLEDAI score compared to a baseline value for the same patient prior to initiation of treatment with a bispecific protein as described herein.

Another method for assessing disease activity in SLE is the British Isles Lupus Assessment Group (BILAG) index, which is a disease activity assessment system for SLE patients based on the principle of the physician's intention to treat. Stoll et al. (1996), Ann. Rheum Dis. 55: 756-760; Hay et al. (1993), Q. J. Med. 86: 447-458. The portions of these references describing the BILAG are incorporated herein by reference. A BILAG score is assigned by giving separate numeric or alphabetic disease activity scores in each of eight organ-based systems, general (such as fever and fatigue), mucocutaneous (such as rash and alopecia, among many other symptoms), neurological (such as seizures, migraine headaches, and psychosis, among many other symptoms), musculoskeletal (such as arthritis), cardiorespiratory (such as cardiac failure and decreased pulmonary function), vasculitis and thrombosis, renal (such as nephritis), and hematological. Id. The treatments described herein can be useful in lessening or eliminating symptoms of SLE as measured by the BILAG index or in decreasing a patient's BILAG score as compared to a baseline value prior to the initiation of treatment with a bispecific protein as described herein.

A bispecific protein as described herein, which inhibits BAFF-mediated proliferation of B cells and B7RP1-mediated proliferation of T cells, could also be used to treat rheumatoid arthritis (RA). RA is a chronic disease with systemic symptoms, as well as symptoms relating specifically to the joints. Symptoms commonly include synovitis, leading to painful and swollen joints, and various laboratory abnormalities such as higher-than-normal levels of rheumatoid factor, anti-citrulline modified protein (anti-CCP) antibodies, and C-reactive protein (CRP) and an elevated erythrocyte sedimentation rate (ESR). Less common symptoms include various extra-articular symptoms involving, e.g., tendons, ligaments, blood vessels, the heart, and the lungs. Disease activity can be often measured using a variety of indices. See, e.g., Anderson et al. (2012), Arthritis care & Res. 64 (5): 640-647, the portions of which discuss such indices are incorporated herein by reference. Elements included in such scoring indices include the number of tender joints, the number of swollen joints, functional assessments, and various laboratory findings such as CRP, ESR, etc.

In some embodiments, a patient suffering from RA can be treated with a bispecific protein that inhibits BAFF-mediated B cell proliferation and B7RP1-mediated T cell proliferation before, after, or concurrently with treatment with a drug in current use for RA. Therapeutics currently in use for rheumatoid arthritis (RA) include non-steroidal anti-inflammatory drugs (NSAIDs) (such aspirin and cyclooxygenase-2 (COX-2) inhibitors), disease modifying anti-inflammatory drugs (DMARDs, such as methotrexate, leflunomide, and sulfasalazine), anti-malarials (such as hydroxychloroquine), cyclophosphamide, D-penicillamine, azathioprine, gold salts, tumor necrosis factor inhibitors (such as etanercept, infliximab, adalimumab, golimumab, and certolizumab pegol), CD20 inhibitors such as rituximab, IL-1 antagonists such as anakinra, IL-6 inhibitors such as tocilizumab, inhibitors of Janus kinases (JAKs, such as tofacitinib), abatacept, and corticosteroids, among others.

A therapeutically effective amount of a bispecific protein as described herein, which inhibits BAFF-mediated proliferation of B cells and B7RP1-mediated proliferation of T cells, can also be used to treat an inflammatory bowel disease, such as Crohn's disease or ulcerative colitis. Crohn's disease is involves an abnormal inflammation of any portion of the alimentary tract from the mouth to the anus, although in most patients abnormal inflammation is confined to the ileocolic, small-intestinal, and colonic-anorectal regions. Typically, the inflammation is discontinuous. Common symptoms include abdominal pain, anorexia, weight loss, fever, diarrhea, fullness and/or tenderness in the right lower quadrant of the abdomen, constipation, vomiting, and perianal discomfort and discharge. Other possible symptoms include peripheral arthritis, growth retardation, episcleritis, aphthous stomatitis, erythema nodosum, pyoderma gangrenosum, kidney stones, impaired urinary dilution and alkalinization, malabsorption, and gallstones, among others. See e.g. Strober et al., Medical Immunology, 10$^{th}$ Edition, Section III, Ch. 35 (2001); Merck Manual of Diagnosis and Therapy, 17$^{th}$ Edition, Section 3, Ch. 31 (1999). Macrophages isolated from patients with Crohn's disease produce increased amounts of IL-12, IFNγ, TNFα, and other inflammatory cytokines.

Ulcerative colitis, though it is sometimes hard to distinguish from Crohn's disease, is distinct from Crohn's disease in several respects. First, it is generally limited to the colon while Crohn's disease may occur throughout the alimentary tract. Second, ulcerative colitis mainly involves inflammation only of the superficial layers of the bowel, unlike Crohn's disease in which the inflammation can penetrate all way through the wall of the bowel or other location in the alimentary tract. Finally, ulcerative colitis typically involves a continuous area of inflammation, rather than the discontinuous sites of inflammation typical of Crohn's disease. Like Crohn's disease, ulcerative colitis is found primarily in urban areas. Also, genetic factors likely play a role in ulcerative colitis since there is a familial aggregation of cases. Autoantibodies are observed in ulcerative colitis patients more often than Crohn's disease patients. The autoantibodies are often directed to colonic epithelial cell components. Among the most common are antineutrophil cytoplasmic antibodies with specificities for catalase, α-enolase, and lactoferrin. In some cases such antibodies cross react with colonic microorganisms.

In clinical trials, Crohn's disease activity is often scored using the Crohn's Disease Activity Index (CDAI). The CDAI provides a disease activity score based on eight factors including (1) the number of liquid or soft stools per day, (2) a patient rating of the amount of abdominal pain per day, (3) a patient rating of general well-being, (4) a patient report of other symptoms including arthritis, iritis, uveitis, erythema nodosum, pyoderma gangrenosum, ephthous stomatitis, anal fissure, fitula, or abscess, other fistula, or fever, (5) patient report of taking lomotil or other opiates for diarrhea, (6) abdominal mass, (7) hematocrit, and (8) body weight. See, e.g., Best et al. (1976), Gastroenterol. 70: 439-444, the relevant portions of which are incorporated herein by reference.

Symptoms of ulcerative colitis are variable. They may include diarrhea, tenesmus, abdominal cramps, blood and mucus in the stool, fever, and rectal bleeding. Toxic megacolon, a potentially life-threatening condition in which the colon is dilated beyond about 6 centimeters and may lose its muscular tone and/or perforate, may also occur. Other symptoms that may accompany ulcerative colitis include peripheral arthritis, ankylosing spondylitis, sacroiliitis, anterior uveitis, erythema nodosum, pyoderma gangrenosum, episcleritis, autoimmune hepatitis, primary sclerosing cholangitis, cirrhosis, and retarded growth and development in children.

In some embodiments a patient suffering from an inflammatory bowel disease (IBD), such as Crohn's disease or ulcerative colitis, can be treated with a bispecific protein that binds to BAFF and B7RP1 before, after, or concurrently with treatment with an existing therapy for IBD. Existing therapeutics for IBD include, for example, sulfasalazine, 5-aminosalicylic acid and its derivatives (such as olsalazine, balsalazide, and mesalamine), anti-TNF antibodies (including infliximab, adalimumab, golimumab, and certolizumab pegol), corticosteroids for oral or parenteral administration (including prednisone, methylprednisone, budesonide, or hydrocortisone), adrenocorticotropic hormone, antibiotics (including metronidazole, ciprofloxacin, or rifaximin), azathioprine, 6-mercaptopurine, methotrexate, cyclosporine, tacrolimus, and thalidomide.

Nucleic Acids Encoding Bispecific Proteins

Provided herein are nucleic acids encoding a bispecific protein that can inhibit B7RP1-mediated T cell proliferation and BAFF-mediated B cell proliferation. For example, SEQ ID NO:52 encodes the VL region having the amino acid sequence of SEQ ID NO:14, and SEQ ID NO:53 encodes the VH region having the amino acid sequence of SEQ ID NO:15. Similarly, SEQ ID NOs:55 and 56 encode the amino acid sequences of SEQ ID NOs:17 and 18, respectively, which are polypeptides comprising the heavy chain of an anti-B7RP1 antibody fused to two BAFF-binding peptides. SEQ ID NO:57 encodes the light chain of an anti-B7RP1 antibody, which can be part of a hetero-tetrameric bispecific IgG antibody or a bispecific fusion protein, as described above. Any nucleic acid sequence encoding any amino acid sequence provided herein is contemplated. Similarly, nucleotide sequence variants encoding the amino acid sequence variants described above are also included within the ambit of the invention. More specifically, nucleotide sequences encoding amino acid sequences that vary by no more than 10 insertions, deletions, or substitutions of a single amino acid per 100 amino acids from amino acid sequences disclosed herein are contemplated.

Nucleic acid sequences encoding bispecific proteins described herein can be determined by one of skill in the art based on the amino acid sequences provided herein and knowledge in the art. Besides more traditional methods of producing cloned DNA segments encoding a particular amino acid sequence, companies such as DNA 2.0 (Menlo Park, Calif., USA) and BlueHeron (Bothell, Wash., USA), among others, now routinely produce chemically synthesized, gene-sized DNAs of any desired sequence to order, thus streamlining the process of producing such DNAs. Codon usage can be adjusted so as to optimize expression in the system of choice.

Methods of Making Bispecific Proteins that Bind to BAFF and B7RP1

Nucleic acids encoding the bispecific proteins described herein can be inserted into vectors appropriate for the host cell in which the nucleic acid will be expressed. These nucleic acids can be introduced into the host cells by any of the methods well-known in the art. Host cells that can be used include bacteria, including Escherichia coli, yeast, including Saccharomyces cerevisiae or Pichia pastoris, insect cells including Spodoptera frugiperda cells, plant cells, and mammalian cells, including Chinese hamster ovary (CHO) cells, baby hamster kidney (BHK) cells, monkey kidney cells, HeLa cells, human hepatocellular carcinoma cells, and 293 cells, among many others. These host cells can be cultured under conditions such that the introduced nucleic acids will be expressed, and the bispecific protein can be recovered from the culture supernatant or the cell mass.

Generally, the procedure used to introduce the nucleic acids into the host cells may depend upon the host cell into which the nucleic acids are to be introduced. Methods of introducing nucleic acids into bacteria are well-known in the art. For example, electroporation or calcium choride transformation are commonly used. Methods for introduction of nucleic acids into yeast are also well-known in the art and include, for example, transformation methods using lithium acetate and polyethylene glycol. Methods for introducing heterologous polynucleotides into mammalian cells are well known in the art and include, but are not limited to, dextran-mediated transfection, calcium phosphate precipitation, polybrene mediated transfection, protoplast fusion, electroporation, encapsulation of the polynucleotide(s) in liposomes, and direct microinjection of the DNA into nuclei.

Expression vectors used in any of the host cells can contain sequences necessary for DNA replication, selection of host cells containing the vector, and expression of the exogenous nucleotide sequences. Such sequences can typically include one or more of the following nucleotide sequences: a promoter, one or more enhancer sequences, an origin of replication, a transcriptional termination sequence, a complete intron sequence containing a donor and acceptor splice site, a sequence encoding a leader sequence for polypeptide secretion, a ribosome binding site, a polyadenylation sequence, a polylinker region for inserting the nucleic acid encoding the polypeptide to be expressed, and a selectable marker element. Numerous expression vectors appropriate for expression in various host cells are known in the art and are commercially available.

Pharmaceutical Compositions, Dosing, and Methods of Administration

Pharmaceutical compositions comprising the bispecific proteins described herein are provided. Such compositions can comprise a therapeutically effective amount of a bispecific protein with one or more additional components such as a physiologically acceptable carrier, excipient, or diluent. Such additional components can include buffers, carbohydrates, polyols, amino acids, chelating agents, stabilizers, and/or preservatives, among many possibilities. Many such additional components are described in, e.g., REMINGTON'S PHARMACEUTICAL SCIENCES, 18$^{th}$ Edition, (A. R. Gennaro, ed.), 1990, Mack Publishing Company, the relevant portions of which are incorporated herein by reference.

Dosing of the bispecific proteins described herein can be adjusted to achieve the desired effects. In many cases, repeated dosing will be required because of the chronic nature of the disease being treated. For example, a bispecific protein as described herein can be dosed twice per week, once per week, once every two, three, four, five, six, seven, eight, nine, or ten weeks, or once every two, three, four, five, or six months. The amount of the bispecific protein administered on each day that it is administered can be from about 0.0036 mg to about 700 mg. Alternatively, the dose can be calibrated according to the estimated skin surface of a patient, and each dose can be from about 0.002 µg/m$^2$ to about 350 mg/m$^2$. In another alternative, the dose can be calibrated according to a patient's weight, and each dose can be from about 0.000051 mg/kg to about 10.0 mg/kg.

The bispecific proteins, or pharmaceutical compositions containing these molecules, can be administered by any feasible method. Therapeutics that comprise a protein will ordinarily be administered by a parenteral route, for example by injection, since oral administration, in the absence of some special formulation or circumstance, would lead to hydrolysis of the protein in the acid environment of the stomach. Subcutaneous, intramuscular, intravenous, intraarterial, intralesional, and peritoneal bolus injections are possible routes of administration. The bispecific proteins can also be administered via infusion, for example intravenous or subcutaneous infusion. Topical administration is also possible, especially for diseases involving the skin. Alternatively, the bispecific proteins can be administered through contact with a mucus membrane, for example by intra-nasal, sublingual, vaginal, or rectal administration or administration as an inhalant. Alternatively, certain appropriate pharmaceutical compositions comprising a bispecific protein can be administered orally.

Having described the invention in general terms above, the following examples are offered by way of illustration and not limitation.

EXAMPLES

Example 1: Designing and Testing a BAFF/B7RP1 Bispecific Molecule for Human Therapeutic Use The object of this series of experiments was to find a bispecific molecule that (1) inhibits BAFF-mediated B cell proliferation and B7RP1-mediated T cell proliferation, (2) is highly active in biological assays, and (3) has favorable biophysical properties. A number of schematic designs for the fusion of a peptide that binds human BAFF to an anti-human B7RP1 IgG antibody (anti-huB7RP1) are illustrated in FIG. 1. The sequence of the BAFF-binding peptide is provided in SEQ ID NO:1, and the sequences of the immunoglobulin heavy and light chains of anti-huB7RP1 are provided in SEQ ID NO:25 and SEQ ID NO:19, respectively.

To determine which design had the best biophysical properties, while retaining biological activity, the bispecific molecules diagrammed in FIG. 1 were made and tested. In one construct, two tandem copies of the BAFF-binding peptide with an intervening linker (the "1K linker," having the amino acid sequence of SEQ ID NO:24) were fused to the N-terminus of either the immunoglobulin heavy chain (P71617) or immunoglobulin light chain (P71618) of anti-huB7RP1. See FIG. 1. The amino acid sequence of the P71617 heavy chain is provided in SEQ ID N0:26, and the amino acid sequence of the light chain of P71617 is the same as that of the immunoglobulin light chain of anti-huB7RP1 (SEQ ID NO:19). The amino acid sequence of the P71618 light chain is provided in SEQ ID NO:27, and the amino acid sequence of the heavy chain of P71618 is the same as the immunoglobulin heavy chain of anti-huB7RP1 (SEQ ID NO:25). Two tandem copies of the BAFF-binding peptide were also fused to the C-terminal end of the immunoglobulin heavy chain of anti-huB7RP1 (having the amino acid sequence of SEQ ID NO:25) using either the 1K linker mentioned above (having the amino acid sequence of SEQ ID NO:24; P71619) or a 5X(G4S) linker (SEQ ID NO: 71) between the two BAFF-binding peptides (P71620). The amino acid sequences of the heavy chains of these two fusion constructs are provided in SEQ ID NO:16 (P71619) and SEQ ID NO:28 (P71620). In construct P71621, two tandem copies of the BAFF-binding peptide with an intervening 1K linker were inserted into the antibody's CH3 domain between residues 358 and 359 of the amino acid sequence of SEQ ID NO:25 (the amino acid sequence of the immunoglobulin heavy chain of the anti-huB7RP1 antibody). The sequence of the heavy chain of the P71621 construct is provided in SEQ ID NO:29. In construct P71622, the BAFF-binding peptide was inserted into the CH3 domain of the immunoglobulin heavy chain of anti-huB7RP1 (between residues 358 and 359 of SEQ ID NO:25 and a second copy of the BAFF-binding peptide was fused to the C-terminal end of the heavy chain. The amino acid sequence of the heavy chain of P71622 is provided in SEQ ID NO:30. In construct P71623, one BAFF-binding peptide was inserted into the CH2 region (between residues 268 and 269 of SEQ ID NO:25), and a second BAFF-binding peptide was inserted into the CH3 region (between residues 358 and 359 of SEQ ID NO:25). SEQ ID NO:31 is the amino acid sequence of the heavy chain of P71623. Constructs P71619-P71623 all have the immunoglobulin light chain of anti-huB7RP1 (SEQ ID NO:19).

In constructs P74293 and P74294, the linker between the two tandem copies of the BAFF-binding peptides in construct P71619 was modified. The amino acid sequences of the heavy chains of P74293 and P74294 are provided in SEQ ID NO:17 and SEQ ID NO:18, respectively. The immunoglobulin light chains of these constructs also have the amino acid sequence of SEQ ID NO:19.

Nucleic acids encoding the constructs described above were made as follows. Nucleic acids encoding the N-terminal portion of the N-terminal BAFF peptide fusions (P71617 and P71618), including two copies of the BAFF-binding peptide plus an immunoglobulin heavy or light chain variable region, were generated synthetically. These were ligated, through convenient restriction endonuclease sites, to nucleic acids encoding the immunoglobulin heavy or light chain constant region in appropriate vectors. Nucleic acids encoding the heavy chain constant region C-terminal fusions (P71619 and P71620), Fc-loop insertions (P71621 and P71623), and the Fc-loop insertion/C-terminal fusion (P71622) were all generated synthetically and ligated into a vector containing the heavy chain variable region through convenient restriction endonuclease sites.

The various bispecific constructs described above were expressed in both transiently transfected 293 cells and stably transfected CHO cells. The fusion proteins were purified and tested for biological activity. No differences were observed in proteins produced in these two different kinds host cells.

The BAFF inhibitory activities of the bispecific molecules were tested in a BAFF-mediated human primary B cell proliferation assay. In brief, human B cells were purified from peripheral blood mononuclear cells (PBMCs) using negative selection using a human B cell kit II from Miltenyi Biotec (Auburn, Calif.). About $10^5$ purified B cells were cultured in 96 well microtiter plates in Minimal Essential Media (MEM) plus 10% heat inactivated fetal bovine serum (FBS) in the presence of 50 ng/ml human BAFF protein, 2 µg/ml goat F(ab') 2 anti-human IgM (Jackson ImmunoResearch), and varying concentrations of one of the bispecific proteins described above at 37° C. in 5% $CO^2$ for 48 hours. An anti-BAFF peptibody used as a positive control ("αBAFF," which is a homodimer containing two polypeptide chains, each comprising two BAFF-binding peptides fused to an Fc polypeptide). The αBAFF molecule is described in detail in U.S. Pat. No. 7,259,137, and the amino acid sequence of one polypeptide chain of this homodimer is provided in SEQ ID NO:32. The portions of U.S. Pat. No. 7,259,137 describing αBAFF are incorporated herein by reference. Proliferation was measured by the uptake of radioactive $^3$H-thymidine during the last 18 hours of incubation. Results are shown in FIGS. 2A and 2B.

Figure 2A:
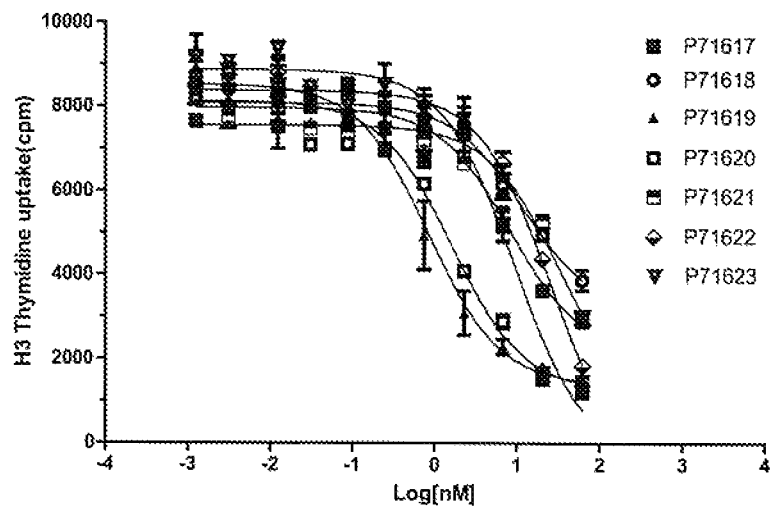
FIGS. 2A and 2B: Activity of bispecific proteins in a human B cell proliferation assay. The data shown in FIG. 2A (top) and FIG. 2B (bottom) are from a B cell proliferation assay performed as described in Example 1. In both panels, the x axis indicates the concentration (log[nM]) of the bispecific protein contained in the assay mixture, and the y axis indicates the amount of $^3$H-thymidine uptake (counts per minute (cpm)). The meaning of each symbol is indicated by an identifier for each protein assayed. Meanings of the identifiers are shown in FIG. 1 and explained in Example 1.
Figure 2B:
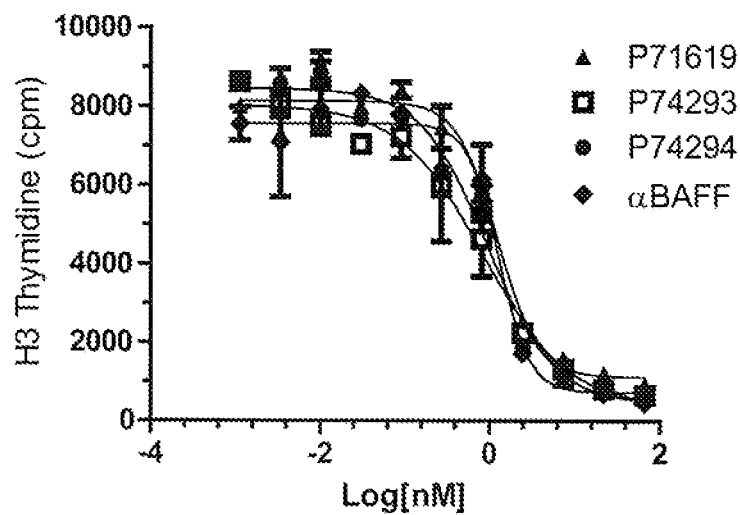

The data in FIG. 2A indicate that the two C-terminal fusion constructs (P71619 and P71620) were comparable to each other in inhibition of BAFF-mediated B cell proliferation and more potent than all of the other fusion constructs tested in this experiment. P71620 was not pursued further because it tended to aggregate, a property that is highly undesirable in a therapeutic protein. The data in FIG. 2B indicate that P71619 is comparable to the two slightly modified versions of this construct described above (P74293 and P74294) and to a positive control (αBAFF) in inhibition of BAFF-mediated B cell proliferation. Thus, among the bispecific constructs tested, P71619, P71620, P74293, and P74294 had comparable activity in this assay of BAFF-mediated B cell proliferation and better activity than all other constructs tested.

Figure 3:
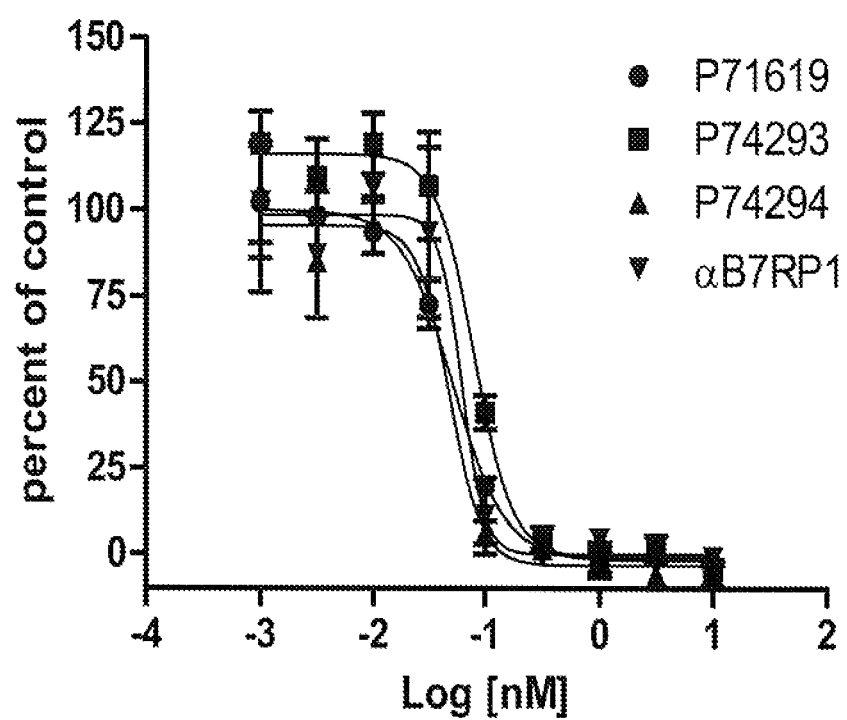
FIG. 3: Activity of bispecific proteins in a human T cell proliferation assay. The data shown is from T cell proliferation assays performed as described in Example 1. The x axis indicates the concentration (log[nM]) of the bispecific or αB7RP1 antibody in the assay mixture, and the y axis indicates percent of T cell $^3$H-thymidine uptake in the presence of B7RP1 inhibitors at the indicated concentrations relative to T cell $^3$H-thymidine uptake without B7RP1 inhibitors. The identifier for each protein tested is indicated.

The B7RP1 inhibitory activity of P71619, P74293, and P74294 was assayed using a human B7RP1-Fc-mediated T cell proliferation assay. Primary human T cells purified from PBMCs from healthy human donors using Pan T cell isolation kit from Miltenyi Biotec (Auburn, Calif.) and stimulated with plate-bound anti-CD3 (1 µg/mL) antibody and a B7RP1-Fc fusion protein (3 µg/mL) in the presence of varying concentrations of the bispecific proteins described above or an IgG2 anti-B7RP1 antibody (referred to herein as "αB7RP1"). $^3$H-thymidine was added to the cells after 48 hours, and incorporation of the $^3$H-thymidine was measured 24 hours later. All of the bispecific antibodies that were tested had similar $IC_{50}$'s, which were similar to that of αB7RP1 (FIG. 3). Thus, these data suggest that the conjugation of the BAFF-binding peptides to the anti-huB7RP1 antibody had little or no effect on the ability of the antibody to inhibit B7RP1 activity.

Three bispecific proteins, that is P71619, P74293, and P74294, were examined for properties relevant to their suitability as protein therapeutics. Protein titers of cultured host cells producing these proteins were determined. Stability of the proteins upon storage for two weeks at 40° C. was assessed by size exclusion chromatography (SEC). The percent of the protein remaining in the main peak after this storage was determined. Viscosity at 141-158 mg/mL was also measured. These data are reported in Table 2 below.

TABLE 2

Expression and physical properties of selected constructs

| Property | P74293 | P74294 | P71619 |
|---|---|---|---|
| Protein titer (mg/L) | 221 | 228 | 99 |
| Percent in main peak after 2 weeks of storage (%) | 94.2 | 94.1 | 85.7 |
| Viscosity at 141-158 mg/mL (cP) | 25.71 | 26.36 | 40.59 |

These data indicate that P74293 and P74294 were expressed at higher levels than P71619 and were also more stable and less viscous in the concentration range tested than P71619. Since the only difference between P71619 and the other two molecules lies in the linker between the two BAFF-binding peptides, these data indicate that the linkers in P74293 and P74294 (SEQ ID NO:6 and 7) conferred improved properties upon these molecules.

Figure 4:
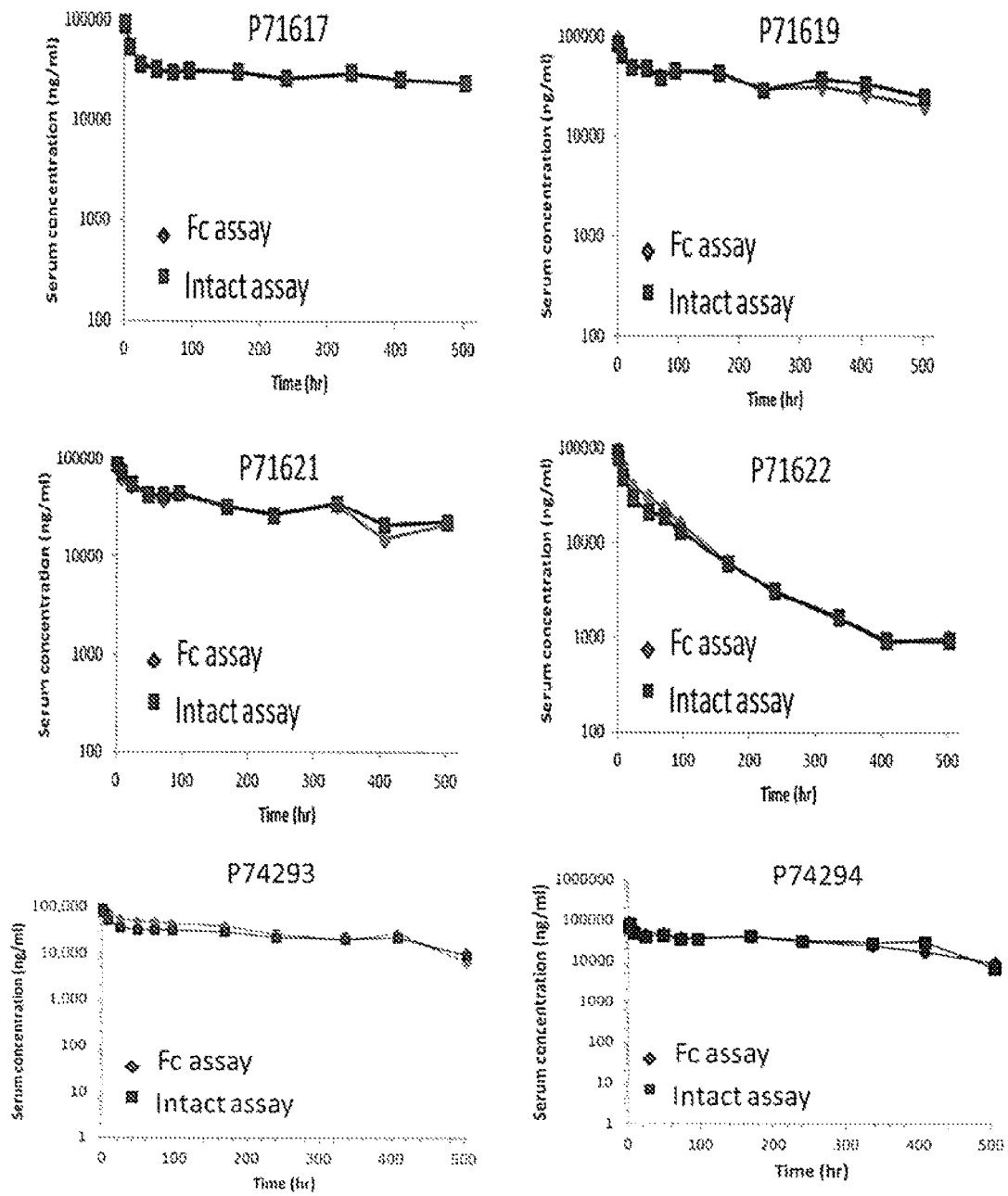
FIG. 4: Pharmacokinetic profile of bispecific constructs in mice. Methods for assessing the in vivo pharmacokinetic properties of P71617, P71619, P71621, P71622, P74293, and P74294 in mice are described in Example 1. As explained in Example 1, the bispecific proteins were detected by two different assays, one of which detected only the Fc portion of the proteins (data points indicated by filled diamonds; Fc assay) and one of which detected both the Fc and BAFF-binding portion of the proteins (data points indicated by filled squares; intact assay). The x axis indicates the time post injection (hours), and the y axis indicates the concentration of the protein detected in serum (ng/mL). The construct injected is indicated in each panel.

The pharmacokinetic properties of the bispecific molecules described were evaluated in mice. Male CD-1 mice were given a single intravenous (IV) dose (5 mg/kg) of the bispecific fusion proteins P71617, P71619, P71621, P71622, P74293, or P74294. Serum samples were collected before dosing and at 0.5, 2, 8, 24, 48, 72, 96, 168, 240, 336, 408, 504 hours after dosing. The concentration of the bispecific molecule in the serum was determined by two ELISA methods, one registering the presence of the Fc portion and one registering the presence of both the Fc portion and the BAFF-binding peptide portion. For the Fc portion measurement, a biotinylated anti-Fc antibody was used as capture reagent, and ALEXA FLUOR® 647-labeled anti-Fc antibody was used as the detection reagent. To detect the BAFF-binding portion and the Fc portion of the bispecific, a biotinylated BAFF protein was used as the capture reagent, and ALEXA FLUOR® 647-labeled anti-Fc antibody was used as the detection reagent. The bispecific proteins with two tandem copies of BAFF-binding petides fused to the N-terminus (P71617), C-terminus (P71619, P74293 and P74294) or CH3 domain (P71621) of the heavy chain have very similar PK profiles in mice. FIG. 4. The bispecific protein with one copy of BAFF-binding peptide inserted into the CH3 domain and another copy fused to the C-terminal end of the heavy chain (P71622) had lower exposure compared to the other bispecific proteins. FIG. 4. In addition, the two different ELISA assays resulted in similar serum concentrations of the bispecific proteins, suggesting that no significant cleavage of the bispecific proteins occurred in vivo.

Example 2: Designing and Testing a Murine Bispecific Surrogate Molecule

To conduct preclinical studies in mice, a murine surrogate bispecific molecule that could bind to murine B7RP1 and murine BAFF (hereinafter, the "murine surrogate") was constructed. The anti-huB7RP1 antibody used to construct the bispecific constructs described in Example 1 did not bind to murine B7RP1, while the BAFF-binding peptide used in these constructs did bind to both human and murine BAFF. Data not shown. The murine surrogate comprises an antagonistic IgG anti-murine B7RP1 antibody (called "anti-mB7RP1" herein), which was a chimera of mouse immunoglobulin constant regions and rat anti-murine B7RP1 immunoglobulin variable regions. The use of anti-mB7RP1 is described in Hu et al. (2009), J. Immunol. 182: 1421, where it is designated 1B7-V2. The murine surrogate has two copies of a BAFF-binding peptide (SEQ ID NO:1) fused via a short linker (five amino acids long) to the C-terminus of the immunoglobulin heavy chain of anti-mB7RP1. The two copies of the BAFF-binding peptide are separated by another linker that is 23 amino acids long. Nucleic acids encoding the heavy chain of the murine surrogate were made using overlap PCR to join nucleic acids encoding the BAFF-binding portion of αBAFF to the downstream end of nucleic acids encoding the heavy chain of 1B7-V2.

Figure 5A:
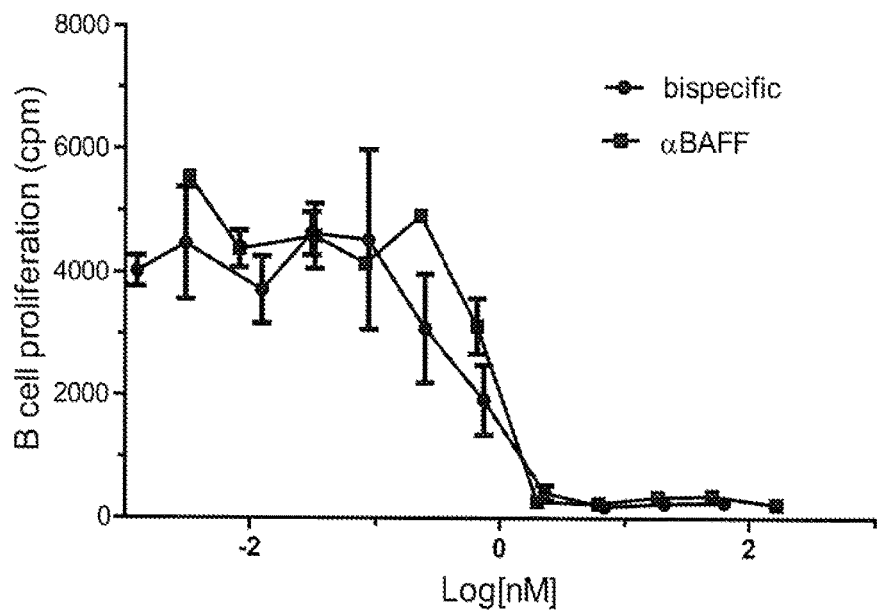
FIG. 5A: Inhibition of murine B cell proliferation by a murine surrogate bispecific molecule (the "murine surrogate") that binds to BAFF and B7RP1. The assay was performed as described in Example 2. The murine surrogate comprises an anti-murine B7RP1 IgG antibody that has two copies of a BAFF-binding peptide attached to the C terminus of the immunoglobulin heavy chain of the antibody, as explained in Example 2. The positive control was a BAFF-binding peptibody ("αBAFF"). Data from the murine surrogate and αBAFF are indicated, respectively, by solidly filled circles and squares. The x axis indicates the concentration of these test proteins in the assay (log[pM]), and the y axis indicates $^3$H-thymidine incorporation (cpm).

BAFF inhibition by the murine surrogate was evaluated in a BAFF-mediated B cell proliferation assay. Mouse B lymphocytes were isolated from C57BL/6 spleens by negative selection with MACS CD43 (ly-48) Microbeads according to the manufacturers instructions (Miltenyi Biotec, Auburn, Calif.). PBMC using a B cell isolation kit (Miltenyi Biotec, Auburn, Calif.). Purified B cells were stimulated with 0.1 μg/ml anti-IgM and 200 ng/ml BAFF in the presence of varying concentrations of the murine surrogate or αBAFF. B cell proliferation was measured by $^3$H-thymidine incorporation at day 4. The $IC_{50}$'s of the murine surrogate and αBAFF were 0.59 nM and 0.73 nM, respectively. See FIG. 5A. Thus, the murine surrogate effectively inhibited BAFF with potency comparable to that of αBAFF.

Figure 5B:
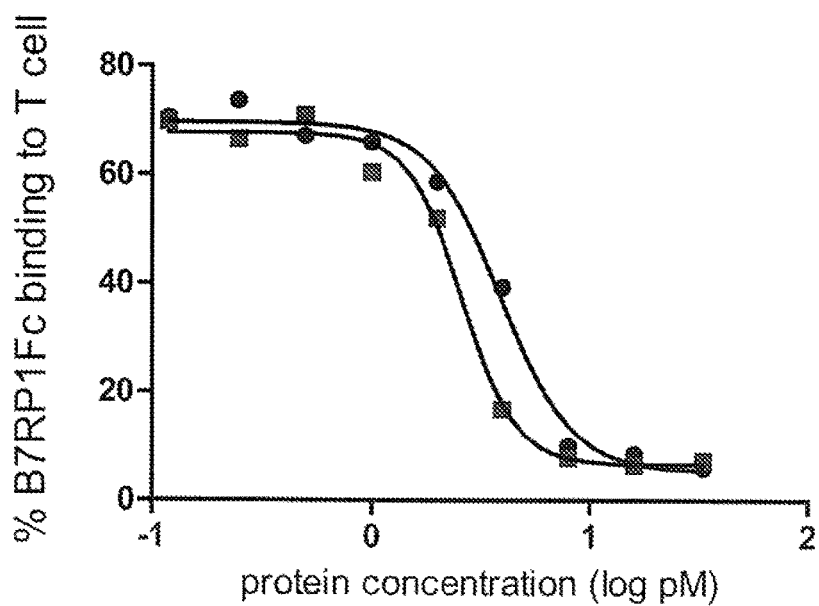
FIG. 5B: Inhibition of B7RP1 binding to murine T cells by the murine surrogate. The assay was performed as described in Example 2. An anti-murine B7RP1 IgG antibody ("anti-mB7RP1") was used as a positive control. Data from the murine surrogate ("bispecific") and anti-mB7RP1 are indicated, respectively, by solidly filled circles and squares. The x axis indicates the concentration of these test proteins in the assay (log[pM]), and the y axis indicates the percent of murine B7RP1-Fc bound to the T cells.

To measure inhibition of B7RP1 binding to its receptor by the murine surrogate, mouse spleen cells were first activated to enhance their expression of the B7RP1 receptor by incubating them in microtiter wells coated with an anti-CD3 (5 μg/ml) antibody for 24 hours. The activated spleen cells were washed with phosphate buffered saline (PBS) and then incubated with 5 μg/ml biotinylated muB7RP1:Fc in the presence of varying concentrations of the murine surrogate at 4° C. for 30 minutes. The cells were washed and then stained with allophycocyanin (APC)-conjugated anti-mouse CD3 antibody and streptavidin-phycoerythrin (Streptavidin-PE) for an additional 20 minutes. The B7RP1-Fc binding to T cells was analyzed by flow cytometry. The $IC_{50}$'s of the murine surrogate and anti-mB7RP1 were 4.01 pM and 2.8 pM, respectively. See FIG. 5B. Hence, the activity of the murine surrogate was similar to that of anti-mB7RP1 in this assay. Thus, the murine surrogate inhibits both BAFF and B7RP1.

The in vivo pharmacodynamic effects of the murine surrogate were evaluated in mice immunized with the sheep red blood cells (SRBC). In brief, BALB/c mice (8 weeks old) received a primary immunization on day 0 and a booster immunization on day 28 with 2×10$^8$ SRBC in 0.2 ml of PBS via intraperitoneal injection. The mice (n=5 for each molecule) were treated twice per week from day 0 to day 33 with one of the following molecules at 5 mg/kg: the murine surrogate; αBAFF; anti-mB7RP1; or murine IgG1. Mice treated with SBRC, but not receiving another treatment, served as positive controls. The mice were sacrificed on day 34, and serum and spleens were collected.

Figure 6:
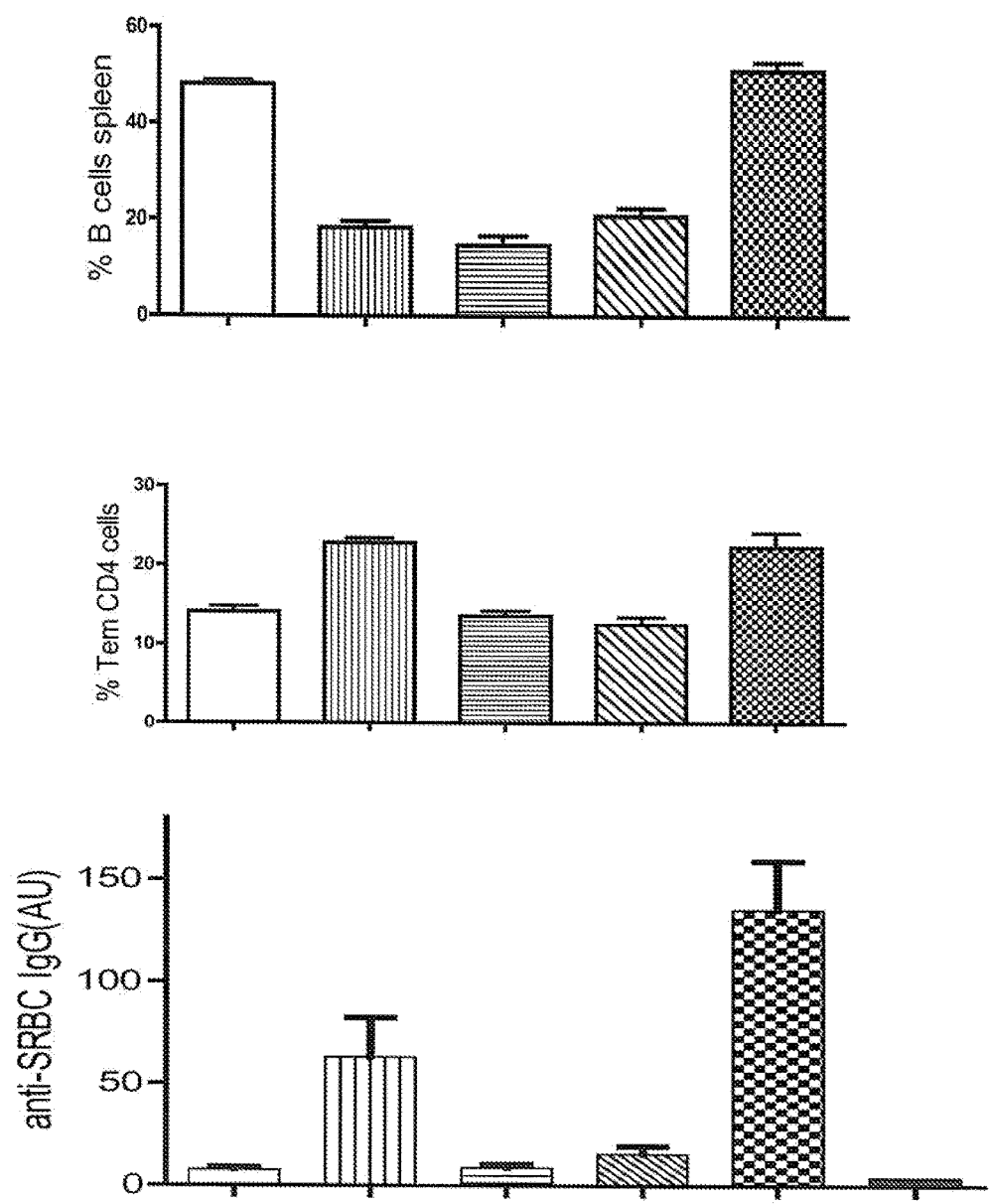
FIG. 6: All results shown in this figure are from assays described in Example 2. Top panel, percentage of spleen B cells in mice challenged with sheep red blood cells (SRBC). The proteins that the mice were treated with are indicated by the fill in each bar as follows: unfilled, anti-mB7RP1; vertical lines, αBAFF; horizontal lines, anti-mB7RP1 plus αBAFF; diagonal lines, the murine surrogate; checkerboard, mIgG1; and solid fill, mice not challenged with SBRC. The y axis indicates the percent of cells from the spleen that are B cells. Middle panel, percentage of spleen cells that are memory T cells in mice challenged with SRBC. The proteins that the mice were treated with are indicated as in the top panel. The y axis indicates the percent of cells from the spleen that are memory T cells. Bottom panel, levels of anti-SRBC antibodies in serum from mice challenged with SRBC. The proteins that the mice were treated with are indicated as in the top panel. The y axis indicates the levels of anti-SBRC antibodies detected in arbitrary units (AU), which represent the percent of the positive control.

To measure the proportion of B cells and memory T cells in the spleen, spleen cells were harvested by grinding the spleen tissue through a cell strainer. The spleen cells were preincubated with unlabelled anti CD16/32 to block the nonspecific binding of antibodies to Fc gamma receptors (FcγR). The proportion of B cells was determined by staining with PE-labeled anti-B220 (which is expressed on B cells). The proportion of memory T cells cells (CD44$^{hi}$CD62L$^{lo}$CD4 T cells) was determined by staining with FITC-conjugated anti-CD44, PE-conjugated anti-CD62L, APC-conjugated anti-CD4 and PerCP-conjugated anti-CD3. All staining antibodies were purchased from BD Bioscience (San Diego, Calif.). For both B and T cell determinations, flow cytometry was performed with a FACSCALIBUR™ (BD Bioscience, San Jose, Calif.) flow cytometer, and the data was analyzed using FLOWJO® (TreeStar Inc., Ashland, Oreg.) software for analysis of flow cytometry data. Results are shown in FIG. 6.

To measure levels of anti-SBRC antibodies in serum, microtiter plates coated with 10 μg/ml soluble SRBC antigen were incubated for two hours at room temperature with diluted serum from treated mice. Bound SRBC-specific Ig from the serum was detected with HRP-conjugated polyclonal goat anti-mouse IgG and IgM antibodies (Southern Biotech, Birmingham, Ala.). The substrate reaction was performed using SUREBLUE™ TMB microwell peroxidase substrate (KPL, Gaibersburg, Md.) according to the manufacturer's instructions, and the optical density was read using a Spectrum Max microplate reader (Molecular Devices). As a positive control, serial dilutions of a mixture of sera from SRBC-immunized mice without any treatment was added to each plate, and a standard curve was constructed from the readings from these wells. Levels of anti-SBRC antibodies of other samples are reported in FIG. 6 as a percentage of this positive control.

The percentage of spleen cells that are B cells was reduced in mice treated with the murine surrogate as compared to the percentage observed in mice treated with murine IgG1. FIG. 6 (top panel). A similar reduction was observed in mice treated with αBAFF or αBAFF plus anti-mB7RP1, but not in mice treated with anti-mB7RP1 alone. FIG. 6 (top panel). With regard to memory T cells, mice treated with the murine surrogate, anti-mB7RP1, or anti-mB7RP1 plus αBAFF had reduced proportions of memory T cells compared to that observed in mice treated with muIgG1. FIG. 6 (middle panel). In contrast, treatment with αBAFF did not alter the memory T cell population in spleen compared to that observed with muIgG treatment. FIG. 6 (middle panel). The murine surrogate also showed potent reduction of the anti-SRBC antibody level in serum, similar to that observed upon treatment with anti-mB7RP1 or anti-mB7RP1 plus αBAFF or in mice that had not been injected with SRBC. FIG. 6 (bottom panel). Moderate inhibition of anti-SRBC antibody level, compared to the level observed with mIgG1 treatment, was observed in mice treated with αBAFF alone. FIG. 6 (bottom panel). These data indicate that the murine surrogate had dual inhibitory effects in B cell and T cell compartments in mice in vivo.

Figure 7A:
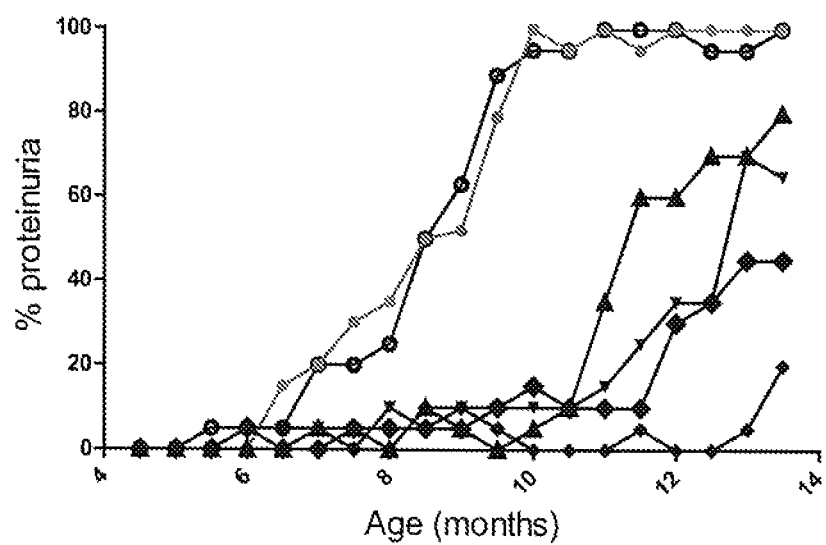
FIG. 7A: Proteinuria in NZB/NZW mice treated with various proteins. Methods are described in Example 2. The treatment for each group of mice is indicated as follows: open, large circles, phosphate buffered saline (PBS); filled small circles, murine IgG1 (an isotype control); filled, upward pointing large triangles, anti-mB7RP1; filled, downward pointing small triangles, αBAFF; filled, large diamonds, αBAFF plus anti-mB7RP1; and filled, small diamonds, the murine surrogate. The x axis indicates the age of the mice (months), and the y axis indicates the percent of mice that exhibited proteinuria, i.e., ≥300 mb/dL protein in urine.
Figure 7B:
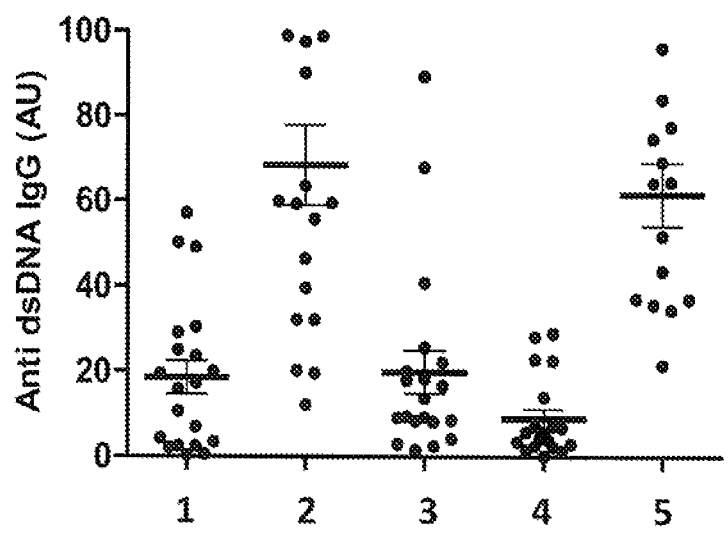
FIG. 7B: Levels of antibodies against double stranded DNA (dsDNA) in NZB/NZW mice at 8.5 months of age treated with various proteins. Methods are described in Example 2. The x axis indicates the identity of the molecule(s) that the mice were treated with as follows: 1, anti-mB7RP1; 2, αBAFF; 3, αBAFF plus anti-mB7RP1; 4, the murine surrogate bispecific; and 5, mIgG1 (the isotype control). The y axis indicates the levels of anti-dsDNA antibodies detected as a percentage of the positive control. Each dot indicates data from a single mouse.

The impact of murine surrogate on disease was evaluated in the NZB/W F1 lupus model. Female NZB/W $F_1$ mice (4.5 month old, n=20) were treated with 5 mg/kg murine surrogate (MW≅160 KDa), 4.68 mg/kg anti-mB7RP1 (MW≅150 KDa), 1.88 mg/kg αBAFF (MW≅64 KDa), a combination of αBAFF (1.88 mg/kg) and anti-mB7RP1 (4.68 mg/kg), or murine IgG1 (15 mg/kg; an isotype control) or phosphate buffered saline (PBS) (as negative controls) twice per week by intraperitoneal injection for 18 weeks. Proteinuria was measured in urine using ALBUSTIX® (Bayer, Elkhart, Ind.) every two weeks starting at 5 months of age. The incidence of proteinuria was expressed as the percentage of mice with urine protein at a concentration of at least 300 mg/dl in two consecutive measurements. Serum anti-dsDNA IgG level was measured by ELISA. At 12 months of age, none of the mice treated with the murine surrogate developed proteinuria. In contrast, 100% of mice treated with murine IgG1 or PBS exhibited proteinuria, and about 60% and 35% of mice treated with anti-mB7RP1 and αBAFF, respectively, developed proteinuria. FIG. 7A. In addition, the murine surrogate treatment resulted in a significant reduction in serum levels of anti-dsDNA IgG as compared to the negative control treated with muIgG1. FIG. 7B. In summary, dual inhibition of BAFF and B7RP1 by the murine surrogate is more effective than inhibition of only BAFF (αBAFF) or only B7RP1 (anti-mB7RP1) in preventing disease onset and progression in the NZB/W F1 lupus model.

What is claimed is:

1. A method of treating Sjogren's syndrome comprising administering to a Sjogren's syndrome patient a therapeutically effective amount of a bispecific protein comprising:
   (a) a polypeptide comprising an amino acid sequence having the following formula: A-L1-P-L2-P, wherein A is an immunoglobulin heavy chain of an IgG antibody, L1 is a first peptide linker that is absent or is 3 to 40 amino acids long, P is a BAFF-binding peptide that is 10 to 40 amino acids long, and L2 is a second peptide linker that is absent or is 5 to 50 amino acids long, and
   (b) an immunoglobulin light chain,
   wherein the immunoglobulin heavy chain of (a) and the immunoglobulin light chain of (b) can form an IgG antibody that can bind human B7RP1,
   wherein the protein can bind to BAFF and inhibit BAFF-mediated proliferation of human B cells and
   wherein the protein can bind to B7RP1 and inhibit B7RP1-mediated proliferation of human T cells.

2. The method of claim 1, wherein the IgG antibody is a human or humanized IgG1, IgG2 or IgG4 antibody.

3. The method of claim 2, wherein the IgG antibody is a human or humanized IgG1 antibody.

4. The method of claim 2, wherein P has the amino acid sequence of SEQ ID NO:1 (LPGCKWDLLIKQWVCDPL).

5. The method of claim 2, wherein L1 has the amino acid sequence of SEQ ID NO:4 (GGGG).

6. The method of claim 2, wherein L2 has the amino acid sequence of SEQ ID NO:6, SEQ ID NO:7 or SEQ ID NO:24.

7. The method of claim 6, wherein L2 has the amino acid sequence of SEQ ID NO:24.

8. The method of claim 6, wherein the antibody comprises a light chain CDR1 comprising the amino acid sequence of SEQ ID NO:8 (RASQGISNWLA), a light chain CDR2 comprising the amino acid sequence of SEQ ID NO:9 (AASSLQS), a light chain CDR3 comprising the amino acid sequence of SEQ ID NO:10 (QQYDSYPRT), a heavy chain CDR1 comprising the amino acid sequence of SEQ ID NO:11 (SYWMS), a heavy chain CDR2 comprising the amino acid sequence of SEQ ID NO:12 (YIKQDGNEKYYVDSVKG), and a heavy chain CDR3 comprising the amino acid sequence of SEQ ID NO:13 (EGILWFGDLPTF).

9. The method of claim 8, wherein the antibody comprises:
   (a) an immunoglobulin light chain variable region comprising the amino acid sequence of SEQ ID NO:14 or a variant thereof comprising not more than 10 deletions, insertions, or substitutions of a single amino acid per 100 amino acids relative to SEQ ID NO:14; and
   (b) an immunoglobulin heavy chain variable region comprising the amino acid sequence of SEQ ID NO:15 or a variant thereof comprising not more than 10 deletions, insertions, or substitutions of a single amino acid per 100 amino acids relative to SEQ ID NO:15.

10. The method of claim 1, wherein the polypeptide of (a) comprises the amino acid sequence of SEQ ID NO:16 and the immunoglobulin light chain of (b) comprises the amino acid sequence of SEQ ID NO:19.

11. The method of claim 1, wherein the polypeptide of (a) comprises the amino acid sequence of SEQ ID NO:17 and the immunoglobulin light chain of (b) comprises the amino acid sequence of SEQ ID NO:19.

12. The method of claim 1, wherein the polypeptide of (a) comprises the amino acid sequence of SEQ ID NO:18 and the immunoglobulin light chain of (b) comprises the amino acid sequence of SEQ ID NO:19.

13. The method of claim 1, wherein the bispecific protein is a tetramer comprising two molecules each of the polypeptide of (a) and the immunoglobulin light chain of (b).

* * * * *